United States Patent
Chory et al.

(10) Patent No.: US 7,632,984 B2
(45) Date of Patent: Dec. 15, 2009

(54) MODULATION OF FLOWERING TIME BY THE PFT1 LOCUS

(75) Inventors: Joanne Chory, Del Mar, CA (US); Pablo Cerdan, Buenos Aires (AR)

(73) Assignee: The Salk Institute for Biological Studies, La Jolla, CA (US)

( * ) Notice: Subject to any disclaimer, the term of this patent is extended or adjusted under 35 U.S.C. 154(b) by 329 days.

(21) Appl. No.: 10/560,652

(22) PCT Filed: Jun. 12, 2004

(86) PCT No.: PCT/US2004/018902

§ 371 (c)(1),
(2), (4) Date: May 30, 2006

(87) PCT Pub. No.: WO2004/113499

PCT Pub. Date: Dec. 29, 2004

(65) Prior Publication Data

US 2006/0242737 A1   Oct. 26, 2006

Related U.S. Application Data

(60) Provisional application No. 60/478,684, filed on Jun. 13, 2003.

(51) Int. Cl.
*C12N 15/29*   (2006.01)
*C12N 15/82*   (2006.01)
*A01H 5/00*    (2006.01)
*A01H 5/10*    (2006.01)

(52) U.S. Cl. .............. 800/298; 800/278; 800/290; 800/287; 800/320.1; 435/320.1; 536/23.6

(58) Field of Classification Search .............. None
See application file for complete search history.

(56) References Cited

U.S. PATENT DOCUMENTS

2003/0074699 A1   4/2003   Coupland et al.

OTHER PUBLICATIONS

Halliday et al (1997, The Plant Journal 12(5):1079-1090).*
Bowie et al, Science 247:1306-1310, 1990.*
McConnell et al, Nature 411 (6838):709-713, 2001.*
Fourgoux-Nicol et al (1999, Plant Molecular Biology 40 :857-872).*
Lin et al (2001, NCBI Accession No. AC079281).*
Cerdan, Pablo D. et al. (Jun. 19, 2003) "Regulation of flowering time by light quality," Nature, 423: 881-885.
Lin, X. et al. (Jan. 2001) "*Arabidopsis thaliana* chromosome 1 BAC F2J7 genomic sequence," NCBI database for nucleotide sequences, Accession No. AC079281.
Tadege, Million et al. (2001) "Control of flowering time by FLC orthologues in *Brassica napus*," The Plant Journal, 28(5): 545-553.

* cited by examiner

*Primary Examiner*—Stuart F. Baum
(74) *Attorney, Agent, or Firm*—Morrison & Foerster LLP

(57) ABSTRACT

The PFT1 (Phytochrome and Flowering Time 1) locus is described and identified. PFT1 acts in a light-quality pathway downstream of phyB that acts through modulation of FT transcription. Plants containing a truncated pft1 gene display an altered shade avoidance syndrome including an increase in time to flowering. The corresponding PFT1 gene has been isolated and characterized. Recombinant vectors, recombinant plants containing the PFT1 gene and methods of using the PFT1 gene to modulate a photosensitive trait, especially time to flowering, are described.

25 Claims, 18 Drawing Sheets

Figure 1A

Pft1 genomic sequence with upstream and downstream sequences
(numbering according to BAC F2J7)

```
26041 acaacgatcg ggatcagcaa aatctatagc tttgtagccg tcttctatga ctcatctctt
26101 ccacaaaaag tcattgacat caactagtct aagatgactg acatacgaaa ttggatccta
26161 ttttccacta ggccactctg aaaagaaaaa aacacagata aaaaggccat gcggcccatg
26221 tccaactttt ggaccaatct taaatggcct tcacaatggt tatcatggcc tttatttgat
26281 tcaagtctgg actaactaca actatgtata caaaatgttt atccacatag cccaaaataa
26341 gatatcaaat tggttacttt cattttttt tacgtgatcg accttaagct tgttgttagt
26401 tttggcgttc gatgaaccac ctccaaacca attatattct tcacaagatt ctctgcattt
26461 atcccacaga tggtaaacaa tctaatcaaa ttaaattcac ttcttcacca aaaaaaataa
26521 aattaaattc attgcccaat ttacacaaat aaaaagatag taacgaccaa gtcctttgtA
26581 tatcccattt tctattcgga gcatccAaac caaattttgt caatctaatt tatcttctcc
26641 tctcccggag aagaaggaaa cttacaattt acaaagaacg agcttcaata aaaatttcca
26701 aagaaattac cgtcggcgaa tcgttaggct cgagaagaat caccaaattc caagggggaga
26761 gagactgaat tttcttttga ttcacgtaac aacaacgctc agagactATG tcgtcggagg
26821 tgaaacagct gatcgtcgtt gctgaaggca ccgccgcttt gggtccttat tggcaaacca
26881 tcgtctccga ctatctcgag aaaatcatca ggttttttctt tttatgaacc ttgtatctct
26941 tttaatcctc gttatttgat tttcattcgg agttagggtt tagctgatac cgttcgaatc
27001 aggctttaat ttcaattggt tagatcaaac ctttgtttat cctctgattc cacaatgttt
27061 tgttgttcgt tgttagtact gtgtttatgt atttgattgt tctgtgtttc atattgagca
27121 atcactttac gttaccttat ggttcctaca ttcttttttt gtgttaggac attgttttcg
27181 atacaacgca ttcataaagc aatgaatttg tagtttctca cttcgatcac gtaaaattga
27241 tattaatatg tgattacaga gaatttagta tataattgcc tgtatagttt gtaactaatc
27301 acattgttgg ctattcttaa tatccactca acatagtatt gtatttcaaa gtagcgtttt
27361 tgtatgttaa aatttcaatt acataatctg tctatgcatt ctttgcattt gtccaggtct
27421 ttctgtggca gtgagttaaa tggagaggta ctatatctga cttatcctcg tttttaagtt
27481 tactcaagtt ttcattcttg agcaaacagt taatcaatgt ttttgaccaa actcatatac
27541 attcgttatc tgtcaaatca ttgcgacaca aaaaataaca gagcaaattg gtagtttgat
27601 gtgtctgatc gagtctttat atattcacta aacttgcaga ggaaccctgt ttctactgtt
27661 gagctatcac tggtgatctt caattctcat ggttcatatt gtggtacgtg ttgtgcttca
27721 tcttgtgata tccaaataca aatattattt gggtgctttc tcatggccct ggttacatta
27781 gcttttgttt tagtaatgtt gttcttatct ttcattcttc ttagcttgct tggtacaacg
27841 gagtggctgg acaagggatg ttgatatttt cttgcattgg ctttcttcca tacaatttgg
27901 tggtggtggt ttcaatgagg ttgccacagc tgaagggctt gccgaagcat tgatggtggg
27961 aaacttgatc tctttttcatc tgtgacacaa ctataagaca tatgtttggg ccactttctt
28021 tcaagctact tttgactaat ttacttttctc aataaaatta acttttttct ttccatggct
28081 tcattttatg tggtggtgct tctgtcagcg atttttctcga tccttaaacc tcacaatttt
28141 ctctgacttc atgacacaga tgttttctcc tccttcaggc caagctcaac caagtaacga
28201 tctgaaaaga cactgtatcc taatcacagc cagcaatcct cacatattgc caacacctgt
28261 atatcgtcca cgattgcaaa atgtggaacg gaatgagaat ggtgatgcgc aagctgagag
28321 tcgattatca gatgctgaga cagtggcttc atatttttgct aaggtacttt ttttaactga
28381 ttccccagg tattacaact agctataatt actccttta atgggaaatt actaacctgc
28441 catattggtg tgcagtgttc tgtttctttg tctgttgtat gtccaaagca gcttccaaca
28501 attagagcac tatacaatgc ggtgagactg cgtgtctatt tgctattcac tagatgtaca
28561 tctatcaaaa gtctttcttt tgtcagacag ctctttcaaa ggctgtcttt attctcaatg
28621 ctataaactg gtgtaatctt tgttttatac tgttttaaat gcagggaaag cccaatcaac
28681 aaagtgcgga cttgtcaatt gacacggcta agaacacatt ctatcttgtc ctgatctcgg
28741 agaatttgt ggaggcatgt gctgccttaa gtcattctgc tacaaatttg ccacagactc
28801 agagccctgt gaaagtggac agggccactg ttgctccatc tattccagtc actgggcaac
28861 ctccagctcc tgtgtcatca ggttcttcta ctgacaacat ccattttttct tagtccaact
28921 atcttgattt ttctttgtgc ttctttggat tctatcctgc ttctctatat gaagatctct
28981 ttttgtatga ttttcagcca atggacctat tcagaatcgg caaccagttt ctgttggacc
29041 agttccaact gctactgtga aagttgtaag tctatttgat cttttttagtc agttggagga
```

Figure 1B

```
29101 gtcagctcta tctattggca accgactctt gtatgtttta taagaattat ttactagata
29161 ttagccgaaa atgaattgta aatttattct ctggtgcttg ataagacatt acaaattttt
29221 atgtgttaat caactagatt taatgttaag ttcatatgaa tatcccattt gtgaaataat
29281 attgtatact caatcagctt attagatagc atatcttcac attagtagaa gcctgttaat
29341 cagattttg gaatgaaatt gcaggagcct agcaccgtaa cttctatggc accagttcct
29401 agtttccccc atatcccggc tgtagctcgg cctgctacac aagcaattcc ttcgattcaa
29461 acatcttcag catcaccagt ttctcaggat atggtcagca acgccgagaa tgcaccagat
29521 attaagcctg tggtggtcag tggaatgacg ccaccattgc gtactggtcc tcctggtgga
29581 gccaatgtaa atctgcttaa taatctttct caagtccgac aagtcatgag ctctgcagct
29641 ctggcaggtg cagcctcatc ggttgggcaa agtgcggttg caatgcatat gtcaaatatg
29701 atatcaacag gaatggctac atctttgcct ccttcacaaa ctgtgttttc aactggacag
29761 cagggaatta cttcaatggc tggttcgggt gcactaatgg gatctgcaca aacgggacaa
29821 agcccgggtc ctaataatgc ctttagtcct caaacaacgt caaatgtcgc ttcaaaccett
29881 ggtgtttcac aaccaatgca agggatgaac caaggaagtc attctggagc aatgatgcaa
29941 ggtggaattt ccatgaacca aaacatgatg agtggtcttg gtcaaggaaa tgtctcctct
30001 ggaacaggtg gaatgatgcc tactccagga gttggccaac aagcgcaatc aggaatacaa
30061 caacttggtg gcagtaacag ctcagctcct aatatgcagc tatcacagcc atcatcgggg
30121 gctatgcaga cttcacaatc caaatatgtg aaagtctggg aggtaatgtc agtttatctt
30181 gtctaaaata acggtgatct tgtgctaact tttacttaca ttttcaaatt catgcaggga
30241 aatttatctg ggcaaaggca agggcagcct gttcttatca ccagacttga ggtgtgttta
30301 ggggcactta ctatgcactt ttctttcccc ttttctgaat ttactgggat cacatgctta
30361 agcacatctt cctctgtaga actttgttga attgttccaa gtagatatta actaacgtct
30421 ttgtttatat ttgacagggt taccgaagtg cttctgcctc tgattcgtaa gtttataact
30481 aattgaaata tgaaaactgc ttccttacta aaccttgtca ggagagcagt cgactcctta
30541 agaaatgatt gtagctgcta aactaatttt tgctttctct ttttgtgcat ctccccaggt
30601 tggcagcaaa ctggccacca actatgcaga ttgttcgtct catatcccag gaccatatga
30661 ataacaagta atatcttcgt gctatatcct tccttattcc aaatggctca tgggtggatg
30721 ttgatttcat gccactaaat atttcacctg actttgcatc aggcaatatg ttggcaaagc
30781 tgacttcctt gtgtttcggg ccatgagtca acatgggttc ttaggacaac ttcaggataa
30841 aaagcttgtg agtattgttg ataatttatg ccacttgtct ccttttcctt attgtttcac
30901 tacaaattta ataacaaaat gatgaatggt gtttactggt ttattagata ttaggatgaa
30961 ttagatgtta agaatgaaaa tctttgaaaa aatatatgta cttacatctg taaacatgtt
31021 ctcggtgaat ctatcaatct cttgctatgt tcaccataca cttaacgatg cctacgcttg
31081 tatgtagcct tgttttgatt agcctaatcg tgtgccatac tattgtcatt ttcacgctta
31141 gcttttgtgg agttgtatat gataactttg tcatcctccg tattgcagtg tgcagtcatc
31201 cagttgccat cacagacgct tcttctctct gtctctgaca aggcttgccg cttgattgga
31261 atgcttttcc cagggtaag gaagtactaa gtttaaggtg tctatatatg ttttgcttca
31321 cattagtgac tcttgagggt tgttttgttt actcctagga tatggttgtg tttaaaccac
31381 aaattccaaa tcagcaacag cagcagcaac aacaactcca ccagcaacaa caacaacaac
31441 agcagatcca gcagcagcag caacaacaac aacacctcca acagcaacag atgccacaac
31501 tccagcaaca acaacaacaa caccagcagc aacagcaaca gcagcatcaa ttgtcacagc
31561 tccaacatca tcagcagcaa caacaacaac agcagcaaca acagcagcag catcaattga
31621 cacagcttca acaccatcat cagcagcagc agcaggcgtc gccgctgaat cagatgcagc
31681 agcagacttc gccgctcaat cagatgcagc aacagacttc gcctctgaat cagatgcagc
31741 agcaacagca gcctcaacag atggtaatgg gtggtcaagc ttttgcacaa gcccctggaa
31801 gatcacaaca aggtggtggt ggagggcagc ctaacatgcc tggagctggc ttcatgggaT
31861 AAataaaaat atcagcttca gtgctaatta attagattta tcataactta acattctttc
31921 tttcttcttt ggtcaactcg atcgtcgcca tggttttaga ctctgtttag ttgtcctttc
31981 tgttcttttg agcctgaaaa tggcatgtcc tattctgtat gggtctgacc atttagctac
``` exons= (underlined)
intron donor and aceptor sites = (bold; italic)
transcription initiation = (caps; italic)
start and stop codons =(caps; bold)

Figure 2

| | | | | | |
|---|---|---|---|---|---|
| ATGtcgtcgg | aggtgaaaca | gctgatcgtc | gttgctgaag | gcaccgccgc | tttgggtcct |
| tattggcaaa | ccatcgtctc | cgactatctc | gagaaaatca | tcaggtcttt | ctgtggcagt |
| gagttaaatg | gagagaggaa | ccctgtttct | actgttgagc | tatcactggt | gatcttcaat |
| tctcatggtt | catattgtgc | ttgcttggta | caacggagtg | gctggacaag | ggatgttgat |
| attttcttgc | attggctttc | ttccatacaa | tttggtggtg | gtggtttcaa | tgaggttgcc |
| acagctgaag | ggcttgccga | agcattgatg | atgttttctc | ctccttcagg | ccaagctcaa |
| ccaagtaacg | atctgaaaag | acactgtatc | ctaatcacag | ccagcaatcc | tcacatattg |
| ccaacacctg | tatatcgtcc | acgattgcaa | aatgtggaac | ggaatgagaa | tggtgatgcg |
| caagctgaga | gtcgattatc | agatgctgag | acagtggctt | catattttgc | taagtgttct |
| gtttctttgt | ctgttgtatg | tccaaagcag | cttccaacaa | ttagagcact | atacaatgcg |
| ggaaagccca | atcaacaaag | tgcggacttg | tcaattgaca | cggctaagaa | cacattctat |
| cttgtcctga | tctcggagaa | ttttgtggag | gcatgtgctg | ccttaagtca | ttctgctaca |
| aatttgccac | agactcagag | ccctgtgaaa | gtggacaggg | ccactgttgc | tccatctatt |
| ccagtcactg | ggcaacctcc | agctcctgtg | tcatcagcca | atggacctat | tcagaatcgg |
| caaccagttt | ctgttggacc | agttccaact | gctactgta | aagttgagcc | tagcaccgta |
| acttctatgg | caccagttcc | tagttttccc | catatccgg | ctgtagctcg | gcctgctaca |
| caagcaattc | cttcgattca | aacatcttca | gcatcaccag | tttctcagga | tatggtcagc |
| aacgccgaga | atgcaccaga | tattaagcct | gtggtggtca | gtggaatgac | gccaccattg |
| cgtactggtc | ctcctggtgg | agccaatgta | aatctgctta | ataatctttc | tcaagtccga |
| caagtcatga | gctctgcagc | tctggcaggt | gcagcctcat | cggtgggca | aagtgcggtt |
| gcaatgcata | tgtcaaatat | gatatcaaca | ggaatggcta | catctttgcc | tccttcacaa |
| actgtgtttt | caactggaca | gcagggaatt | acttcaatgg | ctggttcggg | tgcactaatg |
| ggatctgcac | aaacgggaca | aagcccgggt | cctaataatg | cctttagtcc | tcaaacaacg |
| tcaaatgtcg | cttcaaacct | tggtgtttca | caaccaatgc | aagggatgaa | ccaaggaagt |
| cattctggag | caatgatgca | aggtggaatt | tccatgaacc | aaaacatgat | gagtggtctt |
| ggtcaaggaa | atgtctcctc | tggaacaggt | ggaatgatgc | ctactccagg | agttggccaa |
| caagcgcaat | caggaataca | acaacttggt | ggcagtaaca | gctcagctcc | taatatgcag |
| ctatcacagc | catcatcggg | ggctatgcag | acttcacaat | ccaaatatgt | gaaagtctgg |
| gagggaaatt | tatctgggca | aaggcaaggg | cagcctgttc | ttatcaccag | acttgagggt |
| taccgaagtg | cttctgcctc | tgattcgttg | gcagcaaact | ggccaccaac | tatgcagatt |
| gttcgtctca | tatccagga | ccatatgaat | aacaagcaat | atgttggcaa | agctgacttc |
| cttgtgtttc | gggccatgag | tcaacatggg | ttcttaggac | aacttcagga | taaaagcttc |
| tgtgcagtca | tccagttgcc | atcacagacg | cttcttctct | ctgtctctga | caaggcttgc |
| cgcttgattg | gaatgctttt | cccagggga | tatggttgtg | tttaaaccac | aaattccaaa |
| tcagcaacag | cagcagcaac | aacaactcca | ccagcaacaa | caacaacaac | agcagatcca |
| gcagcagcag | caacaacaac | aacacctcca | acagcaacag | atgccacaac | tccagcaaca |
| acaacaacaa | caccagcagc | aacagcaaca | gcagcatcaa | ttgtcacagc | tccaacatca |
| tcagcagcaa | caacaacaac | agcagcaaca | acagcagcag | catcaattga | cacagcttca |
| acaccatcat | cagcagcagc | agcaggcgtc | gccgctgaat | cagatgcagc | agcagactcc |
| gccgctcaat | cagatgcagc | aacagacttc | gcctctgaat | cagatgcagc | agcaacagca |
| gcctcaacag | atggtaatgg | gtggtcaagc | ttttgcacaa | gcccctggaa | gatcacaaca |
| aggtggtggt | ggagggcagc | ctaacatgcc | tggagctggc | ttcatgggaT | AAataaaaat |
| atcagcttca | gtgctaatta | attagattta | tcataactta | acattctttc | tttcttcttt |
| ggtcaactcg | atcgtcgcca | tggttttaga | ctctgtttag | ttgtcctttc | tgttcttttg |
| agcctgaaaa | tggcatgtcc | tattctgtat | gggtctgacc | atttagctac | | cDNA sequence of PFT1

Figure 3

Protein sequence

```
M S S E V K Q L I V V A E G T A A L G P Y W Q T I V S D Y L E K I I R S F C G S E
L N G E R N P V S T V E L S L V I F N S H G S Y C A C L V Q R S G W T R D V D I F
L H W L S S I Q F G G G G F N E V A T A E G L A E A L M M F S P P S G Q A Q P S N
D L K R H C I L I T A S N P H I L P T P V Y R P R L Q N V E R N E N G D A Q A E S
R L S D A E T V A S Y F A K C S V S L S V V C P K Q L P T I R A L Y N A G K P N Q
Q S A D L S I D T A K N T F Y L V L I S E N F V E A C A A L S H S A T N L P Q T Q
S P V K V D R A T V A P S I P V T G Q P P A P V S S A N G P I Q N R Q P V S V G P
V P T A T V K V E P S T V T S M A P V P S F P H I P A V A R P A T Q A I P S I Q T
S S A S P V S Q D M V S N A E N A P D I K P V V V S G M T P P L R T G P P G G A N
V N L L N N L S Q V R Q V M S S A A L A G A A S S V G Q S A V A M H M S N M I S T
G M A T S L P P S Q T V F S T G Q Q G I T S M A G S G A L M G S A Q T G Q S P G P
N N A F S P Q T T S N V A S N L G V S Q P M Q G M N Q G S H S G A M M Q G G I S M
N Q N M M S G L G Q G N V S S G T G G M M P T P G V G Q Q A Q S G I Q Q L G G S N
S S A P N M Q L S Q P S S G A M Q T S Q S K Y V K V W E G N L S G Q R Q G Q P V L
I T R L E G Y R S A S A S D S L A A N W P P T M Q I V R L I S Q D H M N N K Q Y V
G K A D F L V F R A M S Q H G F L G Q L Q D K K L C A V I Q L P S Q T L L L S V S
D K A C R L I G M L F P G D M V V F K P Q I P N Q Q Q Q Q Q Q Q L H Q Q Q Q Q Q Q
Q I Q Q Q Q Q Q Q Q H L Q Q Q Q M P Q L Q Q Q Q Q Q H Q Q Q Q Q Q Q H Q L S Q L Q
H H Q Q Q Q Q Q Q Q Q Q Q H Q L T Q L Q H H H Q Q Q Q Q A S P L N Q M Q Q Q T
S P L N Q M Q Q Q T S P L N Q M Q Q Q Q P Q Q M V M G G Q A F A Q A P G R S Q Q
G G G G G Q P N M P G A G F M G
```

Predicted Protein sequence of PFT1

Figure 9A

Part 1.

Alignment Table

```
SeqA Name      Len(aa)  SeqB Name      Len(aa)  Score
===================================================
1    SoPFT1    724      2    OsPFT1    832      64
1    SoPFT1    724      3    SbPFT1    582      70
1    SoPFT1    724      4    MtPFT1    741      40
1    SoPFT1    724      5    AtPFT1    836      49
2    OsPFT1    832      3    SbPFT1    582      51
2    OsPFT1    832      4    MtPFT1    741      42
2    OsPFT1    832      5    AtPFT1    836      45
3    SbPFT1    582      4    MtPFT1    741      34
3    SbPFT1    582      5    AtPFT1    836      39
4    MtPFT1    741      5    AtPFT1    836      52
===================================================
```

Part 2.

Alignment

```
SoPFT1    MAAADRQLVVAVEGTAALGPYWSTIVAEYVEKIVRS--FCASELPGQKLAGAPPELALVV  58
SbPFT1    -------------------TRYWSTIVAEYVEKIVRS--FCASELPGQKLAGPPPELALVV  40
OsPFT1    ---------WRRRRPRGSWWWPWRGRRRWGRTGPSPWRTTSRRSCEKLAGTPPELALVV  50
MtPFT1    --MAEKQLIVAVETTAAMGPYWDTLLMDYLEKIVRC--LGGNESTGQKPSGSNVEFSLVT  56
AtPFT1    MSSEVKQLIVVAEGTAALGPYWQTIVSDYLEKIIRS--FCGSELNGERNPVSTVELSLVI  58
                  :           :*      :   .   ..  ::. . *::**

SoPFT1    FHTHGPYSAFDVQRSGWTKDTDAFLSWLSGISFSGGGFSEASTCEGLAEALKILQGSPNT  118
SbPFT1    FHTHGPYSAFDVQRSGWTKDTDAFLSWLSGISFSGGGFSEASTCEGLAEALKILQGSPNA  100
OsPFT1    FHTHGPYSAFCVQRSGWTKDMNVFLSWLSGISFSGGGFSEAAISEGLAEALMILQGSSSN  110
MtPFT1    YNTHGCYSGILVQRTGWTRDPDVFLQWLESIPFSGGGFNDAAIAEGLAEALMMFPPSQSG  116
AtPFT1    FNSHGSYCACLVQRSGWTRDVDIFLHWLSSIQFGGGGFNEVATAEGLAEALMMFSPPS--  116
          ::.**  * . ***:***:* :  ** **..* *.****.:.: .*******  ::   . .

SoPFT1    TQSHQNHEAQKHCILVAASNPYPLPTPVYCLPTQSTDHKENIETAKEPSIADAETVAKSF  178
SbPFT1    TQSHQNHEAQKHCILVAASNPYPLPTPVYCLPTQSTDHKENIETSKEPSIADAETVAKSF  160
OsPFT1    SQNHQSHEVQKHCILVAASNPYPLPTPVYRPLVQSSDHKENNDGAKESCLADAETVAKSL  170
MtPFT1    GLNQQNVDTNMHCILVAASNPYPLQTPVYVPQLQSLEKTESIDSNQVNQLYDAEAVAKAF  176
AtPFT1    GQAQPSNDLKRHCILITASNPHILPTPVYRPRLQNVERNENGDAQAESRLSDAETVASYF  176
             :  .  :  ****::****: * ****   *. ::.*. :      : ***:**. :

SoPFT1    AQCSVSLSVISPKQLPTLKAIYNAGKRNPRAADPSVDHAKNPHFLVLLSENFMEARTALS  238
SbPFT1    AQCSVSLSVISPKQLPTLKAIYHEAVVAVEAFRAYKEKVAN---LTGVTRKFMGN---LV  214
OsPFT1    LRCSVSLSVVSPKQLPTLKAIYNAAKRNPRAADPSVDHAKNPHFLVLLSDNFLEARTALS  230
MtPFT1    XQFNISLSVVCXKQN---FSHLQCGRAKGRSADPPVD-PKTTHFLILISEGFREARSALS  232
AtPFT1    AKCSVSLSVVCPKQLPTIRALYNAGKPNQQSADLSIDTAKNTFYLVLISENFVEACAALS  236
            . .:****:. **  .:    . :    :    .:        ..  *  ::  *    ::*
```

Figure 9B

```
SoPFT1    RPLHGNLAPNQTITKMDTAPAV---TMPGPTSNANPSGRQPVVGGIS------TATVKVE 289
SbPFT1    KAFKTNLP-EVVVTPAAFDFDH---IVNGPTMGSQTAG---VGGIIS------TATVTLE 261
OsPFT1    RPLPGNLVTNHPITKMDTAATS---VPVPTSNGNPSVNGPMLTRQPNGV----VANIKTE 283
MtPFT1    RPGTNMPSNQSPVKVDAVSATP---VTGAPPSSLPSVNGSIPNRQPIPAGNVTPATVKVE 289
AtPFT1    HSATNLPQTQSPVKVDRATVAPSIPVTGQPPAPVSSANGPIQNRQPVSVGPVPTATVKVE 296
          :.   :.      :.     ..    ..        *.:.  *

SoPFT1    PATMPPIVSAPAFSHVTPISNVASQ--GISALQTSSPSLISQEANMANDNVQEHKPIINP 347
SbPFT1    QPAMEPMVSGSAGFWHSALQ-------------QPSSSSLISQEANIANDSVQEHRPIRSP 309
OsPFT1    PTTLPPMVSAPAFSHVTPVANGVSQ--GLSSVQSPSPSLISQETNLANDSVQEHKPLINP 341
MtPFT1    QVPVTSG---PAFSHNPSVPRATGTGLGVPSLQTSSPSSVSQDIMTSNENAMDTKPIVS- 345
AtPFT1    PSTVTSMAPVPSFPHIPAVARPATQ--AIPSIQTSSASPVSQDMVSNAENAPDIKPVVVS 354
          .:  .  ..:    ..:    .  .: *..*.* :**:   :... : :*:  .

SoPFT1    -VQQPVRPGGHG----SLLNNLSQVRLMNSTSLG--------GGATSMGL------PNIG 388
SbPFT1    -VQHPVRPGRHG----GLLSNPSQFQPIHSTFFG--------EATTSMGP------PNIG 350
OsPFT1    -IQQSIRPGGPANV--SILNNLSQHRSVATIISGGMPGIPMSGTGQSIGSQQVVQNTAFG 398
MtPFT1    -MLQPIRPVNPAQANVNILNNLSQARQVMALSGGTS------MGLQSMGQ---------- 388
AtPFT1    GMTPPLRTGPPGGANVNLLNNLSQVRQVMS-SAALA------GAASSVGQ---------- 397
          :  ..*.   .    .:*.* **  : : :  ,         *:*       . .

SoPFT1    AT-PIQVHMSNMISSGMTSTPSVISSMSGPGHP-IGT----QQMIQSTALGS-------F 435
SbPFT1    AITPLQFNMSNMISSGATSTPLVTFSMSAPGQP-IGN----QDMVQSTALGS-------F 398
OsPFT1    SNTPITGNSNIAVSS---SLGGIQSNIGISGPP-VTQ----GGSMGSTQLGQ-------G 443
MtPFT1    --TPVAMHMSNMISSGTTSSGPTGQNVFSSGPSVITS---SGSLTASAQVGQ----NSGL 439
AtPFT1    --SAVAMHMSNMISTGMATSLPPSQTVFSTGQQGITSMAGSGALMGSAQTGQSPGPNNAF 455
          :  .:   :  .  :*:.  ::     .: . *   :         *: *.

SoPFT1    GSNTSTVSGNSN-VAVSSS----------------------------LTNNQSS 460
SbPFT1    GSNTSTAWDNSD-IAESSS----------------------------QPN---S 420
OsPFT1    GINTNQNMISSLGTTTVSS----------------------------APAMMPT 469
MtPFT1    SSLTSATSNSSXCLXEFLX---------FVRGGKVR--------SKFVVLRGPAKMMQN 481
AtPFT1    SPQTTSNVASNLGVSQPMQGMNQGSHSGAMMQGGISMNQNMMSGLGQGNVSSGTGGMMPT 515
                   . *.   ..

SoPFT1    MGMGQSVQPVAQGGLVAGSQLGQGGIGANQNVMSSLGSTAISSAPAMMPTPGMVPQTGVN 520
SbPFT1    MAMNR-----------------------------------------------QAGIN 430
OsPFT1    PGMAQ-----------------------------------------------QAGVN 479
MtPFT1    -GVN-------------------------------------------------MD 486
AtPFT1    PGVGQQA---------------------------------------------QSGIQ 527
          .:  ...   :...  :.:.  ....   .:.,.   ::  .:::  :::.:  .:..  ::..::

SoPFT1    SLGVNNNPAMNMPIPQHANAQQ-----------PAPKYVKIWEGTLSGQRQGQPVFICK 568
SbPFT1    PLSS----AMNAPIGMHHNAQQ-----------PPPKYVKIWEGTLSGQRQGRPVFISR 474
OsPFT1    SLGVTNSSAMNMPIVQHPNAQQQQQQQQQQQQQQQPPPKYVKIWEGTLSGQRQGQPIFICK 539
MtPFT1    EIGG--------QSHETQNGWHR----------SSP-----IWEGSLYGRKQGEPIFITK 523
AtPFT1    QLGGSNSSAPNMQLSQPSSGAMQ----------TSQSKYVKVWEGNLSGQRQGQPVLITR 577
          :.. ....:. .    ..         . ..  .:***.* *::**.*:* :
```

Figure 9C

```
SoPFT1    LEGYRSGTASETLAADWPETMQIVRLIAQEHMNNKQYVGKADFLVFRTLNQHGFLGQLQE 628
SbPFT1    LEGW-SGIVSKTVAADWPETMQIVRLIAQEHMNNKQYVWKGRLSNISDFKSAWFLGQLQE 533
OsPFT1    LEGYRSGTASETLAADWPETMQIVRLIAQEHMNNKQYVGKADFLVFRTLNQHGFLGQLQE 599
MtPFT1    LEGYRRSSASETLAANWPPEMHIVRIISQDHMNNKKYVGEADFLVFRARNTHGFLGLLQE 583
AtPFT1    LEGYRSASASDSLAANWPPTMQIVRLISQDHMNNKQYVGKADFLVFRAMSQHGFLGQLQD 637
          ***:   . *.::**:**  *:***:*:*:*****:**  :  :  .   *** **:

SoPFT1    KKLCAVIQLPSQTLLLSMSDKARRLIGMLFPADMVVSXPQVPTQQTQLQQQ--------  679
SbPFT1    RKLCAVIQLPSQTLPLSMSDKAGRMIGMLFPENMVIFKPEVVTQPSLVR----------  582
OsPFT1    KKLCAVIQLPSQTLLLSVSDKAGRLIGMLFPGDMVVFKPQVPTQQPPMQQQQLQQQQNQL 659
MtPFT1    KKLCAVIQLQSQTLLLSVSDKACRLMGVLFPGDKLVSKSQLSGQQQQQQ----MQQQMQ  639
AtPFT1    KKLCAVIQLPSQTLLLSVSDKACRLIGMLFPGDMVVFKPQIPNQQQQQQQQLHQQQQQQQ 697
          :********  **** **:**** *::*:***  :  ::  .::   *     :..

SoPFT1    LQQQQLPKQQQLQQELQQQQHMHMQHQASNSEAEMHFSKAEAQMP--------------- 724
SbPFT1    ------------------------------------------------------------
OsPFT1    QQQNQLHQQRQLQPQNQLQQQHQLQQQLQQQQLQQHMQLQTQGLPLQQQQSQGHPLQQQQ 719
MtPFT1    QHQQMQSQQQHLPQLQQQMQQQQQQQLPQLQQNQQLSQIQQQIPQLQQQQQ-----LP   694
AtPFT1    QIQQQQQQQHLQQQQMPQLQQQQQQHQQQQQQQHQLSQLQHHQQQQQQQQQQQQHQLT   757
                     ..  ..               .      . . .

SoPFT1    ------------------------------------------------------------
SbPFT1    ------------------------------------------------------------
OsPFT1    MQQMQQQQQQQQIQQMQQQQQMQQMQQQQQQQPQQLQQQQQPQMVGTGMGQQQPQMVGTGM 779
MtPFT1    QLQ---------------QQQLSQLQQQQQQLPQLQQLQHQQLP---------------- 723
AtPFT1    QLQHHHQQQQQASPLNQMQQQTSPLNQMQQQTSPLNQMQQQQQP---------------- 801

SoPFT1    ------------------------------------------------------------
SbPFT1    ------------------------------------------------------------
OsPFT1    GQQQPQMVGAGMGQQYMQGHGRTVQQMMQGKMAPQGPGSMPGAGSMPGGGYLS 832
MtPFT1    ------------QQQQMG-WCWNGSNLCSRS---------------------- 741
AtPFT1    -----------QQMVMGGQAFAQAPGRSQQGGGGGQPNMPGAGFMG------- 836
```

Figure 10A

Rice Pft1 genomic sequence with upstream and downstream sequences
(numbering according to BAC OSJNBa0064I23)

```
 98101 ggcacccgat tcttagttac tccctccatt ccataatata agggattttg agtttttatt
 98161 tgcattgttt gaccactcat cttatttaaa aaaattgtgc aaatataaaa aacgaaaagt
 98221 tgtgcttaaa atactttgaa taataaagta agtcacacaa aaaataaata ataattccaa
 98281 atttttttaa taagacgagt ggtcaaacag tgcaaataaa aactcaaaat cccttatatt
 98341 atgggacgga gggagtacct cctaaaaata cccttagttt agccgaaagg ctacactcaa
 98401 aactaacctg atgtatacta agaaagtaat aaatgctcac aattcttccc aactatagag
 98461 taccattatt attacattta ctaaacacca taaaagaaca atacaactct tttttacacc
 98521 aaaatttccc catattcccc tatggcccca cctgtcatcc acacaaaagc ccacctttct
 98581 tcttatgggc cttggggccc atataaatta gacccagta cccaccect tgccgtcat
 98641 ctctctctaa cctcacgaaa cctaacaaga agaagaagaa gagaaattcc ggcaaggaag
 98701 ggagggaggg agaagtcgtt ggtgcggggg agattgattt cgcgggaggg aggggagctc
 98761 gagaggcggt gattcgggga gtcggcaggg tggcgccggg tgcggcggcg gcggggcgg
 98821 ccgtcggggg gATGgcggcg gcggcggccg agaggcagct ggtggtggcc gtggagggga
 98881 cggcggcgct gggccgtac tggcccgtca ccgtggcgga ctacgtcgag aagatcgtgc
 98941 ggtaatgctg cgcccgtgct ttcctcccc cgccgcgcca ccctgctttc ttgttactag
 99001 ttgactgtac ggccgtcgcg gattagtgca tcttggattt cttgatgtgg aagaattgga
 99061 cccttttgttg attgtttagc tgtttatttt gagacgaagg gagtacatgg aacgcgaagc
 99121 ggtagctagt tagttcttga tagtggaagt tagcagctat ccgtgtatgt gtttgatata
 99181 cacagttttt tagttatatt agtcggatat atcgttcact ccaagcatta gtaggagatt
 99241 tggagatttg ttgtttgctc tcaccttctt aattgcaaac attaaatggt actagttagc
 99301 ttcaattctg tttcacaatg cttattcaaa gagtaagaat gcaagcgcat catcgatgtg
 99361 tggaaattcg tggtttcttg atgaactggt tggttgttgg ctatatggtg ttgtggcacg
 99421 agatacatct ttttttgctc ctgattcgag gagactttgt atcactgcat atgtgcagat
 99481 ctatgacaga atgtagcata attcatcttc tactttgggt tttatgcctt ttctagttcc
 99541 tccttgctca ttcagaagta ttttcttca gtctagcata tttagtgtt ttttttttca
 99601 tgaatgatga atgattccca tgaaaaccaa tttcagtttt tggctggtga ttttactact
 99661 cttctgtaca accagtaatg taatgatggg atgtctgttt ggttatggtt atggcttttc
 99721 tgaagtcctt gttttcactc ttgttaatta gttgatgttc tggtttcgca tgggtgtaat
 99781 tggaatattc atcacatgag tcaaatttct tgtgttcaag cctttcaaat aaaaaaaata
 99841 atgaaagtgg gagctgtttg tattgttggt caataatcag tttgctctga attattaggg
 99901 tttgtttgca gttgctatcc tcctgtgctt attatttagc ttctgtggaa acagttaaga
 99961 aaaacttcgt agtctgtttg agaaatcaaa ttaatgttag acgaattctg ttagtcaatt
100021 taaactgtta tttctctgac aagtgttctg tttttagaac tgaaataata tctctatttg
100081 caacttgatt aaaagagcag cagttagcca aacatcaaaa tttctataag ctactgtacg
100141 gaacaggatt atcatagtcc acctcaacgc aaaatccaaa tggagccttt gatgttatgt
100201 ggtgatccac cacagcttca ctctcatata cttactatca tgaaactttt aagctcatct
100261 cttgctagaa atttttgtca atttctgtag cacttagtaa cctttgcatt tttagtacta
100321 ctattcatga agcatttcaa tttatgcagg agtttttgtg cacatgaaat ggcaggacag
100381 gtaatttgct ctcagtattt atcgtcggac ttactacttg atccatgttt ccttgacttg
100441 tgtcaaaact caaagtgta aattattatc gtgttatgca gaagctcgca gggacacccc
100501 ctgaacttgc attagtcgtc ttccataccc atggtcctta tagcggtaaa gtttgatatc
100561 ctccatgccc taagcttttt attatgatcc attgcaatta tttgtattta gttctatatc
100621 aacaaaacat gtaagctatg ataattcgct tttgattcct tgcagctttt tgtgtgcaac
100681 ggagtggatg gacaaaagat atgaatgtgt ttcttcatg gttatctgga atatcattta
100741 gtggtggagg cttagtgaa gctgctattt ctgaaggtct tgctgaagca ttgatggtat
100801 tgacatattg gcatcgttca gttctttca cttttgcac ataatgactt cctctggtgt
100861 ttcctgtact tttttttttt ggttcaaaat gcataaatta gaaactgtgg cttactactt
100921 ccaaaatttc agtactgcat atggttgcct acttttgagt tcccgtgcaa ggttttagca
100981 ttttgtttgg cttgtgcaat catgcttcat ttggcatatg aaatgatgtt tcttttttgc
101041 caaatggcac atctttcatg ttaacatcaa cagtagcaac ctttagttcc aggcaagttg
```

Figure 10B

```
101101  gggtaggcta gagatgaaac tgatgtgcag ccacaaaaaa actaagggaa gtatagtact
101161  agtaataaca atatagttaa agaagacgtg aattaggtca tgattctggg catgtggacc
101221  gccaatttcc atgcaactct atccaaaacc ataattcatc tccacaggaa cgactgggat
101281  ttttatgatg gcttaccaat gttatcgcaa cattcttcct ttactcagcg ttaggaccag
101341  ctatgctgaa gcaaaggcag agtttggtat cttattaaca gagatatttt gatttcctag
101401  atgaagggaa atacctcttt tcatctctca ctgcacctga atttgggtcc agttttgtct
101461  aaattagttg atctacaatt ttgtttctca tagtaagccc tgtaaactat tagttgagcc
101521  tggacattat gtagaaccat gatacttaac aatacatgtt ctacccaacc ttttggatta
101581  ctttattttc caagaattat agcttgttgt cttggtattg ttatttccag tattctctag
101641  aatctgtcct ttaatgccct tctgcacaac atatgattca tgtgagaaaa ttctaaggtg
101701  gtttgcacat ccacttatca gctattgtct cataaaaaat gtcttgatct ggatatcagc
101761  tacagatagc cttaccttag taaatagagt gtaaactgt aatcaccatt tcattaggtt
101821  aatttttgta aggaagattt tcattagatc aaccctatta ggaaactgga tgtctgggcc
101881  agtacccaga ataagcagag tgaaactagt atgatcagaa gtttaaattc tatgaatgta
101941  cctatattag tatgttaatt ttcctatggt actgagtctt caaaaatcaa aatttcagtc
102001  ttcatcccta ctattataaa gagggaatcg tcctcctcca cctccacata aaagcctctt
102061  tcctccataa aaactgtcca ccctaaaaaa aactgtttac taataaagcc aaccattgta
102121  taaacaccga acagctcact gggcccaaat cctcccacta aacttaataa aaaaaaccat
102181  tgcaatgcat gacagcatga gcctataact agttgaaaaa tacttgggtc tttgaatttg
102241  atatcatttt atttcttgag ttctctatga attaaagtat ttattgcctt tatgatttta
102301  tttcctgtgt gcaactagat actccaaggc agttctagta acagtcagaa tcatcaaagc
102361  catgaagtac aaaaacattg catacttgtt gcagcaagta atccttatcc actgcctacg
102421  cctgtctacc gccccttgt tcaaagtagc gatcacaagg agaacaatga tggagcaaaa
102481  gaatcttgtc ttgctgatgc tgagactgtt gcaaatcat ttgctcaggt cctacacaaa
102541  tactgatatc tagcatattg ctgattacct gtgtttcaat gaagtggtca gcagtcattg
102601  ttggttctaa ttaattttac ttatattgat gtagtgctcc gtttcattgt cggtggtatc
102661  tcctaaacag cttccaactc tgaaagcaat atacaatgcg gtaatttcgt tattttgttt
102721  tgctaaattc tgtaagccac aagccatctt taataatctt ctcctggtat tttacttgtt
102781  cattgatggt atgatagttg catcttgatt tacagagggt tgaaaaactc acttaagaat
102841  atatctttta aaataaatta taagcatgaa cttgcagaac tggccgctcc actattacat
102901  atgttcttgt acttgtacac agtactaaac ttcatatttt cattaccatt gaaataaaaa
102961  gagtaaattt tatcaaacac cacctattat ggtccaagtt gcacaaaacc acagggatttt
103021  tggcacatga cacataaccc catgtattat ggccctaagg tttaacaaga ccacaccgtt
103081  aaccaatttt acatactcct atatcaaagt tttaaaagtt ttagttacat tcatgtaaca
103141  tttatatgat ggataaaaaa ctcataaatt tgtgatgtga ttttataaat gatcaatagt
103201  gtggttgtgt gaaactttat agctataata cctggtggtt aagtgtcacg tgccaaaacc
103261  catgtggttt tgtgcaactc agaccacaac acctaaaggt taagtgaaat ttactcaaat
103321  aaaaatgaac tcagtttgga ttgtactgtc attgtatctt atttgtggat aagaaaaata
103381  tccatttatt tcatttttt aattagttag tatcctgcct gaacttgcta gctagtcttt
103441  gtatggttta cagactataa atctatgaat tggcatcctt atctatcatt agtttaatac
103501  aagcattttt taacttacat gatataaatt ttatcttctg caagaccttc gacagtttgt
103561  actgatgaat aatttgcacc aggtgctgat gttgtccatg ttttgttgca ggcaaagagg
103621  aatcctcgag cggctgaccc atcagtggat catgcaaaaa atccacattt tcttgttttg
103681  ttgtctgaca attttttgga ggctcgaact gctctaagtc gcccttacc tggcaacttg
103741  gtcacaaatc accccattac aaaaatggat acagctgcaa catctgtgcc agtaccaact
103801  tcaaatggca acccctcagg ttgaacaaat gctaacattt ggcttagtct tgccatggta
103861  tttagccttt agttctgttc ctcttttgga cgaaaggttg tgacgttgtt acgatgtttg
103921  tgaatatgta ggtgcttaca catagtctag cgtgagtctg ctttaacaaa tgcttgacac
103981  agctttgtta aggaaaaaaa tgttaggcta aagtgaaata aaccattgcc ataattactc
104041  catggctga agcaacatag gttaacaatt atcgttgcat atattggtac gcctgactat
104101  tttaatagca ggaaggattc tggcaatgcc cttatgccat ccatttttgg cccgaaaaaa
104161  gcatatcatt gagttttcaa agccttagag gaataaaatg tattgtgagc tctcctctat
104221  tatgaacacg atgtgcttgt gcatctgaca ttacatggga ctacaatata atttcctata
104281  gtttatctcc aatttgtcaa gtacagatgc cttgagctgg agatgaagaa aaatggatgt
```

Figure 10C

```
104341 actgaataca caaacgtgaa aacctgcctc ctaaaagctt gtaccattgt gttctatttg
104401 tccccttccc atctgggtgg tttttcaatt gtagtgccaa gaaaacatag attattctat
104461 aatgattgtg tcttcatggt tatcattggc atggggtcac aactaattgt ttggactctg
104521 agtgataatg ctttcaatgg catggtgtct tcggattgat gaattctata tggataacaa
104581 gttttgtttt tcagcatctt aatcaaaatt aacactgagg atacaaatat atcgcaattc
104641 ctgttttat acacagcaat gtggttttaa aggtattcgt ggatatacat aatttgttgt
104701 ttttgtgagt gttgatgaag cccttcatt gtttgtttca taaataaaat tttacagttt
104761 aatgttatga aatgccaaat tcttattgtt tgtattgtac attgctatgt actaatatat
104821 gccagattgc ccatctacct aattaaagtg gaacatattt caagtctagc caattgctgg
104881 ttttatttgc atgatccagt tgtgataaat ctggaattgc cttatataga aatttgtttt
104941 tggcttctgg ttatatccgt atcattacta tcttccatac tgaacatgac taactgttat
105001 aagtatttt cagttaatgg acctatgctt acccgccaac caaatggtgt tgttgcaaat
105061 attaaaacgg taaagctttg aacaacatac tctgtgactt accatttgc tgtatgtttt
105121 ctcattgtga aaacaatcat cactttcagg agccaacaac tttaccgccc atggtttctg
105181 cacctgcttt ctcgcatgta acacctgttg caaatggtgt ttcacaagga ttatcatcag
105241 tacaaagtcc ctcaccgtcc cttatttcac aggaaactaa tcttgcaaat gatagtgtgc
105301 aagaacataa gcctttaata aacctatcc aacagtcaat tcgacctggt ggtccagcaa
105361 atgtcagcat cctcaacaat ctatcacagc atcggtcagt ggcaaccatt atatcaggtg
105421 gaatgcctgg catccctatg tctggaacag gacagtcaat tggtagtcaa caagtcgtac
105481 aaaacactgc ttttggatca aacacaccca taacaggcaa ttcaaatatt gctgtgttat
105541 cttcttggg tggcatccaa agcaatatcg gtatatcagg gcctcctgtg acacagggag
105601 gttcaatggg tagtacgcaa ttgggacaag gtggaatcaa tacaaaccaa aatatgataa
105661 gtagcctgg gacaacaact gtctcttctg cacctgcaat gatgccaaca ccaggatgg
105721 ctcaacaggc aggtgtaaat tctcttggtg tgaccaacag ttctgccatg aacatgccta
105781 tagtgcagca tcctaatgcg cagcagcagc aacagcaaca gcaacagcag cagcagcagc
105841 agccaccgcc gaagtacgtc aaaatttggg aggtaaaaga ttctgtcttt gtctagcatc
105901 catgtagcaa ttggctctac cctccaaccc tctagtagct tagtagttgt ttgctaaata
105961 taaaggaaa tattccgtat gacacacatg taatttaatg ttttttctaat tctgaccatg
106021 agctgcaata atatatgcac cctcccaact attgaaatcg tttgcctcaa aaataaaaa
106081 ggaactattt aaacccttct gctaatcaac cagatgagat agggctgtga atggtcagag
106141 ttagtctctt tatttttgg cctttaaca gttcccaacc tgctttttcc ttgagaaagc
106201 cttcctgaga taaaagaca acaatttgaa ggttgacctc tgggaattca gctggtgtt
106261 gtcctttgtg gcagtgtttt tgacttcaag tgctgagtca tgtcctatta accaaagaag
106321 aaagtagtgg acccaccatt gaagatgctg attatttttt catccgagta aagcctattt
106381 taccatcctc aactgtgtta gtctagaaat caacctcagc agaggccccc ttcgtaccat
106441 gaaccatgct ggtggtggaa ggggtgcgac tattctgcaa tacccctatag acacatgcca
106501 cgtgtctcta ggggcaggtc atttgcggca tcaaggtgac acataaatcg ccttgatctg
106561 ttggcattag caaaggtgtt gaagggtcta gttagtaaga aactaacatt agtctttaat
106621 ctattctccc ctgtccttgt ggagttgtgg tgcagctgct tcgatggtat tgtctctccg
106681 tgtgcaagga cacctcaatt aagtgcataa gaacctgtat ggctgtatcc ataccacatt
106741 catttcatgt atgaagaata cttccctaaa agagctaaca tacgagcaca tgattatatc
106801 taaattagtt tgaagtcaac tgcttatttt tccgtgtcat ttttggttgt ttatatatta
106861 gtaatgtaaa tttatgttc tatttatcgt gtctcaagtt gcctatgtt atgatactgg
106921 tatcatcagt caatatatga tttgttgtt gtggatgcat aatatgtaat gtttctattt
106981 ttatttcagg gaactttatc tgggcaaagg caaggacaac ctgtatttat ctgtaaactt
107041 gaagtaagtt tctgtttgtt ggatgaattg tctgtgactc cgactattat caccccccta
107101 actctgccca cacagatgac cttgctcat tattatgccc atttgaagct gactgtctca
107161 gaaagaaaaa aagatcacaa gaatccctga attgtatata ttatttgtac gatcatgatt
107221 gtcaaatct tctgttgtca ctgaaatgaa attatgtatt tcatagtttc agtgtgcacc
107281 tttatagctg gaatatagtg gctatccttt tgttgtaact acttgtccta cattttttt
107341 tgtttcaaca catttatctg cacaaagcat atactttagt taaatttctg acttttagca
107401 tgtctcacag ggttacagga gtggaacagc atctgaaacg taagttttcg aattgttgca
107461 atgttcttgc attctttttt tttttttgt agttctgttt tgtgtctatt aatggttgta
107521 ttcgaaccaa caaatcaccc aatgtcggta tgccctattt tagtattgtt ttgtagaaga
```

Figure 10D

```
107581 actggagcaa tggctgattg gtagctgctt ggtattcaca agtttctgtt ccatgcaaca
107641 actagttaag ccattgcttg tttttaaaaa ataaactgta ctgtacaaaa ggtctacggt
107701 acaagaccaa aatggaagca actcaagtta taatgttgga agtttttaga tataatcaat
107761 gaatgctgtg gatttgcttt atactccctc cgtctcatat tataagggat tttgggtgta
107821 tgtgacatat cctatgtcca ggttcgtagt actaaggata tgtcacatcc acccaaaatc
107881 ccttataata taggactgag ggagtagtac agtgccttaa tcttgttaag tgaatggaac
107941 ctccaaaccg atcttgcaaa attcctaata ggatattttg cctaatatag aaatgtcttg
108001 ttcccttgca ctgaacatgt accttctata atgtcgttcc cttgcactga acatgtacct
108061 tctttgtcca gacttgcagc agactggcct gaaacaatgc agattgtgcg ccttatagct
108121 caggagcata tgaacaataa gtttgtctca gccactccat ttccatgtta aaaatgatcc
108181 attctacatt ctcataattt gaatcattct ctcttttgtt tttgtttatt tgtttattct
108241 gcagacaata tgttggaaaa gcagactttc tagtatttcg gacattaaat cagcacggct
108301 tccttgggca actgcaggaa aagaagctgg tcagtgcata atttaacctg tttaatgttt
108361 attattattt catgccacaa ttatttggtc ccacatctat tgcatgccac tcatatgggt
108421 ccttcaacta gtcaaattag tccccaagct ttgttaattg gctcattgta atccctgtgc
108481 ctatgtgtca ccgcatgttg tctcatctca ctcaagtcag cgactaggta cctagggtct
108541 ccagccaacc tagagtatgg gacaaccgaa ttccgtttgc taaattatgt aatataattg
108601 aagacagaag taggctgctg ttatgcttga gggcatatca gtcattttat atagtcttgg
108661 gtggcctcag gttcccagca gatcaaggca atgtttgatg gttgagggat acatgaacta
108721 ttaatccttc cgtttaatca atcatcactt cttaaatttc tgttaatgtt tcgagtggac
108781 ttctgtttca gtgcgcagtg attcaactgc cttcgcaaac tttgttgttg tcagtgtcag
108841 acaaagctgg gcgcctcatt ggcatgctgt tccctggggt acgttgattg cagttgcggc
108901 tatctctatc tgccttgctg tttaccattt ttccgctgta gctgaagtaa ttccttttccc
108961 cccaggatat ggtggtgttt aaaccgcagg taccaaccca gcagccacca atgcagcaac
109021 aacagttaca acagcagcag aaccaactac aacagcagaa tcagctccac cagcagcacc
109081 agctgcaacc acagaaccag ctgcaacagc aacaccagct gcaacaacag ttacaacagc
109141 agcaactaca acaacacatg caactgcaga cacaaggcct tccgcttcag cagcagcaat
109201 cccaaggcca tccgcttcag cagcagcaga tgcagcaaat gcagcaacaa cagcagcagc
109261 agcagattca gcaaatgcag cagcagcagc agatgcagca gatgcaacag cagcagcagc
109321 agccccaaca gcttcagcag cagcagcaac cgcagatggt cggcacaggg atggggcagc
109381 agcaaccaca gatggtcggc acggggatgg ggcagcagca accgcagatg gtcggcgcag
109441 ggatggggca gcaatacatg caggggcacg gtaggacggt gcagcagatg atgcaaggga
109501 agatggcgcc gcagggtcca ggaagcatgc cgggtgcagg gagcatgcct ggggtggct
109561 acctatctTG Aagcacctga tagcctgaat gccagaagaa taagtgggca atttaaccca
109621 gccctttgg ctgcacaagc tatatagctc atggattact tgcccagcat cctaggtaat
109681 tttcccacct tagtgtggga tacatagtag gtgttctcag tagtttggtt ttggctgtga
109741 tgttttacct gtagatagcg tcttggagcc tacacggcct catgttgtgt tttgtgtagc
109801 ttcttttgat gtcactgcct tatgcttagc ttgtagctgc tggaagcaga tcaaatttaa
109861 aggattaatt aattaatagt aactctgttt aaggattgat tgaccaattc cacttgggag
109921 cctcccaaat aaatatgact gccttaggat ttttcagctt tgtaattgat gcatcaagag
109981 tatggcagag tggcagtaac tgattaaaat tattgtcatc aaattcgaac caatttaccc
110041 taaattaaaa tgctggccta tgaaggaatc caaacatatt gggattacac aggcaagatc
110101 attcacagaa aaagatacgt tcaagatgac catgacgatg aaaaagggcc tgcataggaa
110161 ttaaattgtc tgcccacggt gctaaacaac aaacaaaata aacttttatg taaatattgc
110221 taaccatatc attacagttt ggtcttgata ctgctctaca gttatgagta acatcaatta
110281 caataaatag aatcgagaag agttctaaat gaaacaatga ccgccccagc cttcaatttt
110341 cttccctcca aaacacatgt tagctttcaa ttcttcagac atctttttt ccaaaaacaa
110401 aacaaactat tggaatggcc agaaccagta caagtgcatt ttactctaca ggttggccaa
110461 tgatttgtat gcgtcaattt ttctttggat ccgagcttcc gttcaggtag ccttcaagaa
110521 ttgtgttgca ggcattcatg gctcgcgcat ccagtagact gtggtccag agtttgacca
110581 taaaaaacct ccaacacctg ttcatccagc gataaaaagt tgcaaatgaa acaaacagct
110641 aaagagaggt gtctgcatct gtaggcaaca agctacacac gcaaggcaag gcattgatca
110701 atactatatt cttataatca gccacttacc atagtagagc tggattttgt acaagttctt
110761 gtccatgaaa ctgcgagaat gcttcgcatg cccagggaat atggccatcc gctagtaccc
```

Figure 10E

```
110821 tgcaattttc cacttttcag taagacggtt gaaatatgca gtagataatg aataaaatga
110881 ctgcacatat gtaaaaggaa tcaagtgccc ttgcagttct gatgtcactg cttaactctt
110941 ggtatggaaa aagaagaaa aaaaaagtaa aaacaatcct ttgggcatat agttggtaga
111001 gatagaggtg ggattcaatg tagatgaggg gtgctagccc atgacaatgt atggttgatt
111061 acgtacgcca caggcaacaa cagcatggtg atatatgtgc gcttaggatg cccaaatgcg
111121 actgggagta gtgttggtgg catcggcaaa ggtgcgagaa acagaggtgc tgacaatcat
111181 ggcatcttag taaaggttag cagcaaggag gaagaaggca ttactagtat tagttttcc
111241 gtcctaagaa aataacaatc agagccataa cacctggcac attacaagtt gtaattcatg
111301 gctcttaacc catgcaattc ttaaaaaaaa aaaacatgca acatcttcat ggaagaaatc
111361 cttcatgata gtttcagaca tggtatgcaa atgaatataa atgtctgttc accaagctgt
111421 ataccacaat aatagataat ggatatagcg gggaaggcct gacctttgtt tccgaacaaa
111481 tgaattccac atatgcataa taagtttctc gtcttttgta acatcaacaa aatcatcaag
111541 catctgcatt tactcaggga agttaaggta tcaagaattt ggacacattt atgtatgaga
111601 acagagcaag catagtaaac ttactcttct atcttcaaaa tcagcaatgt catcatcaac
111661 ttcatcttca ctatcacgat ctgagaaaac ttgctccaat gccattggct acaacagtgt
111721 aactatgtag tcaagctaga tttcaatttt atttgagcca gacttcaaac ggatgcaaaa
111781 aagatcatgt cttcataatt aaaaaaaaaa tgacaaaagg ggaagagggg ctcaagtttg
111841 gccatccaac catagattct ccacataaga ttagctagat atgcatgcgt ttccaaagtg
111901 gctggttttg aaatctgtta ctgcaaagtt tgataatata tatatgccag tgaatgtgaa
111961 atatgccatt gtgaataatt ttggaccaaa gcaccctgt ttcttattcc tccattatcc
112021 ttaattcatt gtttcctgt cgccatgggg gccccacaa ctaaatttg cctcatgcac
112081 tagatccaca tggtggctat aaccaaggct gagctacccg catggactca tgatgagcat
112141 ccatgttact gccatatcca caggattgag cttttctaca gcataacgtt gctggggtta
112201 cttggctaa gatgctgcca tgctcacccc ttgggatagc agtggttcaa accagtgatt
112261 gctgtgtcaa cggcaacgtg tgatatctgt gttgacttga tcctcaaaca tgggaagtct
112321 cgggtgaaac ctcaccaaa tggagtgaaa tgtgaatcag gtgttcagcc agacttgggg
112381 aagatggtca tgccagccct atgccaagtg acatgactgg gagggaggga aagatcccac
112441 tgagtacaac agtggcagtt agccatggga gggtgataca agttggcaat gctatatttc
112501 aaagggaaaa catttcccag accatggatt cttttctgg cagccaggtc cctgatgcct
112561 tagtcatcgg caagcttgat ttggcactta gtcagttctg atcctttcct acagttcatc
112621 cttttctct atttctattt tgttgaccca gtaactagtc caaaaaccct ggttattctt
112681 ggttacgtaa cttactactc cctccaattt cccaactgat catcatataa ctttttaag
112741 gttattccca aatgatcatc atattagtat tcattcacta agtctgttcg ttattctgtg
112801 catgggagta gatggacatt ggtgcatgcg tccatgcata caatcccttta caaccaacat
112861 gcaatgtttt gatttgttag tggctaggaa gtattgggga tagtgcatgc aagtttgtta
112921 ccgaattaaa tgtagtatga gagaattatt agcttccctt ggtcttggtc ttataatatg
112981 atgatcaatt gggaatggag gtagtagtaa gaaatcgatt agttttttag atgagaaatg
113041 cagacgagta gggaggacat ttctgatgt ttctctcgtg accatccaga gtgatagcag
113101 gaaacttttg attgacgtat agaaaatttc accatctata taacccttta ttaactccaa
``` exons = (underlined)
exons predicted from Maize EST and comparing to Arabidopsis sequence or
    deduced from the Arabidopsis sequence = (underlined, italic)
intron donor and aceptor sites = (bold; italic)
transcription initiation = (caps; italic)
start and stop codons =(caps; bold)

Figure 11

Rice PFT1 putative protein sequence

```
W R R R R P R G S W W W P W R G R R R W G R T G P S P W R T T S R R S C E K L A G
T P P E L A L V V F H T H G P Y S A F C V Q R S G W T K D M N V F L S W L S G I S
F S G G G F S E A A I S E G L A E A L M I L Q G S S S N S Q N H Q S H E V Q K H C
I L V A A S N P Y P L P T P V Y R P L V Q S S D H K E N N D G A K E S C L A D A E
T V A K S L L R C S V S L S V V S P K Q L P T L K A I Y N A A K R N P R A A D P S
V D H A K N P H F L V L L S D N F L E A R T A L S R P L P G N L V T N H P I T K M
D T A A T S V P V P T S N G N P S V N G P M L T R Q P N G V V A N I K T E P T T L
P P M V S A P A F S H V T P V A N G V S Q G L S S V Q S P S P S L I S Q E T N L A
N D S V Q E H K P L I N P I Q Q S I R P G G P A N V S I L N N L S Q H R S V A T I
I S G G M P G I P M S G T G Q S I G S Q Q V V Q N T A F G S N T P I T G N S N I A
V S S S L G G I Q S N I G I S G P P V T Q G G S M G S T Q L G Q G G I N T N Q N M
I S S L G T T T V S S A P A M M P T P G M A Q Q A G V N S L G V T N S S A M N M P
I V Q H P N A Q Q Q Q Q Q Q Q Q Q Q Q Q P P P K Y V K I W E G T L S G Q R Q G Q
P V P I C K L E G Y R S G T A S E T L A A D W P E T M Q I V R L I A Q E H M N N K
Q Y V G K A D F L V F R T L N Q H G F L G Q L E K K L C A V I Q L P S Q T L L L
S V S D K A G R L I G M L F P G D M V V F K P Q V P T Q Q P P M Q Q Q Q L Q Q Q Q
N Q L Q Q Q N Q L H Q Q H Q L Q P Q N Q L Q Q Q H Q L Q Q Q L Q Q Q Q L Q Q H M Q
L Q T Q G L P L Q Q Q Q S Q G H P L Q Q Q Q M Q Q M Q Q Q Q Q Q Q I Q Q M Q Q Q
Q Q M Q Q M Q Q Q Q Q P Q Q L Q Q Q Q Q P Q M V G T G M G Q Q Q P Q M V G T G M
G Q Q Q P Q M V G A G M G Q Q Y M Q G H G R T V Q Q M M Q G K M A P Q G P G S M P
G A G S M P G G G Y L S
```

MODULATION OF FLOWERING TIME BY THE PFT1 LOCUS

CROSS REFERENCE TO RELATED APPLICATIONS

This application is a U.S. national phase application of International Application No. PCT/US2004/018902, filed Jun. 12, 2004, which claims priority to U.S. Provisional Patent Application Ser. No. 60/478,684 filed Jun. 13, 2003, the contents of which are hereby incorporated by reference into the present disclosure in their entirety.

RELATED APPLICATIONS

This application claims priority to U.S. Patent Application No. 60/478,684, filed Jun. 13, 2003, which is herein incorporated by reference in its entirety.

GOVERNMENT SUPPORT

This invention was made with United States government support under Grant No. GM52413 from the National Institutes of Health. The United States Government has certain rights in this invention.

BACKGROUND OF THE INVENTION

1. Field of the Invention

The field of the invention relates to methods of modulating at least one trait in a plant. Such traits include increased or decreased time to flowering and other traits associated with the shade avoidance syndrome. Also encompassed are transgenic plants produced by the disclosed methods.

2. Description of the Related Art

The influence of light on plant growth and development has been a topic of interest from the earliest studies of plant physiology. Flowering plants are subject to photoperiodism which is generally defined as the response of plants and animals to relative lengths of day and night. Plants are also sensitively attuned to differences in light quality. Red light, Far red light and blue light receptors are well characterized across plant species. One aspect of plant physiology that is particularly affected by photoperiodism and light quality is flowering.

The transition to flowering in plants is regulated by environmental factors such as temperature and light. In *Arabidopsis thaliana*, much is known about the photoperiod pathway that induces flowering in response to an increase in daylength. In contrast, the mechanisms that regulate flowering in response to changes in light quality are largely unknown. In crowded or shaded environments, the red/far-red ratio of incoming light reaching plants decreases, and a series of responses known collectively as the "shade avoidance syndrome" are triggered, including the promotion of stem elongation and acceleration of flowering (Ballare, C. L. *Trends Plant Sci* 4, 201, 1999; and Halliday, K. J., et al. *Plant Physiol* 104, 1311-1315, 1994). Phytochromes are a family of red/far-red-light photoreceptors essential for the perception of changes in light quality and shade avoidance responses; among the 5 phytochromes in *Arabidopsis*, a phytochrome B (phyB) plays the most significant role in the shade avoidance syndrome. The mechanisms by which phyB regulates flowering are largely unknown.

The phytochromes and the blue/UV-A photoreceptors called cryptochromes (cry1 and cry2 in *Arabidopsis*) are the most critical photoreceptors that regulate floral induction (Lin, C. *Plant Physiol* 123, 39-50, 2000). Several components involved in phytochrome signaling in seedlings have been isolated and characterized in recent years (Quail, P. H. *Nat Rev Mol Cell Biol* 3, 85-93, 2002). Seedlings defective in phytochrome A (phyA) signaling are tall under far-red light (FR) while plants defective in phyB signaling are tall under red-light (R). Despite the large number of components identified, it remains unclear how they are assembled into a signaling network. ELF3 and GI have been reported to have a role in flowering (Liu, X. L., et al. *Plant Cell* 13, 1293-304, 2001), mainly through mis-regulation of the circadian clock (Suarez-Lopez, P., et al. *Nature* 410, 116-20, 2001), but the mechanisms by which phytochromes regulate flowering directly are largely unknown. Using a new genetic screen for seedlings showing an enhanced response to R light and flowering time defects, a new recessive mutant, pft1 (phytochrome and flowering time 1) was isolated; the PFT1 locus was cloned and characterized in detail. PFT1 (PHYTOCHROME AND FLOWERING TIME 1) is a nuclear protein that plays an essential role in regulation of flowering time by phyB, acting downstream the photoreceptor to regulate the expression of the floral induction gene, FLOWERING LOCUS T (FT). As used herein, upper case refers to the wild type form of PFT1 and lower case refers to the mutant form.

SUMMARY OF THE INVENTION

In one embodiment, the present invention includes a phytochrome and flowering time 1 (PFT1) protein or a nucleic acid molecule encoding a PFT1 protein. In a preferred embodiment, the PFT1 protein has the amino acid sequence set forth in SEQ ID NO: 3 or SEQ ID NO: 17 or a conservative variant of the sequence shown in SEQ ID NO: 3 or SEQ ID NO: 17. In another preferred embodiment, the nucleic acid molecule has the sequence shown in SEQ ID NO: 1 or SEQ ID NO:2 or SEQ ID NO: 16 or homologous sequence to the sequence shown in SEQ ID NO:1 or SEQ ID NO:2 or SEQ ID NO: 16. In certain embodiments, the PFT1 protein is at least about 50%, at least about 60%, at least about 70%, at least about 75%, at least about 80%, at least about 85%, at least about 90%, at least about 95%, at least about 97%, at least about 50%, or at least about 99% identical to the sequence shown in SEQ ID NO: 3 or SEQ ID NO: 17. In other embodiments, the PFT1 protein is encoded by a nucleotide sequence that hybridizes to SEQ ID NO:2 or SEQ ID NO: 16 under very high stringency hybridization, under high stringency hybridization, under moderate stringency hybridization or under low stringency hybridization. In still other embodiments, the PFT1 protein encoding nucleic acid is at least about 50%, at least about 60%, at least about 70%, at least about 75%, at least about 80%, at least about 85%, at least about 90%, at least about 95%, at least about 97%, at least about 50%, or at least about 99% identical to the sequence shown in SEQ ID NO: 1 or SEQ ID NO:2 or SEQ ID NO: 16.

In another embodiment, the present invention includes the above nucleic acids molecules operably linked to a promoter. In certain embodiments, the promoter may be a constitutive promoter, an inducible promoter, or regulated promoter such as a developmentally regulated, spatially regulated or temporally regulated promoter. In other embodiments, the promoter is functional in plants, in monocots, or in dicots. Another embodiment of the present invention includes any of the above nucleic acids in a vector or other genetic construct such as a viral genome.

In still another embodiment, the present invention includes transgenic plants expressing a PFT1 protein as exemplified above or comprising any of the above nucleic acids, vectors or other constructs. In certain embodiments, the expression of the PFT1 protein may be limited to particular times, or particular tissues, such as during the day or during the night, or in the seeds, fruits, fruiting bodies, leaves, stems, flowers, or roots. The present invention also includes transgenic plant parts such as seeds, fruits, fruiting bodies, leaves, stems, flowers, or roots. In certain embodiments, the plants may be wheat, barley, rye, oat, flax, millet, corn, tomato, rice and tobacco plants.

In one embodiment, the present invention is drawn to a method of modulating at least one photosensitive trait in a plant which includes altering the level of phytochrome and flowering time 1 (PFT1) protein in a plant In a preferred embodiment, the photosensitive trait is flowering time, shade avoidance syndrome, stem elongation or leaf number. In a preferred embodiment, the PFT1 protein has the amino acid sequence set forth in SEQ ID NO. 3 or SEQ ID NO: 17 or a conservative variant of the sequence shown in SEQ ID NO: 3 or SEQ ID NO: 17. In certain embodiments, the PFT1 protein is at least about 50%, at least about 60%, at least about 70%, at least about 75%, at least about 80%, at least about 85%, at least about 90%, at least about 95%, at least about 97%, at least about 50%, or at least about 99% identical to the sequence shown in SEQ ID NO: 3 or SEQ ID NO: 17. In other embodiments, the PFT1 protein is encoded by a nucleotide sequence that hybridizes to SEQ ID NO:2 or SEQ ID NO: 16 under very high stringency hybridization, under high stringency hybridization, under moderate stringency hybridization or under low stringency hybridization.

In one embodiment, the level of PFT1 protein is altered by producing a plant having an expression vector having a gene encoding the PFT1 protein. In a preferred embodiment, the gene encoding the PFT1 protein has a nucleotide sequence that encodes the amino acid sequence set forth in SEQ ID NO. 3 or SEQ ID NO: 17 or a conservative variant of the sequence shown in SEQ ID NO: 3 or SEQ ID NO: 17. In another preferred embodiment, the gene encoding the PFT1 protein has the nucleotide sequence set forth in SEQ ID NO. 2 or SEQ ID NO: 16.

In one embodiment, the present invention is drawn to a method of modulating a photosensitive trait in a plant, including:
  transforming a plant cell with an expression vector including a gene that encodes a PFT1 protein; and
  growing the plant cell into a plant under conditions that allow the expression of the PFT1 protein thereby modulating a photosensitive trait.

In a preferred embodiment, the PFT1 protein is overexpressed in the plant. In a preferred embodiment, the PFT1 protein is encoded by a gene including the nucleotide sequence shown in SEQ ID NO: 2 or SEQ ID NO: 16. In another preferred embodiment, the PFT1 protein is encoded by a gene including the nucleotide sequence shown in SEQ ID NO: 2, from nucleotides 1 to 2512. In one preferred embodiment, the expression vector includes a constitutive promoter. In an alternate preferred embodiment, the expression vector includes an inducible promoter.

Preferably, the plant is a tomato, rice or tobacco plant. In some preferred embodiments, the plant is *Arabidopsis thaliana*.

In a preferred embodiment, the photosensitive trait is a trait selected from the group including: flowering time, leaf number, stem elongation, and red/far red response. In a more preferred embodiment, the photosensitive trait is flowering time, and the flowering time is decreased.

In one embodiment, the present invention is drawn to a method of modulating a photosensitive trait in a plant which includes contacting a plant cell, or plant, with an inhibitor of a PFT1 gene such that expression of the PFT1 gene is reduced compared to a plant not contacted with the inhibitor. Preferably, the PFT1 gene includes the nucleotide sequence shown in SEQ ID NO: 2 or SEQ ID NO: 16. In another preferred embodiment, the PFT1 gene includes the nucleotide sequence shown in SEQ ID NO: 2, from nucleotide 1 to 2512.

In a preferred embodiment, the inhibitor includes an expression vector expressing a protein that inhibits expression of the PFT1 gene. In a preferred embodiment, the plant is selected from the group including wheat, barley, rye, oat, flax, millet, corn, tomato, rice and tobacco plants.

In a preferred embodiment, the inhibitor includes an antisense molecule that inhibits the PFT1 gene. In an alternate preferred embodiment, the inhibitor includes a short interfering RNA (siRNA) configured to inhibit the production of a PFT1 gene product.

In a preferred embodiment, the photosensitive trait is a trait selected from the group including flowering time, leaf number, stem elongation, shade avoidance syndrome and Red/Far Red Response. In a more preferred embodiment, the photosensitive trait is flowering time, and said flowering time is increased. In a more preferred embodiment, the photosensitive trait is shade avoidance syndrome, and the plant exhibits a depressed shade avoidance syndrome.

In one aspect, the present invention is drawn to a transgenic plant having at least one modulated photosensitive trait as compared to a wild-type plant, wherein the transgenic plant includes a recombinant expression vector that expresses a nucleic acid encoding a PFT1 gene. In a preferred embodiment, the PFT1 gene is overexpressed. In a preferred embodiment, the PFT1 gene includes the nucleotide sequence shown in SEQ ID NO: 2 or SEQ ID NO: 16. In another preferred embodiment, the PFT1 gene comprises the nucleotide sequence shown in SEQ ID NO: 2, from nucleotides 1 to 2512. In a preferred embodiment, the expression vector includes a constitutive promoter. In an alternate preferred embodiment, the expression vector includes an inducible promoter.

In a preferred embodiment, the transgenic plant is selected from the group including tomato, rice and tobacco plants. In alternate preferred embodiments, transgenic plant is *Arabidopsis thaliana*.

In a preferred embodiment, the photosensitive trait in the transgenic plant is a trait selected from the group including: flowering time, leaf number, stem elongation, and red/far red response. In a more preferred embodiment, the photosensitive trait is flowering time, and said flowering time is decreased.

In one aspect, the present invention is drawn to a seed derived from the transgenic plant described above. In a further aspect, the invention is drawn to a plant tissue derived from the transgenic plant described above. Preferably, the plant tissue is a flower.

In one aspect, the present invention is drawn to a transgenic plant having at least one modulated photosensitive trait as compared to a wild-type plant, wherein the transgenic plant includes a recombinant expression vector that produces an inhibitor of a PFT1 gene. In a preferred embodiment, the PFT1 gene includes the nucleotide sequence shown in SEQ ID NO: 2 or SEQ ID NO: 16. In an alternate preferred embodiment, the PFT1 gene includes the nucleotide sequence shown in SEQ ID NO: 2, from nucleotides 1 to 2512. In a preferred embodiment, the expression vector includes a constitutive promoter. In an alternate preferred embodiment, the expression vector includes an inducible promoter.

In a preferred embodiment, the transgenic plant is a plant which is selected from the group including tomato, rice and tobacco plants. In an alternate preferred embodiment, the transgenic plant is *Arabidopsis thaliana*.

In a preferred embodiment, the inhibitor includes an antisense molecule that inhibits the PFT1 gene. In an alternate preferred embodiment, the inhibitor includes a short interfering RNA (siRNA) configured to inhibit the production of a PFT1 gene product.

In a preferred embodiment, the photosensitive trait is a trait selected from the group including flowering time, leaf number, shade avoidance syndrome, stem elongation, and red/far red response. In a more preferred embodiment, the photosensitive trait is flowering time, and the flowering time is increased.

In one aspect, the present invention is drawn to a seed derived from the transgenic plant described above. In another aspect, the present invention is drawn to a plant tissue derived from the transgenic plant described above. In a preferred embodiment, the tissue is a flower.

In another aspect, the present invention includes methods of generating recombinant nucleic acid molecules encoding a PTF1 protein as well as the recombinant nucleic acid molecules produced from such methods. The method includes providing genetic material from a plant and isolating from said nuclear material the nucleic acid molecule encoding a PFT1 protein. In various embodiments, the genetic material may be genomic DNA, RNA, cDNA generated from a plant. In certain embodiments, the genetic material is encompassed in a library, which in certain embodiments may be an expression library. In certain embodiments, the plant may be selected from the group including wheat, barley, rye, oat, flax, millet, corn, tomato, rice and tobacco plants. The nucleic acid molecule may be isolated by any method available to one of ordinary skill in the art. In certain embodiments, the nucleic acid molecule is isolated by hybridization to a PFT1 encoding polynucleotide or fragment thereof. Examples of such isolation include hybridization to amplify the nucleic acid molecule, hybridization to identify the nucleic acid molecule in a library, and hybridization to directly purify the nucleic acid molecule. In another embodiment, the isolation is performed by screening an expression library with an antibody to a PFT1 protein including without limitation the PFT1 proteins disclosed herein.

BRIEF DESCRIPTION OF THE DRAWINGS

FIG. 1A-B. Genomic sequence of PFT1. The PFT1 genomic sequence is shown with upstream and downstream sequences. The numbering is according to BAC F2J7. The sequence corresponds to SEQ ID NO: 1. Exons are underlined. Intron donor and acceptor sites are in bold, italic. Transcription initiation is shown in caps, italic. Start and stop codons are in caps, bold.

FIG. 2. cDNA sequence of PFT1. This sequence corresponds to SEQ ID NO: 2. Start and stop codons are in caps, bold and underlined.

FIG. 3. Protein sequence of PFT1. This sequence corresponds to SEQ D NO: 3.

FIGS. 9A-C. Alignment of PFT1 genes. The alignment of PFT1 genes from five plants using ClustalW (Ver. 1.82) is shown. The genes include rice (OsPFT1) (SEQ ID NO: 17), saccharum officinarum (SoPFT1) (SEQ ID NO: 13), medicago (MtPFT1) (SEQ ID NO: 15), sorghum (SbPFT1) (SEQ ID NO: 14) and *Arabidopsis* (AtPFT1) (SEQ ID NO: 2). Part 1. Alignment scores (% identity) from pairwise comparison of the five sequences and Part 2. alignment of the five sequences.

FIG. 10. Genomic sequence of rice PFT1. The rice PFT1 genomic sequence is shown with upstream and downstream sequences. The numbering is according to BAC OSJNBa0064123. The sequence corresponds to SEQ ID NO: 16. Exons are underlined. Intron donor and acceptor sites are in bold, italic. Transcription initiation is shown in caps, italic. Start and stop codons are in caps, bold.

FIG. 11. Protein sequence of rice PFT1. This sequence corresponds to SEQ ID NO: 17.

DETAILED DESCRIPTION OF THE PREFERRED EMBODIMENT

Figure 4:
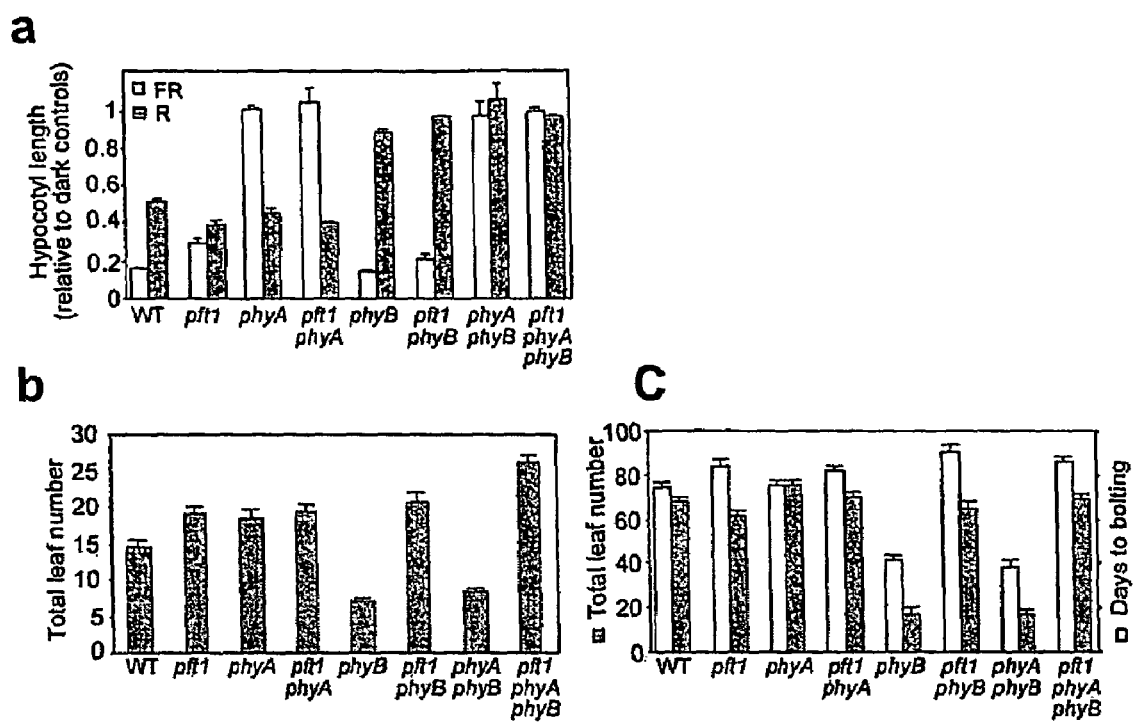
FIG. 4. Phenotypes of pft1, phyA and phyB single, double and triple mutants. a, Hypocotyl length of 5-day-old seedlings of the indicated genotypes grown for 4 days under 3 $\mu$mol/m$^2$ s of far-red-light (FR) or 10 mol/m$^2$ s of red-light (R). b,c Flowering time of the indicated genotypes grown under long days (16 h WL/8h D) (b) and short days (9 h WL/16 h D) (c). Data represent averages of 3 independent experiments (a) and 8-10 plants (b-c)±SE.

Embodiments of the invention are based, in part, upon the identification of an EST clone (APZL03h11R) as a novel gene regulating flowering time in plants corresponding to the PFT1 locus. Thus, one embodiment of the invention provides isolated nucleic acids including nucleotide sequences comprising or derived from the PFT1 genes and/or encoding polypeptides comprising or derived from the PFT1 proteins. PFT1 sequences include the specifically disclosed sequence, and splice variants, allelic variants, synonymous sequences, and homologous or orthologous variants thereof. Thus, for example, embodiments of the invention include genomic and cDNA sequences from the PFT1 gene.

Embodiments of the invention also include allelic variants and homologous or orthologous sequences. For example, these variants are useful in allele specific hybridization screening or PCR amplification techniques. Moreover, subsets of the PFT1 sequence, including both sense and antisense sequences, and both normal and mutant sequences, as well as intronic, exonic and untranslated sequences, may be employed for these techniques. Such sequences may comprise a small number of consecutive nucleotides from the sequence disclosed or otherwise enabled herein but preferably include at least 8-10, and more preferably 9-25, consecutive nucleotides from an PFT1 sequence. Various nucleic acid constructs in which PFT1 sequences, either complete or subsets, are operably joined to exogenous sequences to form cloning vectors, expression vectors, fusion vectors, transgenic constructs, and the like are also contemplated.

The PFT1 mutant was identified in a screening assay for T-DNA activation tagged *Arabidopsis* lines. Accordingly, embodiments of the invention include the PFT1 gene and mutations thereof, as well as a characterization of the PFT1 mutant which has been discovered in *Arabidopsis*. However, the disclosed methods are not limited to any particular plant type. It is expected that similar mutations in other plants will result in similar phenotypes.

Embodiments of the invention also include functional PFT1 polypeptides, and functional fragments thereof. As used herein, the term "functional polypeptide" refers to a polypeptide which possesses biological function or activity which is identified through a defined functional assay and which is associated with a particular biologic, morphologic, or phenotypic alteration in the cell. The term "functional fragments of PFT1 polypeptide", refers to all fragments of PFT1 that retain PFT1 activity, e.g., ability to confer a modulated photosensitive trait such as an altered flowering time and/or leaf number in a plant. Biologically functional fragments, for example, can vary in size from a polypeptide fragment as small as an epitope capable of binding an antibody molecule to a large polypeptide capable of participating in the characteristic induction or programming of phenotypic changes within a cell. "Photosensitive trait" refers to a plant trait that is mediated through one or more light receptors including but not limited to a phytochrome photoreceptor, a cryptochrome photoreceptor, a zt1 receptor, and a phototroping receptor.

Many modifications of the PFT1 primary amino acid sequence may result in plants having reduced or abolished PFT1 responses. Such modifications may be deliberate, as by site-directed mutagenesis, or may be spontaneous. All of the polypeptides produced by these modifications are included herein as long as the biological activity of PFT1 is present. Further, deletion of one or more amino acids can also result in a modification of the structure of the resultant molecule without significantly altering its activity. This can lead to the development of a smaller active molecule which could have broader utility. For example, it may be possible to remove amino or carboxy terminal amino acids required for PFT1 activity.

PFT1 polypeptides include amino acid sequences substantially the same as the sequence set forth in SEQ ID NO: 3 or SEQ ID NO: 17, including mutants that result in plants having altered time to flowering and/or leaf number. The term "substantially the same" refers to amino acid sequences that provide nearly the same amino acid sequence, or retain the activity of PFT1 as described herein. The PFT1 polypeptides of the invention include conservative variations of the polypeptide sequence.

The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

FIG. 9 shows the amino acid sequence alignment of several PF1 proteins. While a number of the amino acid sequences are only partial sequences from various databases, the sequence alignment shows which regions of the protein are more conserved that the others. In addition, one of skill in the art may perform additional sequence alignments using other known methods. Such sequence alignments provide a good indication of the degree of variation of amino acid residues at any given position that may be tolerated. One of skill in the art would understand that highly conserved regions are less likely to tolerate significant variation while less conserved regions are more likely to tolerate variation. Also, one of skill in the art will appreciate that where corresponding residues vary between the sequences, such variation gives an indication of the nature of changes that are likely to be tolerated without disturbing the function of the protein. However, one of skill in the art also will appreciate that some areas such as the C-terminus, while less conserved on an absolute level, have significant motifs that are likely to be functional, such as the glutamine rich region.

PFT1 proteins can be analyzed by standard SDS-PAGE and/or immunoprecipitation analysis and/or Western blot analysis, for example. Embodiments of the invention also provide an isolated polynucleotide sequence encoding a polypeptide having the amino acid sequence of SEQ ID NO: 3 or SEQ ID NO: 17. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences which encode PFT1. It is understood that polynucleotides encoding all or varying portions of PFT1 are included herein, as long as they encode a polypeptide with PFT1 activity. Such polynucleotides include naturally occurring, synthetic, and intentionally manipulated polynucleotides as well as splice variants. For example, portions of the mRNA sequence may be altered due to alternate RNA splicing patterns or the use of alternate promoters for RNA transcription.

Moreover, PFT1 polynucleotides include polynucleotides having alterations in the nucleic acid sequence which still encode a polypeptide having the ability to modulate a photosensitive trait such as the flowering response and/or leaf number. Alterations in PFT1 nucleic acid include but are not limited to intragenic mutations (e.g., point mutation, non-sense (stop), antisense, splice site and frameshift) and heterozygous or homozygous deletions. Detection of such alterations can be done by standard methods known to those of skill in the art including sequence analysis, Southern blot analysis, PCR based analyses (e.g., multiplex PCR, sequence tagged sites (STSs)) and in situ hybridization. Embodiments of the invention also include anti-sense polynucleotide sequences.

The polynucleotides described herein include sequences that are degenerate as a result of the genetic code. There are 20 natural amino acids, most of which are specified by more than one codon. Therefore, all degenerate nucleotide sequences are included in the invention as long as the amino acid sequence of PFT1 polypeptide encoded by such nucleotide sequences retains PFT1 activity. A "functional polynucleotide" denotes a polynucleotide which encodes a functional polypeptide as described herein. In addition, embodiments of the invention also include a polynucleotide encoding a polypeptide having the biological activity of an amino acid sequence of SEQ ID NO: 3 or SEQ ID NO: 17 and having at least one epitope for an antibody immunoreactive with PFT1 polypeptide.

As used herein, the terms "polynucleotides" and "nucleic acid sequences" refer to DNA, RNA and cDNA sequences.

The polynucleotides encoding PFT1 include the nucleotide sequence of SEQ ID NOS: 1, 2, and 16. Genomic DNA sequences are shown in SEQ ID NO: 1 and 16. A cDNA sequence is shown in SEQ ID NO: 2. Nucleic acid sequences complementary to SEQ ID NOS: 1, 2, and 16 are also encompassed within the present invention. A complementary sequence may include an antisense nucleotide. When the sequence is RNA, the deoxyribonucleotides A, G, C, and T of SEQ ID NOS: 1 and 2 and 16 are replaced by ribonucleotides A; G, C, and U, respectively. Also included in the invention are fragments ("probes") of the above-described nucleic acid sequences that are at least 15 bases in length, which is sufficient to permit the probe to selectively hybridize to DNA that encodes the protein of SEQ ID NO: 3 or SEQ ID NO: 17.

"Antisense" nucleic acids are DNA or RNA molecules that are complementary to at least a portion of a specific mRNA molecule (Weintraub, *Scientific American* 262 40, 1990). In the cell, the antisense nucleic acids hybridize to the corresponding mRNA, forming a double-stranded molecule. This interferes with the translation of the mRNA since the cell will not translate a mRNA that is double-stranded. Antisense oligomers of about 15 nucleotides are preferred, since they are easily synthesized and are less likely to cause non-specific interference with translation than larger molecules. The use of antisense methods to inhibit the in vitro translation of genes is well known in the art (Marcus-Sakura *Anal. Biochem.* 172: 289, 1998). In the present case, plants transformed with constructs containing antisense fragments of the PFT1 gene would display a modulated photosensitive phenotype such as altered time to flowering.

Long double-stranded RNAs (dsRNAs; typically >200 nt) can be used to silence the expression of target genes in plants and plant cells. Upon introduction, the long dsRNAs enter the RNA interference (RNAi) pathway which involves the production of short (20-25 nucleotide) small interfering RNAs (siRNAs) and assembly of the siRNAs into RNA-induced silencing complexes (RISCs). The siRNA strands are then unwound to form activated RISCs which cleave the target RNA. Double stranded RNA has been shown to be extremely effective in silencing a target RNA. Introduction of double stranded RNA corresponding to the PFT1 gene would be expected to modify the photosensitive phenotypes discussed herein including, but not limited to, flowering time, leaf number and stem length.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 ng/ml sheared and denatured salmon sperm DNA. Hybridization could occur under medium stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art. "Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes related from unrelated PFT1 nucleotide sequences.

In another aspect of the invention, very high stringency hybridization conditions can include at least one wash at 0.1×SSC, 0.1% SDS, at 60° C. for 15 minutes. High stringency hybridization conditions can include at least one wash at 0.2×SSC, 0.1% SDS, at 60° C. for 15 minutes. Moderate stringency hybridization conditions can include at least one wash at 0.5×SSC, 0.1% SDS, at 60° C. for 15 minutes. Low stringency hybridization conditions can include at least one wash at 1.0×SSC, 0.1% SDS, at 60° C. for 15 minutes.

Another aspect of the invention is polypeptides or fragments thereof which have at least about 70%, at least about 80%, at least about 85%, at least about 90%, at least about 95%, or more than about 95% homology to SEQ ID NO: 3 or SEQ ID NO: 17, and sequences substantially identical thereto, or a fragment comprising at least 5, 10, 15, 20, 25, 30, 35, 40, 50, 75, 100, or 150 consecutive amino acids thereof. Homology may be determined using any of the methods described herein which align the polypeptides or fragments being compared and determines the extent of amino acid identity or similarity between them. It will be appreciated that amino acid "homology" includes conservative amino acid substitutions such as those described above.

The polypeptides or fragments having homology to SEQ ID NO: 3 or SEQ ID NO: 17, and sequences substantially identical thereto, or a fragment comprising at least about 5, 10, 15, 20, 25, 30, 35, 40, 50, 75, 100, or 150 consecutive amino acids thereof may be obtained by isolating the nucleic acids encoding them using the techniques described herein.

Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to the polypeptide of SEQ ID NO: 3 or SEQ ID NO: 17, and sequences substantially identical thereto, or a fragment comprising at least about 5, 10, 15, 20, 25, 30, 35, 40, 50, 75, 100, or 150 consecutive amino acids thereof using any of the programs described above.

Also included in embodiments of the invention are nucleotide sequences that are greater than 70% homologous with SEQ ID NOS: 1 or 2 or 16, but still retain the ability to modulate a photosensitive trait such as an altered time to flowering. Other embodiments of the invention include nucleotide sequences that are greater than 75%, 80%, 85%, 90% or 95% homologous with SEQ ID NOS: 1 or 2 or 16, but still retain the ability to confer a modulated photosensitive phenotype which includes altered time to flowering.

Specifically disclosed herein is a cDNA sequence for PFT1, as well as two genomic DNA sequences. DNA sequences of the invention can be obtained by several methods. For example, the DNA can be isolated using hybridization or computer-based techniques which are well known in the art. Such techniques include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library.

Screening procedures which rely on nucleic acid hybridization make it possible to isolate any gene sequence from any organism, provided the appropriate probe is available. Oligonucleotide probes, which correspond to a part of the PFT1 sequence encoding the protein in question, can be synthesized chemically. This requires that short, oligopeptide stretches of the amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.* 9, 879, 1981). Alternatively, a subtractive library is useful for elimination of non-specific cDNA clones.

Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al. *Nucl. Acid Res.*, 11, 2325, 1983).

A cDNA expression library, such as lambda gt11, can be screened indirectly for PFT1 peptides using antibodies specific for PFT1. Such antibodies can be either polyclonally or monoclonally derived and used to detect expression product indicative of the presence of PFT1 cDNA.

Another embodiment of the invention relates to plants that have at least one modulated photosensitive trait. Such modifications might include an altered red/far red response which refers to the response of a plant to red and far red light. "Red/far red response" is mediated through phytochromes which exist in two interconvertible forms: $P_R$ absorbs red (about 660 nm) light and $P_{FR}$ which absorbs far red (about 730 nm) light. Thus, a red/far red response is a plant response mediated by a phytochrome. Phytochrome mediates a wide variety of responses including shade avoidance syndrome. "Shade avoidance syndrome" refers to a series of responses triggered in crowded or shaded environments by a decrease in the red/far-red ratio of incoming light reaching the plants and includes the promotion of stem elongation and acceleration of flowering.

Specific modifications include transgenic plants with an altered time to flowering or an altered leaf number due to transformation with constructs using antisense or siRNA technology that affect transcription or expression from the PFT1 gene. Such plants exhibit an altered time to flowering and leaf number. "Flowering time" refers to the number of days to flower. Some plants germinate better if seeds are cold treated. The plants are then moved to growing conditions and this is taken as time 0 for determination of time to flowering. If there is no pre-treatment, then time 0 starts at planting. Both increases and decreases in time to flowering are encompassed herein.

Accordingly, in another series of embodiments, the present invention provides methods of screening or identifying proteins, small molecules or other compounds which are capable of inducing or inhibiting the expression of the PFT1 genes and proteins. The assays may be performed in vitro using transformed or non-transformed cells, immortalized cell lines, or in vivo using transformed plant models enabled herein. In particular, the assays may detect the presence of increased or decreased expression of PFT1 (from *Arabidopsis* or other plants) genes or proteins on the basis of increased or decreased mRNA expression, increased or decreased levels of PFT1 protein products, or increased or decreased levels of expression of a marker gene (e.g., beta-galactosidase, green fluorescent protein, alkaline phosphatase or luciferase) operably joined to an PFT15' regulatory region in a recombinant construct. Cells known to express a particular PFT1, or transformed to express a particular PFT1, are incubated and one or more test compounds are added to the medium. After allowing a sufficient period of time (e.g., 0-72 hours) for the compound to induce or inhibit the expression of PFT1, any change in levels of expression from an established baseline may be detected using any of the techniques described above.

In another series of embodiments, the present invention provides methods for identifying proteins and other compounds which bind to, or otherwise directly interact with, the PFT1. The proteins and compounds include endogenous cellular components which interact with PFT1 in vivo and which, therefore, provide new targets for agricultural products, as well as recombinant, synthetic and otherwise exogenous compounds which may have PFT1 binding capacity and, therefore, are candidates for modulating photosensitive traits. Thus, in one series of embodiments, High Throughput Screening-derived proteins, DNA chip arrays, cell lysates or tissue homogenates may be screened for proteins or other compounds which bind to one of the normal or mutant PFT1 genes. Alternatively, any of a variety of exogenous compounds, both naturally occurring and/or synthetic (e.g., libraries of small molecules or peptides), may be screened for PFT1 binding capacity.

In each of these embodiments, an assay is conducted to detect binding between PFT1 and another moiety. The PFT1 in these assays may be any polypeptide comprising or derived from a normal or mutant PFT1 protein, including functional domains or antigenic determinants of PFT1. Binding may be detected by non-specific measures (e.g., transcription modulation, altered chromatin structure, peptide production or changes in the expression of other downstream genes which can be monitored by differential display, 2D gel electrophoresis, differential hybridization, or SAGE methods) or by direct measures such as immunoprecipitation, the Biomolecular Interaction Assay (BIAcore) or alteration of protein gel electrophoresis. The preferred methods involve variations on the following techniques: (1) direct extraction by affinity chromatography; (2) co-isolation of PFT1 components and bound proteins or other compounds by immunoprecipitation; (3) BIAcore analysis; and (4) the yeast two-hybrid systems.

Embodiments of the invention also include methods of identifying proteins, small molecules and other compounds capable of modulating the activity of normal or mutant PFT1. Using normal cells or plants, the transformed cells and plant models of the present invention, or cells obtained from subjects bearing normal or mutant PFT1 genes, the present invention provides methods of identifying such compounds on the basis of their ability to affect the expression of PFT1, the activity of PFT1, the activity of other PFT1-regulated genes, the activity of proteins that interact with normal or mutant PFT1 proteins, the intracellular localization of the PFT1, changes in transcription activity, the presence or levels of membrane bound PFT1, or other biochemical, histological, or physiological markers which distinguish cells bearing normal and modulated PFT1 activity in plants.

In accordance with another aspect of the invention, the proteins of the invention can be used as starting points for rational chemical design to provide ligands or other types of small chemical molecules. Alternatively, small molecules or other compounds identified by the above-described screening assays may serve as "lead compounds" in design of modulators of photosensitive traits in plants.

DNA sequences encoding PFT1 can be expressed in vitro by DNA transfer into a suitable host cell. "Host cells" are cells in which a vector can be propagated and its DNA expressed. The term also includes any progeny or graft material, for example, of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

As part of the present invention, the PFT1 polynucleotide sequences may be inserted into a recombinant expression vector. The terms "recombinant expression vector" or "expression vector" refer to a plasmid, virus or other vehicle known in the art that has been manipulated by insertion or incorporation of the PFT1 genetic sequence. Such expression vectors contain a promoter sequence which facilitates the efficient transcription of the inserted PFT1 sequence. The expression vector typically contains an origin of replication, a promoter, as well as specific genes which allow phenotypic selection of the transformed cells.

Methods which are well known to those skilled in the art can be used to construct expression vectors containing the PFT1 coding sequence and appropriate transcriptional/translational control signals. These methods include in vitro recombinant DNA techniques, synthetic techniques, and in vivo recombination/genetic techniques.

A variety of host-expression vector systems may be utilized to express the PFT1 coding sequence. These include but are not limited to microorganisms such as bacteria transformed with recombinant bacteriophage DNA, plasmid DNA or cosmid DNA expression vectors containing the PFT1 coding sequence; yeast transformed with recombinant yeast expression vectors containing the PFT1 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the PFT1 coding sequence; insect cell systems infected with recombinant virus expression vectors (e.g., baculovirus) containing the PFT1 coding sequence; or animal cell systems infected with recombinant virus expression vectors (e.g., retroviruses, adenovirus, vaccinia virus) containing the PFT1 coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see e.g., Bitter et al. *Methods in Enzymology* 153, 516-544, 1987). For example, when cloning in bacterial systems, inducible promoters such as pL of bacteriophage γ, plac, ptrp, ptac (tp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted PFT1 coding sequence.

Isolation and purification of recombinantly expressed polypeptide, or fragments thereof, may be carried out by conventional means including preparative chromatography and immunological separations involving monoclonal or polyclonal antibodies.

In another embodiment, embodiments of the invention provide a method for producing a genetically modified plant having at least one modulated photosensitive trait such as having an altered time to flowering as compared to a plant which has not been genetically modified (e.g., a wild-type plant). The method includes the steps of contacting a plant cell with at least one vector containing at least one nucleic acid sequence encoding an PFT1 gene or a mutant, homolog or fragment thereof, wherein the nucleic acid sequence is operably associated with a promoter, to obtain a transformed plant cell; producing a plant from the transformed plant cell; and thereafter selecting a plant exhibiting a modulated photosensitive trait such as an altered time to flowering.

Transgenic plants that result in at least one modulated photosensitive trait such as an altered time to flowering may be obtained by reduced expression of the PFT1 gene. Thus, one embodiment of the invention includes plants transformed with antisense polynucleotides complementary to the PFT1 gene or fragments thereof wherein production of the antisense polynucleotides results in reduced expression of the PFT1 gene. In an alternate embodiment, reduced expression of PFT1 may also be achieved by methods such as cosuppression (Hooper, C. *J. NIH Res.* 3, 49-54, 1991) by operatively linking a truncated form of an PFT1 gene to a promoter. In an alternate embodiment, transgenic plants overexpressing the PFT1 gene are described. Such plants might be expected to display a modulated photosensitive trait such as an altered time to flowering.

The term "genetic modification" as used herein refers to the introduction of one or more heterologous nucleic acid sequences, e.g., an PFT1 or an PFT1 mutant encoding sequence, into one or more plant cells, which can generate whole, sexually competent, viable plants. The term "genetically modified" as used herein refers to a plant which has been generated through the aforementioned process. Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete producing cells, and cells which regenerate into whole plants. Accordingly, a seed comprising multiple plant cells capable of regenerating into a whole plant, is included in the definition of "plant cell".

As used herein, the term "plant" refers to either a whole plant, a plant part, a plant cell, or a group of plant cells, such as plant tissue, for example. Plantlets are also included within the meaning of "plant". Plants included in the invention are any plants amenable to transformation techniques, including angiosperms, gymnosperms, monocotyledons and dicotyledons.

Examples of monocotyledonous plants include, but are not limited to, asparagus, field and sweet corn, barley, wheat, rice, sorghum, onion, pearl millet, rye and oats. Examples of dicotyledonous plants include, but are not limited to tomato, tobacco, cotton, potato, rapeseed, field beans, soybeans, peppers, lettuce, peas, alfalfa, clover, cole crops or *Brassica oleracea* (e.g., cabbage, broccoli, cauliflower, brussels sprouts), radish, carrot, beets, eggplant, spinach, cucumber, squash, melons, cantaloupe, sunflowers and various ornamentals. Woody species include poplar, pine, sequoia, cedar, oak, etc.

The term "exogenous nucleic acid sequence" as used herein refers to a nucleic acid foreign to the recipient plant host or, native to the host if the native nucleic acid is substantially modified from its original form. For example, the term includes a nucleic acid originating in the host species, where such sequence is operably linked to a promoter that differs from the natural or wild-type promoter. In one embodiment, at least one nucleic acid sequence encoding PFT1 or a variant thereof is operably linked with a promoter. It may be desirable to introduce more than one copy of an PFT1 polynucleotide into a plant for enhanced expression. For example, multiple copies of the gene would have the effect of increasing production of the PFT1 gene product in the plant.

Genetically modified plants of the present invention are produced by contacting a plant cell with a vector including at least one nucleic acid sequence encoding a PFT1 or a variant thereof. To be effective once introduced into plant cells, the PFT1 nucleic acid sequence is operably associated with a promoter which is effective in the plant cell to cause transcription of PFT1. Additionally, a polyadenylation sequence or transcription control sequence, also recognized in plant cells may also be employed. It is preferred that the vector harboring the nucleic acid sequence to be inserted also contain one or more selectable marker genes so that the transformed cells can be selected from non-transformed cells in culture, as described herein.

The term "operably linked" refers to functional linkage between a promoter sequence and a nucleic acid sequence regulated by the promoter. The operably linked promoter controls the expression of the nucleic acid sequence.

The expression of structural genes may be driven by a number of promoters. Although the endogenous, or native promoter of a structural gene of interest may be utilized for transcriptional regulation of the gene, preferably, the promoter is a foreign regulatory sequence. For plant expression vectors, suitable viral promoters include the 35S RNA and 19S RNA promoters of CaMV (Brisson, et al. *Nature,* 310, 511, 1984; and Odell, et al. *Nature,* 313, 810, 1985); the full-length transcript promoter from Figwort Mosaic Virus (FMV) (Gowda, et al. *J. Cell Biochem.* 13D, 301, 1989) and the coat protein promoter to TMV (Takamatsu, et al. *EMBO J.* 6, 307, 1987). Alternatively, plant promoters such as the light-inducible promoter from the small subunit of ribulose bisphosphate carboxylase (ssRUBISCO) (Coruzzi, et al. *EMBO J.* 3, 1671, 1984; and Broglie, et al., *Science* 224, 838, 1984); mannopine synthase promoter (Velten, et al. *EMBO J.* 3, 2723, 1984) nopaline synthase (NOS) and octopine synthase (OCS) promoters (carried on tumor-inducing plasmids of *Agrobacterium tumefaciens*) or heat shock promoters, e.g., soybean hspl7.5-E or hspl7.3-B (Gurley, et al. *Mol. Cell. Biol.* 6, 559, 1986; and Severin, et al. *Plant Mol. Biol.* 15, 827, 1990) may be used.

Promoters useful in the invention include both natural constitutive and inducible promoters as well as engineered promoters. The CaMV promoters are examples of constitutive promoters. To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Meft, et al. *Proc. Natl. Acad. Sci., U.S.A.* 90, 4567, 1993); In2-1 and In2-2 regulator sequences which are activated by substituted benzenesulfonamides, e.g., herbicide safeners (Hershey, et al. *Plant Mol. Biol.* 17, 679, 1991); and the GRE regulatory sequences which are induced by glucocorticoids (Schena, et al. *Proc. Natl. Acad. Sci., U.S.A.* 88, 10421, 1991). Other promoters, both constitutive and inducible will be known to those of skill in the art.

The particular promoter selected should be capable of causing sufficient expression to result in the production of an effective amount of structural gene product to modulate a photosensitive trait such as flowering. The promoters used in the vector constructs of the present invention may be modified, if desired, to affect their control characteristics.

Tissue specific promoters may also be utilized in the present invention. An example of a tissue specific promoter is the promoter active in shoot meristems (Atanassova, et al. *Plant J.* 2, 291, 1992). Other tissue specific promoters useful in transgenic plants, including the cdc2a promoter and cyc07 promoter, will be known to those of skill in the art. (See for example, Ito, et al. *Plant Mol. Biol.* 24, 863, 1994; Martinez, et al. *Proc. Natl. Acad. Sci. USA* 89, 7360, 1992; Medford, et al. *Plant Cell* 3, 359, 1991; Terada, et al. *Plant Journal* 3, 241, 1993; Wissenbach, et al. *Plant Journal* 4, 411, 1993).

Optionally, a selectable marker may be associated with the nucleic acid sequence to be inserted. As used herein, the term "marker" refers to a gene encoding a trait or a phenotype which permits the selection of, or the screening for, a plant or plant cell containing the marker. Preferably, the marker gene is an antibiotic resistance gene whereby the appropriate antibiotic can be used to select for transformed cells from among cells that are not transformed. Examples of suitable selectable markers include adenosine deaminase, dihydrofolate reductase, hygromycin-B-phospho-transferase, thymidine kinase, xanthine-guanine phospho-ribosyltransferase and aminoglycoside 3'-O-phospho-transferase II (kanamycin, neomycin and G418 resistance). Other suitable markers will be known to those of skill in the art.

Vector(s) employed in the present invention for transformation of a plant cell include a nucleic acid sequence encoding PFT1, operably linked to a promoter. To commence a transformation process in accordance with the present invention, it is first necessary to construct a suitable vector and properly introduce it into the plant cell. Details of the construction of vectors utilized herein are known to those skilled in the art of plant genetic engineering.

PFT1 nucleic acid sequences utilized in the present invention can be introduced into plant cells using Ti plasmids of *Agrobacterium tumefaciens*, root-inducing (Ri) plasmids, and plant virus vectors. (For reviews of such techniques see, for example, Weissbach & Weissbach, *Methods for Plant Molecular Biology*, Academic Press, NY, Section VIII, pp. 421463, 1988; and Grierson & Corey, *Plant Molecular Biology*, 2d Ed., Blackie, London, Ch. 7-9, 1998; and Horsch, et al. *Science,* 227, 1229, 1985, both incorporated herein by reference). In addition to plant transformation vectors derived from the Ti or root-inducing (Ri) plasmids of *Agrobacterium*, alternative methods may involve, for example, the use of liposomes, electroporation, chemicals that increase free DNA uptake, transformation using viruses or pollen and the use of microprojection.

One of skill in the art will be able to select an appropriate vector for introducing the PFT1-encoding nucleic acid sequence in a relatively intact state. Thus, any vector which will produce a plant carrying the introduced DNA sequence should be sufficient. Even use of a naked piece of DNA would be expected to confer the properties of this invention, though at low efficiency. The selection of the vector, or whether to use a vector, is typically guided by the method of transformation selected.

The transformation of plants in accordance with the invention may be carried out in essentially any of the various ways known to those skilled in the art of plant molecular biology. (See, for example, *Methods of Enzymology*, Vol. 153, 1987, Wu and Grossman, Eds., Academic Press, incorporated herein by reference). As used herein, the term "transformation" means alteration of the genotype of a host plant by the introduction of an PFT1 or PFT1 mutant nucleic acid sequence.

For example, an PFT1 nucleic acid sequence can be introduced into a plant cell utilizing *Agrobacterium tumefaciens* containing the Ti plasmid, as mentioned briefly above. In using an *A. tumefaciens* culture as a transformation vehicle, it is most advantageous to use a non-oncogenic strain of *Agrobacterium* as the vector carrier so that normal non-oncogenic differentiation of the transformed tissues is possible. It is also preferred that the *Agrobacterium* harbor a binary Ti plasmid system. Such a binary system comprises 1) a first Ti plasmid having a virulence region essential for the introduction of transfer DNA (T-DNA) into plants, and 2) a chimeric plasmid. The latter contains at least one border region of the T-DNA region of a wild-type Ti plasmid flanking the nucleic acid to be transferred. Binary Ti plasmid systems have been shown effective to transform plant cells (De Framond, *Biotechnology*, 1, 262, 1983; Hoekema, et al., *Nature,* 303, 179, 1983). Such a binary system is preferred because it does not require integration into the Ti plasmid of *Agrobacterium*, which is an older methodology.

Methods involving the use of *Agrobacterium* in transformation according to the present invention include, but are not limited to: 1) co-cultivation of *Agrobacterium* with cultured isolated protoplasts; 2) transformation of plant cells or tissues with *Agrobacterium*; or 3) transformation of seeds, apices or meristems with *Agrobacterium*.

In addition, gene transfer can be accomplished by in planta transformation by *Agrobacterium*, as described by Bechtold, et al., (C. R. Acad. Sci. Paris, 316:1194, 1993). This approach is based on the vacuum infiltration of a suspension of *Agrobacterium* cells.

One method of introducing PFT1-encoding nucleic acid into plant cells is to infect such plant cells, an explant, a meristem or a seed, with transformed *Agrobacterium tumefaciens* as described above. Under appropriate conditions known in the art, the transformed plant cells are grown to form shoots, roots, and develop further into plants.

Alternatively, PFT1 encoding nucleic acid sequences can be introduced into a plant cell using mechanical or chemical means. For example, the nucleic acid can be mechanically transferred into the plant cell by microinjection using a micropipette. Alternatively, the nucleic acid may be transferred into the plant cell by using polyethylene glycol which forms a precipitation complex with genetic material that is taken up by the cell.

PFT1 nucleic acid sequences can also be introduced into plant cells by electroporation (Fromm, et al., Proc. Natl. Acad. Sci., U.S.A., 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing PFT1 nucleic acid into a plant cell is high velocity ballistic penetration by small particles with the nucleic acid to be introduced contained either within the matrix of such particles, or on the surface thereof (Klein, et al., Nature 327:70, 1987). Bombardment transformation methods are also described in Sanford, et al. (Techniques 3:3-16, 1991) and Klein, et al. (Bio/Techniques 10:286, 1992). Although, typically only a single introduction of a new nucleic acid sequence is required, this method particularly provides for multiple introductions.

Cauliflower mosaic virus (CaMV) may also be used as a vector for introducing nucleic acid into plant cells (U.S. Pat. No. 4,407,956). CaMV viral DNA genome is inserted into a parent bacterial plasmid creating a recombinant DNA molecule which can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants.

As used herein, the term "contacting" refers to any means of introducing PFT1 into the plant cell, including chemical and physical means as described above. Preferably, contacting refers to introducing the nucleic acid or vector into plant cells (including an explant, a meristem or a seed), via *Agrobacterium tumefaciens* transformed with the PFT1 encoding nucleic acid as described above.

Normally, a plant cell is regenerated to obtain a whole plant from the transformation process. The immediate product of the transformation is referred to as a "transgenote". The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species of plants, but generally a suspension of protoplasts is first made. In certain species, embryo formation can then be induced from the protoplast suspension, to the stage of ripening and germination as natural embryos. The culture media will generally contain various amino acids and hormones, necessary for growth and regeneration. Examples of hormones utilized include auxins and cytokinins. It is sometimes advantageous to add glutamic acid and proline to the medium, especially for plant species such as corn and alfalfa. Efficient regeneration will depend on the medium, on the genotype, and on the history of the culture. If these variables are controlled, regeneration is reproducible.

Regeneration also occurs from plant callus, explants, organs or parts. Transformation can be performed in the context of organ or plant part regeneration. (see Methods in Enzymology, Vol. 118 and Klee, et al., Annual Review of Plant Physiology, 38:467, 1987). Utilizing the leaf disk-transformation-regeneration method of Horsch, et al., Science, 227:1229, 1985, disks are cultured on selective media, followed by shoot formation in about 24 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by utilizing cuttings or tissue culture techniques to produce multiple identical plants. Selection of desirable transgenotes is made and new varieties are obtained and propagated vegetatively for commercial use.

In seed propagated crops, the mature transgenic plants can be self crossed to produce a homozygous inbred plant. The resulting inbred plant produces seed containing the newly introduced foreign gene(s). These seeds can be grown to produce plants that would produce the selected phenotype, e.g. altered time to flowering.

Parts obtained from regenerated plant, such as flowers, seeds, leaves, branches, roots, fruit, and the like are included in the invention, provided that these parts comprise cells that have been transformed as described. Progeny and variants, and mutants of the regenerated plants are also included within the scope of the invention, provided that these parts comprise the introduced nucleic acid sequences.

Plants exhibiting a modulated photosensitive trait such as an altered time to flowering or an altered leaf number as compared with wild-type plants can be selected by visual observation. The invention includes plants produced by the method of the invention, as well as plant tissue and seeds. Stem elongation may be observed visually or preferably may be determined quantitatively by measuring with a ruler or with a video-imaging system.

In yet another embodiment, the invention provides a method for producing a genetically modified plant cell such that a plant produced from the cell has a modulated photosensitive trait such as an altered time to flowering compared with a wild-type plant. The method includes contacting the plant cell with an PFT1 nucleic acid sequence to obtain a transformed plant cell; growing the transformed plant cell under plant forming conditions to obtain a plant having a modulated photosensitive trait such as an altered time to flowering. Conditions such as environmental and promoter inducing conditions vary from species to species, but should be the same within a species.

It will be understood by those of skill in the art that numerous and various modifications can be made without departing from the spirit of the present invention. A more complete understanding can be obtained by reference to the following specific examples which are provided herein for purposes of illustration only and are not intended to limit the scope of the invention.

EXAMPLES

Example 1

Plant Material and Growth Conditions

Except when stated otherwise, all experiments were done in the Columbia accession. The alleles for the different mutants used were phyA211 and phyB9. FT and CO overexpression lines were a gift of Detlef Weigel. Seeds were sterilized using chlorine in a vapor phase. For RNA extraction, total seedlings grown in MS media without sucrose or shoots from mature plants grown on soil were used. For hypocotyl measurements, seedlings were grown in water-agar medium. R and FR-light treatments were done in LED chambers (Percival Scientific) at 23° C. WL sources were always from fluorescent tubes, 40-70 $\mu mol/m^2$ s for LD and SD respectively, except for incandescent light extensions (LI) with 2 $\mu mol/m^2$ s of PAR (400-700 nm).

For the genetic screen, T-DNA activation-tagged lines were obtained from the *Arabidopsis* Stock Center as pools representing around 100 lines each. Each pool was plated on water agar medium, and stratified for 3 days. Germination was induced by 1 h WL and then every 24 h seedlings received 5 min of R. At the $4^{th}$ day seedlings were scored for signs of de-etiolation, such as shorter hypocotyls or partially opened cotyledons, and transplanted to soil to score adult phenotypes.

Example 2

Molecular Characterization of PFT1

Genomic DNA was extracted from pft1 mutants, cut with HindIII and EcoRI for right border rescue and with BamHI and SpeI for left border rescue, ligated and electroporated into SURE competent cells (Stratagene). Genomic DNA was successfully rescued with HindIII, BamHI and SpeI restriction enzymes. Specific oligonucleotides were designed to detect by PCR the T-DNA insertion in hemizygous and homozygous lines. The following 3 primers were used in PCR:

```
5'CAGAGGAACCCTGTTTCTACTGTTGAGCT3',   (SEQ ID NO: 4)

5'CGTTACTTGGTTGAGCTTGGCCTGAAGGA3'    (SEQ ID NO: 5)
and

5'TCCCGGACATGAAGCCATTTATATGTA3'.     (SEQ ID NO: 6)
```

The expected PCR products were 563 bp for the WT and 491 bp for the mutant, while both bands were detected in hemizygotes.

The T-DNA co-segregated with the pft1 mutation in 140 chromosomes analyzed. 36 F3 populations were tested and it was noted that the Basta resistance (conferred by the T-DNA) also co-segregated with the pft1 mutation. Southern blot data and the rescued genomic DNA sequence agreed with a single insertion on BAC F2J7 from chromosome 1. The genomic sequence is shown in FIG. 1 (SEQ ID NO: 1).

Intron-exon junctions were derived by comparison with EST clone APZL03h11R (Genbank accession# AV528220). RACE-PCR was performed using the GeneRacer kit according to the manufacturer instructions (Invitrogen)

The genomic PFT1 clone was subcloned from BAC F2J7 in two consecutive steps into binary plasmid pPZP212, finally as a PstI-SacI 8.5 kb fragment and introduced into pft1 mutants by transformation with *Agrobacterium tumefaciens* (Clough, et al. *Plant J* 16, 735-43 (1998)). Transgenic lines were selected on MS media supplemented with 50 µg/ml of kanamycin, screened for single locus insertions in the T2 generation and the homozygous lines from the T3 generation used for physiological experiments.

To make the GFP fusion proteins, EcoRI sites were introduced in frame right before the ATG start codon (for GFP-PFT1 fusions) and right before the TAA stop codon (for PFT1-GFP fusions). PCR amplified GFP coding region was subcloned into these EcoRI sites and final constructs confirmed by sequencing before being used for plant transformation as described above.

To assess a phenotype of overexpression, the PFT1 cDNA (FIG. 2; SEQ ID NO: 2) was subcloned in two steps as a BamHI-PstI-PstI fragment into CHF1 and CHF3 plasmids under the 35S constitutive promoter. FIG. 2 shows the sequence of the cDNA. The predicted protein sequence is shown in FIG. 3 (SEQ ID NO: 3). After plant transformation, lines were selected on kanamycin (CHF3 derived plasmids) or gentamycin (70 µg/ml CHF1 derived plasmids).

Example 3 mRNA Quantitation

Specific mRNAs were extracted and quantified by RT-PCR, essentially as described (Blazquez, et al. *Plant Physiol.* 120, 1025-32 (1999)). mRNA was reverse transcribed using the 1$^{st}$ cDNA synthesis kit according to the manufacturer instructions (Invitrogen). Primers, annealing temperatures and the size of PCR products expected were as follows:

```
                                          (SEQ ID NO: 7)
FT, 5' GCTACAACTGGAACAACCTTTGGCAAT 3', (SEQ ID NO: 8)
5' TATAGGCATCATCACCGTTCGTTACTC3';
63° C., 365 bp;

(SEQ ID NO: 9)
CO, 5' AAACTCTTTCAGCTCCATGACCACTACT 3', (SEQ ID NO: 10)
5' CCATGGATGAAATGTATGCGTTATGGTTA 3',
62° C.,453 bp;

(SEQ ID NO: 11)
UBQ10, 5' GGTGTCAGAACTCTCCACCTCAAGAGTA 3', (SEQ ID NO: 12)
5' TCAATTCTCTCTACCGTGATCAAGATGCA 3',
64° C., 318 bp.
```

In all cases at least one of the primers used for PCR spanned intron-exon junctions and amplification of genomic DNA was undetectable in non-retrotranscribed controls. PCR products were detected by southern blot using standard methodology and quantified using a phosporimager (Molecular Dynamics) in the exponential range of amplification.

Example 4

Phenotypes of pft1, phyA and phyB Single, Double and Triple Mutants

Consistent with a role in phytochrome signaling, pft1 mutants displayed small but significant effects on hypocotyl length inhibition under both R and FR-light (FIG. 4a). pft1 mutants were hypo-responsive to FR and hyper-responsive to R. These altered responses to light required functional phyA and phyB, suggesting that PFT1 acts in both the phyA and phyB signaling pathways in seedlings.

pft1 mutants displayed a late flowering phenotype when grown under long-day conditions (LD, 16 hr light/8 hr dark) (FIG. 4b). phyA and phyB regulate flowering time in opposing ways. phyB acts to delay flowering in both LD and short day (SD, 9 hr light/16 hr dark), while phyA weakly promotes flowering, mainly in LD. Flowering time was measured under both LD and SD conditions in pft1, pft1 phyB, and pft1 phyA mutants, and the results were compared to phyB and phyA single mutants (FIGS. 4b, c). pft1 suppressed the early flowering time of suppressed the early flowering time of phyB mutants in both LD and SD conditions independently of phyA, strongly suggesting the PFT1 is essential for phyB regulation of flowering time. pft1 suppression of phyB was specific for flowering, as the increased petiole length characteristic of phyB mutants was largely unaffected in the pft1 phyB double mutant. Note that in phyB and phyA phyB, the apical meristem is already converted to an inflorescence meristem while no sign of change is observed in the pft1 background. The effects of phyA and pft1 mutations in delaying flowering under LD were not additive suggesting that pft1 acts also downstream of phyA. This was further tested using extended photoperiods with low incandescent light (9 h WL/7 h LI/8 h D) where phyA is the main photoreceptor inducing flowering. Under these conditions, phyA, pft1 and phyApft1 double mutants showed a similar delay in flowering time, flier supporting a role for PFT1 in phyA signaling (total leaf number; WT: 9.67±0.72; phyA: 52.5±10.1; pft1: 43±5.51; phyApft1: 56±8.95; average±SE of 9 plants).

Example 5

Molecular Characterization of PFT1

Figure 5:
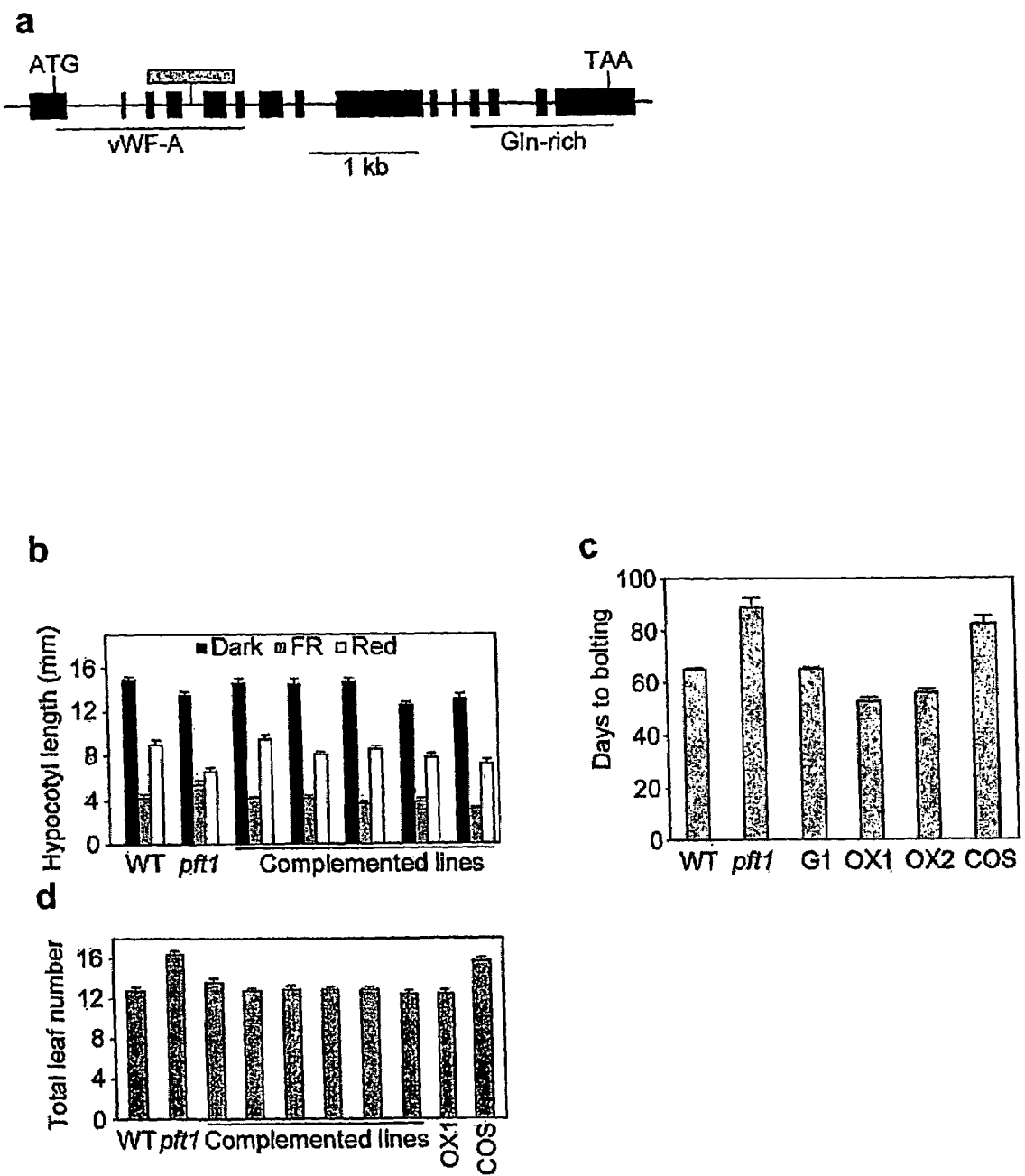
FIG. 5. Molecular characterization of PFT1. a, structure of the PFT1 gene, black boxes represent exons and lines introns. Predicted domains and the T-DNA insertion (out of scale) are indicated. Scale bar=1 kb. b, c, d, Molecular complementation of the hypocotyl length phenotype (b), late flowering phenotype in long days (c) and delayed bolting in short days (d). Different transgenic lines for the PFT1 gene were used, as indicated. OX1 and OX2 are 35S—PFT1 overexpressor lines in pft1 and WT backgrounds, respectively, COS a cosuppressed line in pft1 background and G1 a complemented line.

To characterize PFT1 at the molecular level, the gene which had been tagged with a T-DNA insertion was cloned. The insertion produced a 29 bp deletion and localized within the transcription unit of a predicted gene. The gene structure was derived from the sequence of the EST clone APZL03h11R (Genbank # AV528220) and the 5' end was confirmed by RACE-PCR. It was concluded from this analysis that PFT1 is a single copy gene with 15 exons (FIG. 5a). The predicted protein has 836 amino acids, a predicted vWFA (von Willebrand factor type A) domain in the N-terminus and a Gln rich region in the carboxy-terminus, reminiscent of some transcriptional activators (FIG. 5a). vWFA domains are widely distributed among all phyla (Ponting, et al. *J Mol Biol* 289, 729-45 (1999)). They are involved in various cellular processes and a high proportion have a divalent cation binding site that in some cases has been shown to mediate protein-protein interactions (Hinshelwood, et al. *J Mol Biol* 298, 135-47 (2000)). The DxSxS motif involved in coordination with a divalent cation is converted to ExSxA in PFT1. It is unclear whether this partially conserved motif can still bind a metal.

The expected PFT1 mRNA is about 3 kb in length, consistent with the single band detected in northern blots. In pft1 mutants, a lower molecular weight mRNA species was observed. RACE-PCR was used to further characterize this form and found that it corresponds to a 2.5 kb truncated form of PFT1, that initiates within the T-DNA. This suggests that the 35S enhancers in the right border of the T-DNA initiate transcription within the gene. To confirm that the T-DNA insertion was the basis for the pft1 phenotype, the seedling (FIG. 5b) and flowering time (FIGS. 5c,d) phenotypes of pft1 were rescued by transformation of a genomic copy of the predicted wild-type gene. Overexpression of PFT1 caused an early flowering phenotype, suggesting that PFT is limiting for flowering (FIG. 5d). Transformation of pft1 plants with PFT1 cDNA under the strong 35S promoter also produced a high proportion of co-suppressed plants, whose phenotypes were not more severe than the pft1 mutant. These data lend support to the interpretation that the pft1 allele is a strong or null allele (FIG. 5d and data not shown). In a separate experiment, plants overexpressing PFT1 were early flowering at lower temperatures indicating that PFT1 may also be involved in responses to temperature (data not shown).

To study the subcellular localization of PFT1, GFP was fused to either the N or C-terminus of PFT1 in the context of the genomic clone. These constructs encode a functional protein as they complemented the pft1 phenotype (data not shown). Both N and C terminal GFP fusions localize to the nucleus (data not shown). The GFP fusions in plants grown under R, FR and WL (white light) were also analyzed. Differences in PFT1 localization were not observed (data not shown) suggesting that phyB regulation of PFT1 activity might occur postranscriptionally or through association with other proteins.

Example 6

FT and CO mRNA Levels in WT, phyB, pft1 and pft1 phyB Mutants

To test the nature of phyB suppression by pft1, the role of pft1 in the regulation of key flowering time genes was investigated. FLOWERING LOCUS T (FT) is an integrator of several flowering time pathways, including the photoperiod pathway. FT expression has been shown to be lower in phyA and cry2 mutants in conditions where these mutants are late flowering (Yanovsky et al. Nature 419, 308-312 (2002)). The expression patterns of FT mRNA in WT, phyB, pft1 and phyBpft1 double mutants were analyzed. Expression levels in 8-day old seedlings were first tested, as previously described (Blazquez, et al. Plant Physiol 120, 1025-32 (1999)), at the first day where plants grown in LD are committed to flowering (Bradley, et al. Science 275, 80-3 (1997)). In LD-grown seedlings, FT expression was significantly higher in phyB mutants compared to. WT (FIG. 6b), suggesting that phyA and phyB have opposing roles in flowering by differentially regulating FT expression. In contrast, these differences were not found in 8 day-old seedlings grown in SD (data not shown). This could be due to the lack of commitment of SD grown seedlings at this early stage of development (note that WT plants bolt at 70 days in these conditions). Thus, FT mRNA levels in 26-day old plants grown in SD were tested. At this time point, phyB mutants are approximately two weeks from flowering, a similar difference between the commitment to flower and the actual bolting time when grown in LD (FIGS. 4b, c and data not shown). Under these conditions, a large increase in FT mRNA levels in phyB mutants compared to WT plants (FIG. 6a-b) was observed. These data thus provide a molecular mechanism for the early flowering time of phyB mutants in both LD and SD. Moreover, FT mRNA levels were low in pft1 and phyBpft1 double mutants in all the conditions tested (FIG. 6a-b), suggesting that this is the molecular mechanism for the suppression of the early flowering time phenotype of phyB mutants by pft1.

Figure 6:
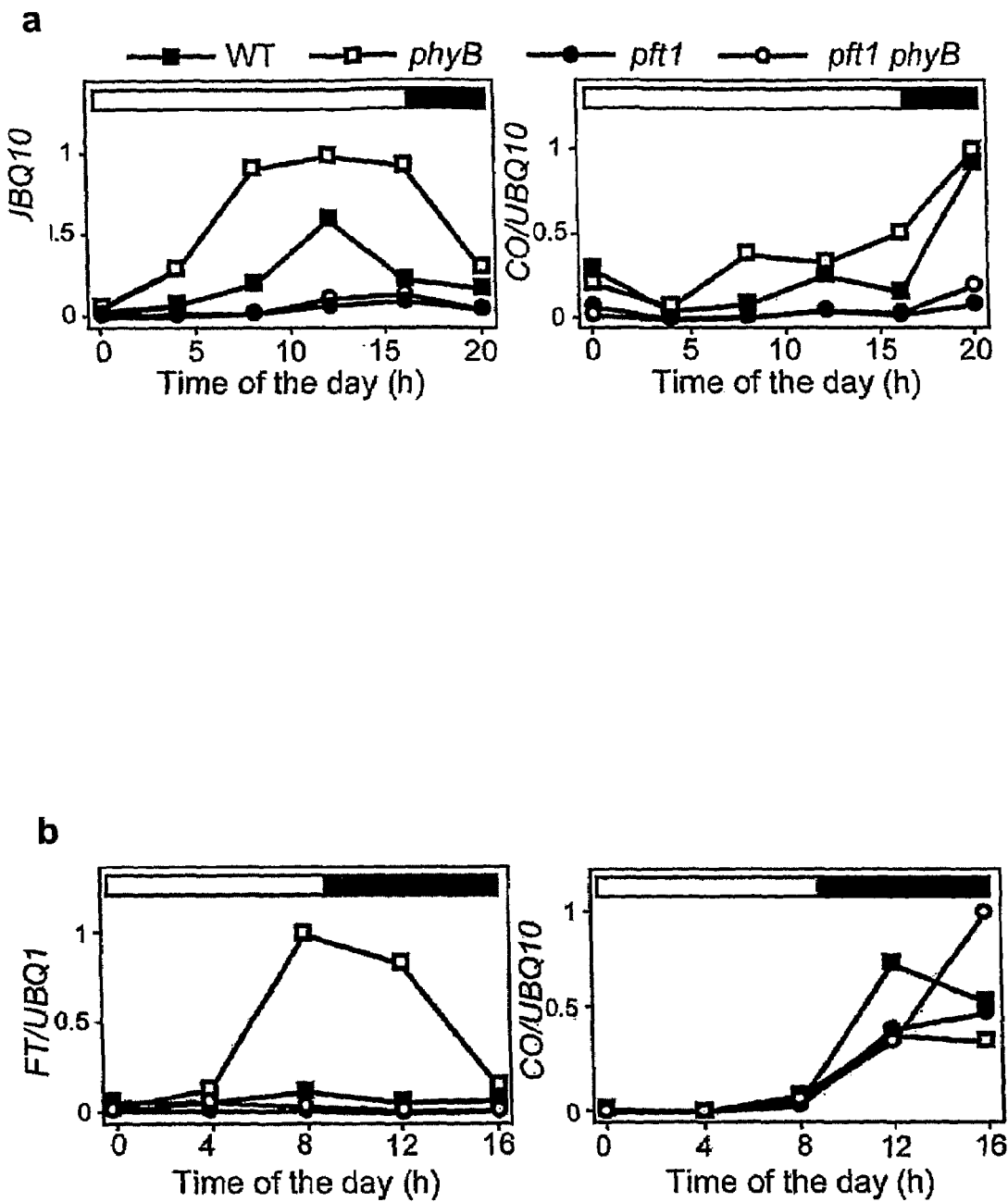
FIG. 6. FT and CO mRNA levels in WT, phyB, pft1 and pft1 phyB mutants. a, quantification of FT and CO expression in 8 day-old seedlings grown under long-day and harvested at the indicated time (0=lights on) relative to the UBQ10 control. b, quantification of FT and CO expression in 26 day-old seedlings grown under long-day and harvested at the indicated time (0=lights on) relative to the UBQ10 control. Data in a and b are representative of two independent experiments.
Figure 7:
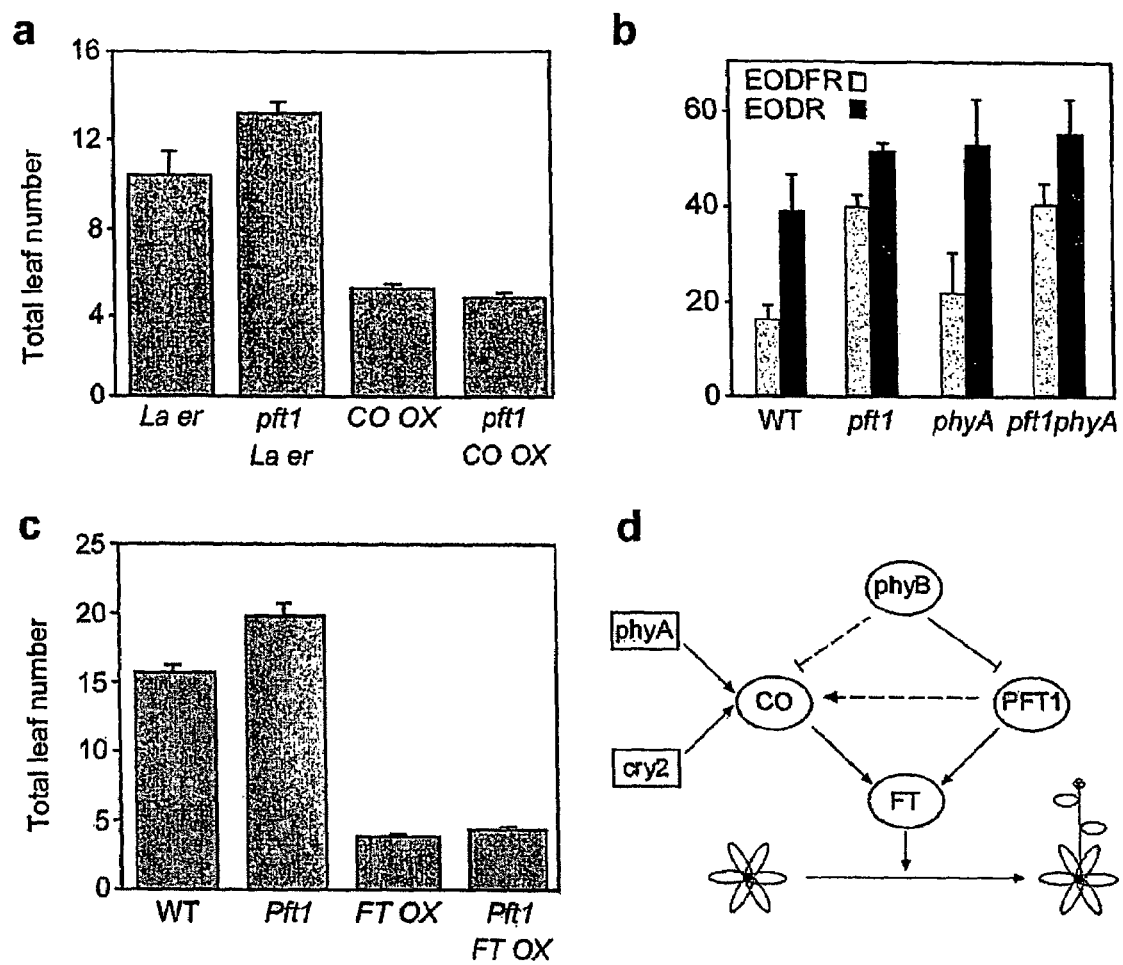
FIG. 7. FT and CO overexpression suppress the pft1 flowering time phenotype. a, flowering time of WT, pft1, FT overexpressor in WT (FT OX) and pft1 (pft1FT OX) backgrounds. b, flowering time of WT (cv Landsberg erecta), pft1, CO overexpressor in WT (CO OX) and pft1 (pft1CO OX) backgrounds. For this particular experiment the pft1 mutation was introgressed 4 times into the Landsberg erecta ecotype before crossing to CO OX lines. Data from (a) and (b) are media±SE of at least 10 plants. c, A proposed model to explain PFT1 involvement in flowering time. With the exception of the direct regulation of FT by CO (Samach, A. et al. *Science* 288, 1613-6, 2000), other arrows do not represent direct regulation or interaction. phyA and cry2 appear to mediate a direct effect of light on CO activity (Yanovsky, M. J., et al. *Nature* 419, 308-12, 2002). The role of FT in the proposed pathway is based on previous studies (Kardailsky, I., et al. *Science* 286, 1962-5, 1999; and Kobayashi, Y., et al. *Science* 286, 1960-2, 1999). The placement of PFT1 is deduced from this work.

CONSTANTS (CO) is a key component of the photoperiod pathway which integrates information from the circadian clock (Suarez-Lopez, et al. Nature 410, 1116-20 (2001)) as well as phyA and cry2 signaling (Yanovsky, et al. Nature 419, 308-12 (2002)). CO also directly activates FT expression (Samach, et al. Science 288, 1613-6 (2000)). Higher levels of CO mRNA in LD grown phyB seedlings were found compared to WT and lower levels were found in the pft1 background, thus suggesting that PFT1 could function upstream of CO in the regulation of FT (FIG. 6a). However in SD grown plants, increased levels of CO in phyB mutants were not detected, nor were the levels decreased in the pf1 background (FIG. 6c). This is consistent with a role for CO specific to LD grown plants. These data suggest that if phyB regulates flowering through PFT1 by lowering CO mRNA levels, this is not the only mechanism. A different pathway must exist, especially in SD. PFT1 could activate FT expression by regulating CO activity or simply act in a parallel pathway, independently of CO. Consistent with this latter possibility, loss of CO only partially suppresses the early flowering time of phyB mutants. Both FT and CO overexpression produce a strong early flowering phenotype that is independent of the presence of PFT1 (FIGS. 7a, b) supporting a model in which FT is activated downstream of PFT1 while CO may act downstream, but also act in a parallel pathway to PFT1 (FIG. 7c).

Figure 8:
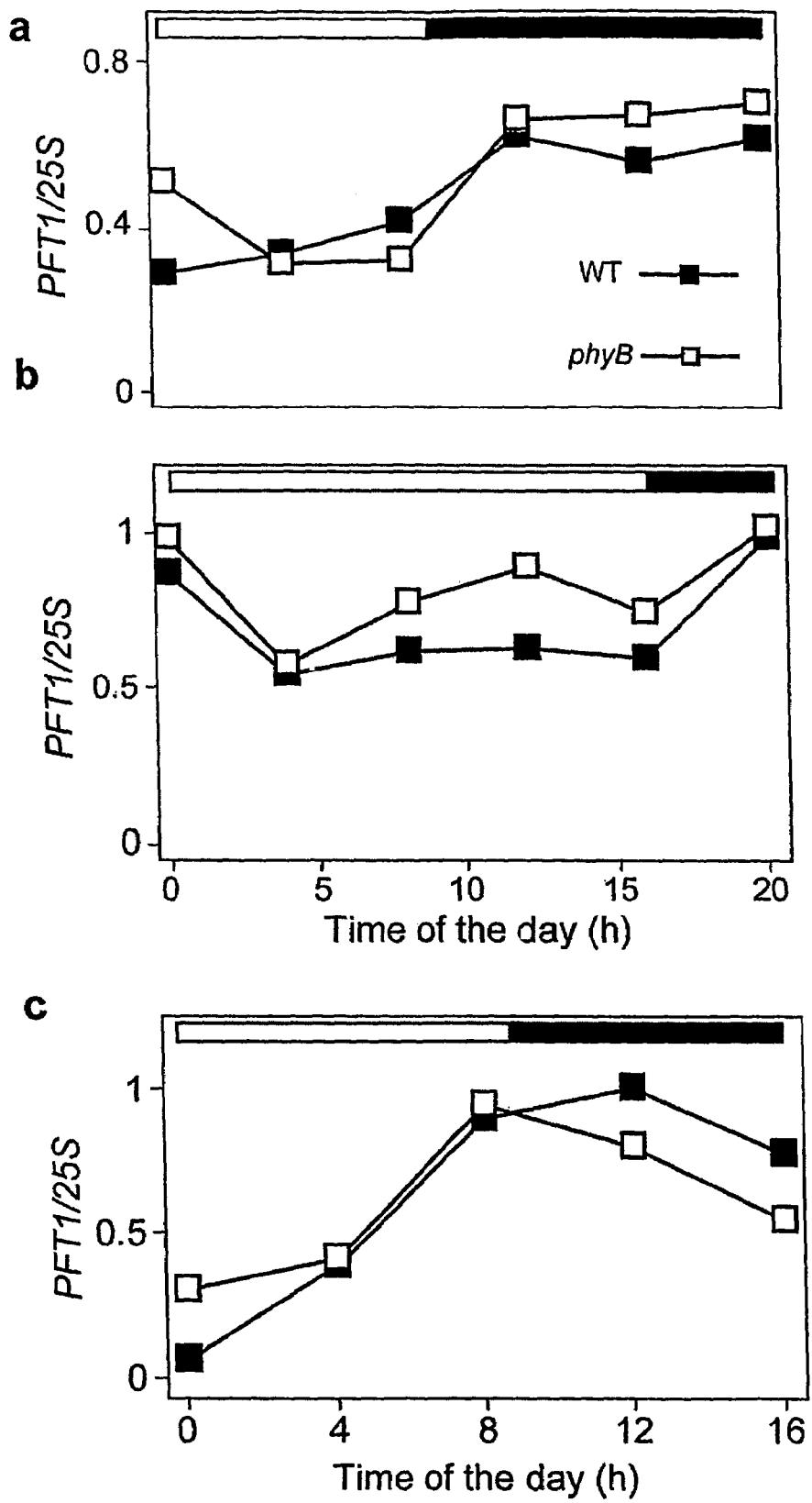
FIG. 8. PFT1 expression in WT and phyB plants. a, pft1 and 25S expression in WT and phyB plants under SD and LD conditions. Seedlings were harvested at the indicated times (0=lights on). b, quantification of data shown in (a) relative to the 25S control. c, PFT1 and 25S expression in WT and phyB plants. Seedlings were grown under (LD or SD) conditions and harvested at the times indicated (0=lights on). d, quantification of data shown in (c) relative to the 25S control.

The data presented so far suggests that PFT1 is a positive regulator of flowering whose action is inhibited by phyB. PFT1 mRNA levels are slightly elevated in phyB mutants relative to WT (FIG. 8). This increased expression cannot fully explain the effects of PFT1 on flowering time, however, as PFT1 overexpression lines did not flower as early as phyB mutants (compare FIGS. 4c and 5d). These results suggest that regulation of PFT1 activity by phyB is subject to more complex mechanisms.

The phyB mutation has a stronger inductive effect in non-inductive photoperiods (SD in long-day plants and LD in short-day plants) suggesting a role in photoperiod sensing. However, the accelerated flowering of phyB mutants could be the result of a general inhibitory effect that is independent of daylength. Consistent with these observations a "light quality" pathway has been proposed (Simpson, et al. Science 296, 285-9 (2002)) to explain the role of phyB and other stable phytochromes (phyD and phyE in *Arabidopsis* in flowering. This light quality perception pathway may be involved in the shade avoidance syndrome triggered in response to lower red/far-red ratios (Ballare, C. L. *Trends Plant Sci* 4, 201 (1999)). In contrast to co and cophyB double mutants, pft1 and pft1 phyB double mutants show a strong response to photoperiod (FIGS. 4b, c). This observation strongly suggests an important role of phyB and PFT1 in a photoperiod-independent pathway, likely, a "light quality pathway". In support of this view, FR pulses following each SD period greatly accelerated flowering in WT plants, but not in pft1 mutants (total leaf number; WT: 16±3.29; pft1: 39.9±2.9) compared to SD grown plants (FIG. 4c). A model is proposed where PFT1 acts in this "light quality pathway" downstream of phyB. The resulting signal is then integrated with the photoperiod pathway through the modulation of FT transcription, which may involve the action of CO.

Example 7

Expression of the PFT1 Genes in Tobacco

The PFT1 gene is transformed into tobacco plants. To confirm that expression of PFT1 in other plants leads to the PFT1 phenotype the PFT1 gene is transformed and expressed in tobacco using the method described by Gallois et al. (Methods Mol. Biol (1995) 49:39). The transgenic tobacco plants have phenotypes identical or similar to the phenotypes observed in *Arabidopsis*.

Example 8

Expression of PFT1 Genes in Rice

The PFT1 gene as represented by SEQ ID NO:1 or by SEQ ID NO 16 is introduced into rice embryos employing a commercially available ballistic micro-projectile device. The bombarded embryos are grown on N6 medium (see Chu et al., Scientia Sinica, 18:659-668, 1975) containing hygromycin. Regenerated hygromycin resistant plants are analyzed by PCR and Southern blot analysis for the presence of inheritable PFT1 DNA. The results indicate that the genomic DNA of the rice transformants contain inheritable copies of the transgene.

Example 9

Expression of PFT1 Genes in Tomato

The transformation of seedlings of *L. esculentum* cv. UC82 (grown from seeds obtained from Ferry Morse Seed Co., Modesto, Calif.) is done according to the protocol of Fillatti et al. [(1987) Bio/Technology 5:726-730], with modifications as described below.

Cotyledons are excised from eight-day-old tomato seedlings germinated in vitro and cut into three sections. The middle sections with dimensions 0.5 cm×0.25 cm are placed abaxile side up on one-day-preconditioned tobacco feeder plates containing KCMS incubation medium [Murashige and Skoog salt base (Gibco Laboratories, Grand Island, N.Y.) with thiamine-HCl, 1.3 mg/l; 2,4-dichlorophenoxyacetic acid, 0.2 mg/l; kinetin, 0.1 mg/l; monobasic potassium phosphate, 200 mg/l; myo-inositol, 100 mg/l; sucrose, 30 mg/l; tissue culture agar, 8 g/l, pH 5.7] and are incubated at 27° C. with 16 hours of light per day.

The tobacco feeder plates are prepared according to the method of Horsch and Jones [(1980) In Vitro 16:103-1089] with the following modifications. Cells from a six-day-old tobacco suspension culture are resuspended in fresh MM medium (Murashige and Skoog salt base with thiamine-HCl, 0.1 mg/l; pyridoxine-HCl, 0.5 mg/l; nicotinic acid, 0.5 mg/l; glycine, 2 mg/l; 6-benzylaminopurine, 0.5 mg/l; 2,4-dichlorophenoxyacetic acid, 0.5 mg/l; myo-inositol, 100 mg/l; sucrose, 30 g/l, pH 5.7) to a final density of 0.3 g fresh weight per ml. The suspension were stirred, and 1.5 ml aliquots are pipetted onto KCMS medium (25 ml) solidified with tissue culture agar (0.8% w/v) in 100 mm×20 mm plastic petri plates.

After one day of incubation of tomato cotyledon tissue on the tobacco feeder plates, the explants were floated in 20 ml of Murashige and Skoog liquid medium without hormones containing an overnight culture of *Agrobacterium tumefaciens* strain LBA4404 [Clontech, Palo Alto, Calif.; see also Ooms et al. (1982) Plasmid 7:15-19], harboring a transformation vector containing PFT1, which were inserted into *A. tumefaciens* through triparental mating.

*A. tumefaciens* strain 13A4404 is maintained at a density of $5 \times 10^8$ cells/ml. The tissue and *Agrobacterium* are incubated at room temperature for 30 min, after which time the explants are blotted on sterile Whatman paper No. 1 and transferred to tobacco feeder plates. The cultures are incubated at 27° C. with 16 hr of light per day. After two days of incubation, the treated cotyledon segments are transferred to regeneration 2Z medium (Murashige and Skoog salt base with thiamine-HCl, 1.0 mg/l; pyridoxine-HCl, 0.5 mg/l; nicotinic acid, 0.5 mg/l; glycine, 2 mg/l; zeatin, 2 mg/l; sucrose, 30 g/l; myo-inositol, 100 mg/l; tissue culture agar, 8 g/l, pH 5.7) with 500 µg/ml cefotaxime and 100 µg/ml kanamycin).

The cultures are being incubated at 27° C. with 16 hours of light per day under 4,000 lux of light intensity. When kanamycin-resistant shoots reach a height of one inch, they will be rooted on rooting medium, which is identical to regeneration 2Z medium except that it lacks hormones and contains 250 µg/ml cefotaxime and 50 µg/ml kanamycin. The transgenic shoots will then be grown into fruit-bearing transgenic tomato plants.

---

What is claimed is:

1. A method of modulating flowering time in a plant comprising
altering the level of PHYTOCHROME AND FLOWERING TIME 1 (PFT1) protein in a plant, wherein the amino acid sequence of said PFT1 protein is set forth in SEQ ID NO: 3.

2. The method of claim 1, wherein said PFT1 protein is encoded by the nucleotide sequence set forth in SEQ ID NO. 2.

3. The method of claim 1, wherein the level of PFT1 protein is altered by transforming a plant with an expression vector comprising a gene encoding the PFT1 protein.

4. The method of claim 3, wherein the gene encoding the PFT1 protein has a nucleotide sequence that encodes the amino acid sequence set forth in SEQ ID NO. 3.

5. The method of claim 3, wherein the gene encoding the PFT1 protein has the nucleotide sequence set forth in SEQ ID NO. 2.

6. A method of modulating flowering time in a plant, comprising:
   transforming a plant cell with an expression vector comprising a gene that encodes a PFT1 protein,
   wherein the amino acid sequence of said PFT1 protein is set forth in SEQ ID NO: 3; and
   growing said plant cell into a plant under conditions that allow the expression of the PFT1 protein thereby modulating flowering time.

7. The method of claim 6, wherein the PFT1 protein is overexpressed in said plant.

8. The method of claim 6, wherein the PFT1 protein is encoded by a gene comprising the nucleotide sequence shown in SEQ ID NO: 2.

9. The method of claim 6, wherein the expression vector comprises a promoter selected from the group consisting of a constitutive promoter and an inducible promoter.

10. The method of claim 6, wherein the plant is selected from the group consisting of: wheat, barley, rye, oat, flax, millet, corn, tomato, rice and tobacco plants.

11. The method of claim 6, wherein flowering time is decreased.

12. A transgenic plant having modulated flowering time as compared to a wild-type plant,
   wherein the transgenic plant comprises a recombinant expression vector that expresses a nucleic acid encoding a PFT1 gene,
   wherein said PFT1 gene has a nucleotide sequence that encodes the amino acid sequence set forth in SEQ ID NO: 3.

13. The transgenic plant of claim 12, wherein the PFT1 gene is overexpressed.

14. A recombinant nucleic acid comprising SEQ ID NO:2.

15. A recombinant nucleic acid comprising a nucleotide sequence encoding SEQ ID NO:3.

16. A transgenic plant comprising a recombinant expression vector that expresses the recombinant nucleic acid sequence of claim 14 or 15.

17. The transgenic plant of claim 16, wherein the recombinant nucleic acid sequence is overexpressed.

18. The transgenic plant of claim 16, wherein the recombinant nucleic acid sequence is operably linked to a promoter.

19. The transgenic plant of claim 18, wherein the promoter is selected from the group consisting of a constitutive promoter and an inducible promoter.

20. The transgenic plant of claim 16, wherein the plant is selected from the group consisting of: wheat, barley, rye, oat, flax, millet, corn, tomato, rice and tobacco plants.

21. A seed comprising a recombinant expression vector that expresses the recombinant nucleic acid of claim 14 or 15.

22. A plant tissue derived from the transgenic plant of claim 16, wherein the plant tissue comprises a recombinant expression vector that expresses a recombinant nucleic acid comprising a nucleotide sequence encoding SEQ ID NO: 3.

23. The plant tissue of claim 22, wherein said tissue is a flower.

24. The method of claim 12, wherein the nucleotide sequence is set forth in SEQ ID NO.2.

25. A plant tissue derived from the transgenic plant of claim 16, wherein the plant tissue comprises a recombinant expression vector that expresses a recombinant nucleic acid comprising SEQ ID NO: 2.

* * * * *

SEQUENCE LISTING

```
<160> NUMBER OF SEQ ID NOS: 17

<210> SEQ ID NO 1
<211> LENGTH: 8040
<212> TYPE: DNA
<213> ORGANISM: Arabidopsis thaliana

<400> SEQUENCE: 1
agtggttgag aatctgcagc cttaggtttc tccttttgaa acggttgaaa cgcaccagcg      60
ctgcgtttga cttcaattac catcggtttc ttattattag gttgtggatc tggtgattgg     120
ttccacaatt gaacagatct aagccaatcc gatttcttct tatcaccatc gttattttca     180
ttggtcatca tctcagtttt ctcagcttct tcatctttat cggtttcatc agatgaagca     240
```

```
gaactccact tgattggcat aaactcttca aacacggcac cgccgcattc actagttgtc    300
cgctcagaac attctgactg gccgccaaca tgttctgaag attccgataa ctccttccga    360
catgactcga tagctacaag aatgatatgt aaacaattaa gaaactggaa gcgatcgtga    420
aaacgaagaa tatatatatc aaaagaggat gtgtaataac attaccttgg gttacaagtt    480
ctaaacataa agggagctca cgttgaaaga cttgaatctt tttttgttct tcttctagag    540
cttctacata ttcgtgacat ctcttcattt tctgggtgta atccatgtca ccgctcttga    600
acatcatcat tatgaacaga tcttagactc gttttgcta tgagttacag ttacgaaaac    660
ataaatcttg agagagacag agaagagttt tggatctaaa atgagagaga aaggataaaa    720 cttgacgtt tttaagttgg aagttttaaa gggcagagaa agaggattgg tgtctaatcg    780
aggtcgggcc gtcgcgtacc taaaaccgaa tcttcttgat gtttagattt attcggattt    840
tacttgggaa agggtagaat ggtaaatata ggaataggct gaggtttgtt tgatacaggg    900
agaatattcg gggatatgtg gattccttcc tttccatatt ctatcgagct ggcgatgatg    960
tcagcattct catgacgttg acgttgagat aagaacgacg agtcatttta gtcattacta   1020
actctttctt ttttcttcgg ttattctcta cctattttag aaatatacac atgaattttt   1080
ttgtaataac aaacgagtga agaagaatat ccatagagat tggaatcaag atatgtaacc   1140
agaaaatttt aaacattcat taaatttaca gtttagaata tattatatgg tatcatatca   1200
taaattacat ttttatcaga aaagaaaaag ataagaagt ttttggcaaa agtggaggaa    1260
tattcctcga gagtagggga gaaactaagc tggaaaaaaa catattaaat tggaaaaaat   1320
tgggaaggag agaatctttg gaagagtgac attcacacat atccagatcc cccgtttcc    1380 tcatgaattg ttaaattttg gcccttcacg ctatcgaaga gccacctgcc ccatatcaca   1440
ccaacctact cgcctctttt cacgcgcttc attgtgtgtt gttgtgttgt gatatattca   1500
agcaattctc gtgaatacct gacgattcta aattggttgg cgacaaaaac acacacaaaa   1560
aaacacacac tataaaacgg aattaagtgt ctaattttga gtatgtattc ttgagaaaat   1620
ttctctaaat agtttggaga ttgaggtttt tgtactgtct gctacggtta ccaaactgta   1680
gaaactattg tgtatcaata attaaatttg gattttaag acaattgta aaagcttata     1740 actaggtgat ggattgagtt gtggtaaagt caaattgttc gagaggtcgt aaacagtgag   1800
aagcaattta aggaagatga taattattca tttgtgatgg tttctttgag ttatggtctt   1860
atggataatg tccatggatg tgaagaccac caacattgta ttagataaaa aaaaactacc   1920
acgtgaaaag tagttgattt tgggttctca tgacttctca caaactcacg tttccatagc   1980
attgcatggc aatttacaat gtgttgcccc tcccttagta ctaccaatac taccatatga   2040
acaacgatcg ggatcagcaa aatctatagc tttgtagccg tcttctatga ctcatctctt   2100
ccacaaaaag tcattgacat caactagtct aagatgactg acatacgaaa ttggatccta   2160
ttttccacta ggccactctg aaaagaaaaa aacacagata aaaaggccat gcggcccatg   2220
tccaactttt ggaccaatct taaatggcct tcacaatggt tatcatggcc tttatttgat   2280
tcaagtctgg actaactaca actatgtata caaaatgttt atccacatag cccaaaataa   2340
gatatcaaat tggttacttt catttttttt tacgtgatcg accttaagct tgttgttagt   2400
tttggcgttc gatgaaccac ctccaaacca attatattct tcacaagatt ctctgcattt   2460
atcccacaga tggtaaacaa tctaatcaaa ttaaattcac ttcttcacca aaaaaaataa   2520
aattaaattc attgcccaat ttacacaaat aaaaagatag taacgaccaa gtcctttgta   2580
tatcccattt tctattcgga gcatccaaac caaattttgt caatctaatt tatcttctcc   2640
```

```
tctcccggag aagaaggaaa cttacaattt acaaagaacg agcttcaata aaaatttcca    2700
aagaaattac cgtcggcgaa tcgttaggct cgagaagaat caccaaattc caaggggaga    2760
gagactgaat tttcttttga ttcacgtaac aacaacgctc agagactatg tcgtcggagg    2820
tgaaacagct gatcgtcgtt gctgaaggca ccgccgcttt gggtccttat tggcaaacca    2880
tcgtctccga ctatctcgag aaaatcatca ggttttctct tttatgaacc ttgtatctct    2940
tttaatcctc gttatttgat tttcattcgg agttaggggta tagctgatac cgttcgaatc    3000
aggctttaat ttcaattggt tagatcaaac ctttgtttat cctctgattc cacaatgttt    3060
tgttgttcgt tgttagtact gtgtttatgt atttgattgt tctgtgtttc atattgagca    3120
atcactttac gttaccttat ggttcctaca ttcttttttt gtgttaggac attgttttcg    3180
atacaacgca ttcataaagc aatgaatttg tagtttctca cttcgatcac gtaaaattga    3240
tattaatatg tgattacaga gaatttagta tataattgcc tgtatagttt gtaactaatc    3300
acattgttgg ctattcttaa tatccactca acatagtatt gtatttcaaa gtagcgtttt    3360
tgtatgttaa aatttcaatt acataatctg tctatgcatt cttttgcattt gtccaggtct    3420 ttctgtggca gtgagttaaa tggagaggta ctatatctga cttatcctcg ttttttaagtt    3480 tactcaagtt ttcattcttg agcaaacagt taatcaatgt ttttgaccaa actcatatac    3540
attcgttatc tgtcaaatca ttgcgacaca aaaataaca gagcaaattg gtagtttgat    3600
gtgtctgatc gagtctttat atattcacta aacttgcaga ggaaccctgt ttctactgtt    3660
gagctatcac tggtgatctt caattctcat ggttcatatt gtggtacgtg ttgtgcttca    3720
tcttgtgata tccaaataca aatattattt gggtgctttc tcatggccct ggttacatta    3780
gcttttgttt tagtaatgtt gttcttatct ttcattcttc ttagcttgct tggtacaacg    3840
gagtggctgg acaagggatg ttgatatttt cttgcattgg ctttcttcca tacaatttgg    3900
tggtggtggt ttcaatgagg ttgccacagc tgaagggctt gccgaagcat tgatggtggg    3960
aaacttgatc tcttttcatc tgtgacacaa ctataagaca tatgtttggg ccactttctt    4020
tcaagctact tttgactaat ttactttctc aataaaatta acttttttct ttccatggct    4080 tcatttatg tggtggtgct tctgtcagcg atttctcga tccttaaacc tcacaatttt    4140
ctctgacttc atgacacaga tgttttctcc tccttcaggc caagctcaac caagtaacga    4200
tctgaaaaga cactgtatcc taatcacagc cagcaatcct cacatattgc caacacctgt    4260
atatcgtcca cgattgcaaa atgtggaacg gaatgagaat ggtgatgcgc aagctgagag    4320
tcgattatca gatgctgaga cagtggcttc atattttgct aaggtacttt ttttaactga    4380
ttcccccagg tattacaact agctataatt actccttta atgggaaatt actaacctgc    4440
catattggtg tgcagtgttc tgtttctttg tctgttgtat gtccaaagca gcttccaaca    4500
attagagcac tatacaatgc ggtgagactg cgtgtctatt tgctattcac tagatgtaca    4560
tctatcaaaa gtctttcttt tgtcagacag ctctttcaaa ggctgtcttt attctcaatg    4620
ctataaactg gtgtaatctt tgttttatac tgttttaaat gcagggaaag cccaatcaac    4680
aaagtgcgga cttgtcaatt gacacggcta agaacacatt ctatcttgtc ctgatctcgg    4740
agaattttgt ggaggcatgt gctgccttaa gtcattctgc tacaaatttg ccacagactc    4800
agagccctgt gaaagtggac agggccactg ttgctccatc tattccagtc actgggcaac    4860
ctccagctcc tgtgtcatca ggttcttcta ctgacaacat ccatttttct tagtccaact    4920
atcttgattt tccttttgtgc ttcttttggat tctatcctgc ttctctatat gaagatctct    4980
ttttgtatga ttttcagcca atggacctat tcagaatcgg caaccagttt ctgttggacc    5040
```

```
agttccaact gctactgtga agttgtaag tctatttgat cttttagtc agttggagga    5100
gtcagctcta tctattggca accgactctt gtatgttta taagaattat ttactagata   5160
ttagccgaaa atgaattgta aatttattct ctggtgcttg ataagacatt acaaattttt   5220
atgtgttaat caactagatt taatgttaag ttcatatgaa tatcccattt gtgaaataat   5280
attgtatact caatcagctt attagatagc atatcttcac attagtagaa gcctgttaat   5340
cagatttttg gaatgaaatt gcaggagcct agcaccgtaa cttctatggc accagttcct   5400
agttttcccc atatcccggc tgtagctcgg cctgctacac aagcaattcc ttcgattcaa   5460
acatcttcag catcaccagt ttctcaggat atggtcagca acgccgagaa tgcaccagat   5520
attaagcctg tggtggtcag tggaatgacg ccaccattgc gtactggtcc tcctggtgga   5580
gccaatgtaa atctgcttaa taatctttct caagtccgac aagtcatgag ctctgcagct   5640
ctggcaggtg cagcctcatc ggttgggcaa agtgcggttg caatgcatat gtcaaatatg   5700
atatcaacag gaatggctac atctttgcct ccttcacaaa ctgtgttttc aactggacag   5760
cagggaatta cttcaatggc tggttcgggt gcactaatgg gatctgcaca acgggacaa    5820
agcccgggtc ctaataatgc ctttagtcct caaacaacgt caaatgtcgc ttcaaacctt   5880
ggtgtttcac aaccaatgca agggatgaac caaggaagtc attctggagc aatgatgcaa   5940
ggtggaattt ccatgaacca aaacatgatg agtggtcttg gtcaaggaaa tgtctcctct   6000
ggaacaggtg gaatgatgcc tactccagga gttggccaac aagcgcaatc aggaatacaa   6060
caacttggtg gcagtaacag ctcagctcct aatatgcagc tatcacagcc atcatcgggg   6120
gctatgcaga cttcacaatc caaatatgtg aaagtctggg aggtaatgtc agtttatctt   6180
gtctaaaata acggtgatct tgtgctaact tttacttaca ttttcaaatt catgcaggga   6240
aatttatctg ggcaaaggca agggcagcct gttcttatca ccagacttga ggtgtgttta   6300
ggggcactta ctatgcactt ttctttcccc tttttctgaat ttactgggat cacatgctta   6360
agcacatctt cctctgtaga actttgttga attgttccaa gtagatatta actaacgtct   6420
ttgtttatat ttgacagggt taccgaagtg cttctgcctc tgattcgtaa gtttataact   6480
aattgaaata tgaaaactgc ttccttacta aaccttgtca ggagagcagt cgactcctta   6540
agaaatgatt gtagctgcta aactaatttt tgctttctct ttttgtgcat ctccccaggt   6600
tggcagcaaa ctggccacca actatgcaga ttgttcgtct catatcccag gaccatatga   6660
ataacaagta atatcttcgt gctatatcct tccttattcc aaatggctca tgggtggatg   6720
ttgatttcat gccactaaat atttcacctg actttgcatc aggcaatatg ttggcaaagc   6780
tgacttcctt gtgtttcggg ccatgagtca acatgggttc ttaggacaac ttcaggataa   6840
aaagcttgtg agtattgttg ataatttatg ccacttgtct cctttttcctt attgtttcac   6900
tacaaattta ataacaaaat gatgaatggt gtttactggt ttattagata ttaggatgaa   6960
ttagatgtta agaatgaaaa tctttgaaaa aatatatgta cttacatctg taaacatgtt   7020
ctcggtgaat ctatcaatct cttgctatgt tcaccataca cttaacgatg cctacgcttg   7080
tatgtagcct tgttttgatt agcctaatcg tgtgccatac tattgtcatt ttcacgctta   7140
gcttttgtgg agttgtatat gataactttg tcatcctccg tattgcagtg tgcagtcatc   7200
cagttgccat cacagacgct tcttctctct gtctctgaca aggcttgccg cttgattgga   7260
atgcttttcc caggggtaag gaagtactaa gtttaaggtg tctatatatg ttttgcttca   7320
cattagtgac tcttgagggt tgttttgttt actcctagga tatggttgtg tttaaaccac   7380
aaattccaaa tcagcaacag cagcagcaac aacaactcca ccagcaacaa caacaacaac   7440
```

-continued

| | |
|---|---|
| agcagatcca gcagcagcag caacaacaac aacacctcca acagcaacag atgccacaac | 7500 |
| tccagcaaca acaacaacaa caccagcagc aacagcaaca gcagcatcaa ttgtcacagc | 7560 |
| tccaacatca tcagcagcaa caacaacaac agcagcaaca acagcagcag catcaattga | 7620 |
| cacagcttca acaccatcat cagcagcagc agcaggcgtc gccgctgaat cagatgcagc | 7680 |
| agcagacttc gccgctcaat cagatgcagc aacagacttc gcctctgaat cagatgcagc | 7740 |
| agcaacagca gcctcaacag atggtaatgg gtggtcaagc ttttgcacaa gcccctggaa | 7800 |
| gatcacaaca aggtggtggt ggagggcagc ctaacatgcc tggagctggc ttcatgggat | 7860 |
| aaataaaaat atcagcttca gtgctaatta attagattta tcataactta acattctttc | 7920 |
| tttcttcttt ggtcaactcg atcgtcgcca tggttttaga ctctgtttag ttgtcctttc | 7980 |
| tgttcttttg agcctgaaaa tggcatgtcc tattctgtat gggtctgacc atttagctac | 8040 |

<210> SEQ ID NO 2
<211> LENGTH: 2689
<212> TYPE: DNA
<213> ORGANISM: Arabidopsis thaliana

<400> SEQUENCE: 2

| | |
|---|---|
| atgtcgtcgg aggtgaaaca gctgatcgtc gttgctgaag caccgccgc tttgggtcct | 60 |
| tattggcaaa ccatcgtctc cgactatctc gagaaaatca tcaggtcttt ctgtggcagt | 120 |
| gagttaaatg gagagaggaa ccctgtttct actgttgagc tatcactggt gatcttcaat | 180 |
| tctcatggtt catattgtgc ttgcttggta caacggagtg gctggacaag ggatgttgat | 240 |
| attttcttgc attggctttc ttccatacaa tttggtggtg gtggtttcaa tgaggttgcc | 300 |
| acagctgaag ggcttgccga agcattgatg atgttttctc ctccttcagg ccaagctcaa | 360 |
| ccaagtaacg atctgaaaag acactgtatc ctaatcacag ccagcaatcc tcacatattg | 420 |
| ccaacacctg tatatcgtcc acgattgcaa aatgtggaac ggaatgagaa tggtgatgcg | 480 |
| caagctgaga gtcgattatc agatgctgag acagtggctt catattttgc taagtgttct | 540 |
| gtttctttgt ctgttgtatg tccaaagcag cttccaacaa ttagagcact atacaatgcg | 600 |
| ggaaagccca atcaacaaag tgcggacttg tcaattgaca cggctaagaa cacattctat | 660 |
| cttgtcctga tctcggagaa ttttgtggag gcatgtgctg ccttaagtca ttctgctaca | 720 |
| aatttgccac agactcagag ccctgtgaaa gtggacaggg ccactgttgc tccatctatt | 780 |
| ccagtcactg gcaacctcc agctcctgtg tcatcagcca atggacctat tcagaatcgg | 840 |
| caaccagttt ctgttggacc agttccaact gctactgtga agttgagcc tagcaccgta | 900 |
| acttctatgg caccagttcc tagttttccc catatcccgg ctgtagctcg gcctgctaca | 960 |
| caagcaattc cttcgattca acatcttca gcatcaccag tttctcagga tatggtcagc | 1020 |
| aacgccgaga tgcaccaga tattaagcct gtggtggtca gtggaatgac gccaccattg | 1080 |
| cgtactggtc ctcctggtgg agccaatgta atctgcttca taatctttc tcaagtccga | 1140 |
| caagtcatga gctctgcagc tctggcaggt gcagcctcat cggttgggca agtgcggtt | 1200 |
| gcaatgcata tgtcaaatat gatatcaaca ggaatggcta catctttgcc tccttcacaa | 1260 |
| actgtgtttt caactggaca gcagggaatt acttcaatgg ctggttcggg tgcactaatg | 1320 |
| ggatctgcac aaacgggaca aagcccgggt cctaataatg cctttagtcc tcaaacaacg | 1380 |
| tcaaatgtcg cttcaaacct tggtgtttca caaccaatgc aagggatgaa ccaaggaagt | 1440 |
| cattctggag caatgatgca aggtggaatt tccatgaacc aaaacatgat gagtggtctt | 1500 |
| ggtcaaggaa atgtctcctc tggaacaggt ggaatgatgc ctactccagg agttggccaa | 1560 |

-continued

```
caagcgcaat caggaataca acaacttggt ggcagtaaca gctcagctcc taatatgcag    1620
ctatcacagc catcatcggg ggctatgcag acttcacaat ccaaatatgt gaaagtctgg    1680
gagggaaatt tatctgggca aaggcaaggg cagcctgttc ttatcaccag acttgagggt    1740
taccgaagtg cttctgcctc tgattcgttg gcagcaaact ggccaccaac tatgcagatt    1800
gttcgtctca tcccagga ccatatgaat aacaagcaat atgttggcaa agctgacttc    1860
cttgtgtttc gggccatgag tcaacatggg ttcttaggac aacttcagga taaaaagctt    1920
tgtgcagtca tccagttgcc atcacagacg cttcttctct ctgtctctga caaggcttgc    1980
cgcttgattg gaatgctttt cccaggggat atggttgtgt ttaaaccaca aattccaaat    2040
cagcaacagc agcagcaaca acaactccac cagcaacaac aacaacaaca gcagatccag    2100
cagcagcagc aacaacaaca acacctccaa cagcaacaga tgccacaact ccagcaacaa    2160
caacaacaac accagcagca acagcaacag cagcatcaat tgtcacagct ccaacatcat    2220
cagcagcaac aacaacaaca gcagcaacaa cagcagcagc atcaattgac acagcttcaa    2280
caccatcatc agcagcagca gcaggcgtcg ccgctgaatc agatgcagca gcagacttcg    2340
ccgctcaatc agatgcagca acagacttcg cctctgaatc agatgcagca gcaacagcag    2400
cctcaacaga tggtaatggg tggtcaagct tttgcacaag cccctggaag atcacaacaa    2460
ggtggtggtg gagggcagcc taacatgcct ggagctggct tcatgggata aataaaaata    2520
tcagcttcag tgctaattaa ttagatttat cataacttaa cattctttct ttcttctttg    2580
gtcaactcga tcgtcgccat ggttttagac tctgtttagt tgtcctttct gttcttttga    2640
gcctgaaaat ggcatgtcct attctgtatg ggtctgacca tttagctac              2689
```

<210> SEQ ID NO 3
<211> LENGTH: 836
<212> TYPE: PRT
<213> ORGANISM: Arabidopsis thaliana

<400> SEQUENCE: 3

```
Met Ser Ser Glu Val Lys Gln Leu Ile Val Val Ala Glu Gly Thr Ala
  1               5                  10                  15

Ala Leu Gly Pro Tyr Trp Gln Thr Ile Val Ser Asp Tyr Leu Glu Lys
             20                  25                  30

Ile Ile Arg Ser Phe Cys Gly Ser Glu Leu Asn Gly Glu Arg Asn Pro
         35                  40                  45

Val Ser Thr Val Glu Leu Ser Leu Val Ile Phe Asn Ser His Gly Ser
     50                  55                  60

Tyr Cys Ala Cys Leu Val Gln Arg Ser Gly Trp Thr Arg Asp Val Asp
 65                  70                  75                  80

Ile Phe Leu His Trp Leu Ser Ser Ile Gln Phe Gly Gly Gly Gly Phe
                 85                  90                  95

Asn Glu Val Ala Thr Ala Glu Gly Leu Ala Glu Ala Leu Met Met Phe
            100                 105                 110

Ser Pro Pro Ser Gly Gln Ala Gln Pro Ser Asn Asp Leu Lys Arg His
        115                 120                 125

Cys Ile Leu Ile Thr Ala Ser Asn Pro His Ile Leu Pro Thr Pro Val
    130                 135                 140

Tyr Arg Pro Arg Leu Gln Asn Val Glu Arg Asn Glu Asn Gly Asp Ala
145                 150                 155                 160

Gln Ala Glu Ser Arg Leu Ser Asp Ala Glu Thr Val Ala Ser Tyr Phe
                165                 170                 175
```

```
Ala Lys Cys Ser Val Ser Leu Ser Val Val Cys Pro Lys Gln Leu Pro
            180                 185                 190

Thr Ile Arg Ala Leu Tyr Asn Ala Gly Lys Pro Asn Gln Gln Ser Ala
            195                 200                 205

Asp Leu Ser Ile Asp Thr Ala Lys Asn Thr Phe Tyr Leu Val Leu Ile
            210                 215                 220

Ser Glu Asn Phe Val Glu Ala Cys Ala Ala Leu Ser His Ser Ala Thr
225                 230                 235                 240

Asn Leu Pro Gln Thr Gln Ser Pro Val Lys Val Asp Arg Ala Thr Val
            245                 250                 255

Ala Pro Ser Ile Pro Val Thr Gly Gln Pro Pro Ala Pro Val Ser Ser
            260                 265                 270

Ala Asn Gly Pro Ile Gln Asn Arg Gln Pro Val Ser Val Gly Pro Val
            275                 280                 285

Pro Thr Ala Thr Val Lys Val Glu Pro Ser Thr Val Thr Ser Met Ala
            290                 295                 300

Pro Val Pro Ser Phe Pro His Ile Pro Ala Val Ala Arg Pro Ala Thr
305                 310                 315                 320

Gln Ala Ile Pro Ser Ile Gln Thr Ser Ser Ala Ser Pro Val Ser Gln
            325                 330                 335

Asp Met Val Ser Asn Ala Glu Asn Ala Pro Asp Ile Lys Pro Val Val
            340                 345                 350

Val Ser Gly Met Thr Pro Pro Leu Arg Thr Gly Pro Pro Gly Gly Ala
            355                 360                 365

Asn Val Asn Leu Leu Asn Asn Leu Ser Gln Val Arg Gln Val Met Ser
            370                 375                 380

Ser Ala Leu Ala Gly Ala Ser Ser Val Gly Gln Ser Ala Val
385                 390                 395                 400

Ala Met His Met Ser Asn Met Ile Ser Thr Gly Met Ala Thr Ser Leu
            405                 410                 415

Pro Pro Ser Gln Thr Val Phe Ser Thr Gly Gln Gln Gly Ile Thr Ser
            420                 425                 430

Met Ala Gly Ser Gly Ala Leu Met Gly Ser Ala Gln Thr Gly Gln Ser
            435                 440                 445

Pro Gly Pro Asn Asn Ala Phe Ser Pro Gln Thr Thr Ser Asn Val Ala
            450                 455                 460

Ser Asn Leu Gly Val Ser Gln Pro Met Gln Gly Met Asn Gln Gly Ser
465                 470                 475                 480

His Ser Gly Ala Met Met Gln Gly Gly Ile Ser Met Asn Gln Asn Met
            485                 490                 495

Met Ser Gly Leu Gly Gln Gly Asn Val Ser Ser Gly Thr Gly Gly Met
            500                 505                 510

Met Pro Thr Pro Gly Val Gly Gln Gln Ala Gln Ser Gly Ile Gln Gln
            515                 520                 525

Leu Gly Gly Ser Asn Ser Ser Ala Pro Asn Met Gln Leu Ser Gln Pro
            530                 535                 540

Ser Ser Gly Ala Met Gln Thr Ser Gln Ser Lys Tyr Val Lys Val Trp
545                 550                 555                 560

Glu Gly Asn Leu Ser Gly Gln Arg Gln Gly Gln Pro Val Leu Ile Thr
            565                 570                 575

Arg Leu Glu Gly Tyr Arg Ser Ala Ser Ala Ser Asp Ser Leu Ala Ala
            580                 585                 590
```

```
Asn Trp Pro Pro Thr Met Gln Ile Val Arg Leu Ile Ser Gln Asp His
            595                 600                 605

Met Asn Asn Lys Gln Tyr Val Gly Lys Ala Asp Phe Leu Val Phe Arg
    610                 615                 620

Ala Met Ser Gln His Gly Phe Leu Gly Gln Leu Gln Asp Lys Lys Leu
625                 630                 635                 640

Cys Ala Val Ile Gln Leu Pro Ser Gln Thr Leu Leu Leu Ser Val Ser
                645                 650                 655

Asp Lys Ala Cys Arg Leu Ile Gly Met Leu Phe Pro Gly Asp Met Val
                660                 665                 670

Val Phe Lys Pro Gln Ile Pro Asn Gln Gln Gln Gln Gln Gln Gln Gln
            675                 680                 685

Leu His Gln Gln Gln Gln Gln Gln Gln Ile Gln Gln Gln Gln Gln Gln
    690                 695                 700

Gln Gln Gln His Leu Gln Gln Gln Met Pro Gln Leu Gln Gln Gln Gln
705                 710                 715                 720

Gln Gln Gln His Gln Gln Gln Gln Gln Gln His Gln Leu Ser Gln
                725                 730                 735

Leu Gln His His Gln Gln Gln Gln Gln Gln Gln Gln Gln Gln Gln Gln
                740                 745                 750

Gln His Gln Leu Thr Gln Leu Gln His His Gln Gln Gln Gln Gln
    755                 760                 765

Ala Ser Pro Leu Asn Gln Met Gln Gln Thr Ser Pro Leu Asn Gln
    770                 775                 780

Met Gln Gln Gln Thr Ser Pro Leu Asn Gln Met Gln Gln Gln Gln Gln
785                 790                 795                 800

Pro Gln Gln Met Val Met Gly Gln Ala Phe Ala Gln Ala Pro Gly
                805                 810                 815

Arg Ser Gln Gln Gly Gly Gly Gly Gln Pro Asn Met Pro Gly Ala
            820                 825                 830

Gly Phe Met Gly
        835

<210> SEQ ID NO 4
<211> LENGTH: 29
<212> TYPE: DNA
<213> ORGANISM: Artificial Sequence
<220> FEATURE:
<223> OTHER INFORMATION: PCR Primer

<400> SEQUENCE: 4
cagaggaacc ctgtttctac tgttgagct                                      29

<210> SEQ ID NO 5
<211> LENGTH: 29
<212> TYPE: DNA
<213> ORGANISM: Artificial Sequence
<220> FEATURE:
<223> OTHER INFORMATION: PCR Primer

<400> SEQUENCE: 5
cgttacttgg ttgagcttgg cctgaagga                                      29

<210> SEQ ID NO 6
<211> LENGTH: 27
<212> TYPE: DNA
<213> ORGANISM: Artificial Sequence
<220> FEATURE:
<223> OTHER INFORMATION: PCR Primer
```

```
<400> SEQUENCE: 6
tcccggacat gaagccattt atatgta                                              27

<210> SEQ ID NO 7
<211> LENGTH: 27
<212> TYPE: DNA
<213> ORGANISM: Artificial Sequence
<220> FEATURE:
<223> OTHER INFORMATION: FT PCR Primer

<400> SEQUENCE: 7
gctacaactg gaacaacctt tggcaat                                              27

<210> SEQ ID NO 8
<211> LENGTH: 27
<212> TYPE: DNA
<213> ORGANISM: Artificial Sequence
<220> FEATURE:
<223> OTHER INFORMATION: CO PCR Primer

<400> SEQUENCE: 8
tataggcatc atcaccgttc gttactc                                              27

<210> SEQ ID NO 9
<211> LENGTH: 28
<212> TYPE: DNA
<213> ORGANISM: Artificial Sequence
<220> FEATURE:
<223> OTHER INFORMATION: PCR Primer

<400> SEQUENCE: 9
aaactctttc agctccatga ccactact                                             28

<210> SEQ ID NO 10
<211> LENGTH: 29
<212> TYPE: DNA
<213> ORGANISM: Artificial Sequence
<220> FEATURE:
<223> OTHER INFORMATION: PCR Primer for UBQ10

<400> SEQUENCE: 10
ccatggatga aatgtatgcg ttatggtta                                            29

<210> SEQ ID NO 11
<211> LENGTH: 28
<212> TYPE: DNA
<213> ORGANISM: Artificial Sequence
<220> FEATURE:
<223> OTHER INFORMATION: PCR Primer

<400> SEQUENCE: 11
ggtgtcagaa ctctccacct caagagta                                             28

<210> SEQ ID NO 12
<211> LENGTH: 29
<212> TYPE: DNA
<213> ORGANISM: Artificial Sequence
<220> FEATURE:
<223> OTHER INFORMATION: PCR Primer

<400> SEQUENCE: 12
tcaattctct ctaccgtgat caagatgca                                            29
```

-continued

```
<210> SEQ ID NO 13
<211> LENGTH: 724
<212> TYPE: PRT
<213> ORGANISM: Sacharum officinarum
<220> FEATURE:
<221> NAME/KEY: VARIANT
<222> LOCATION: 5017
<223> OTHER INFORMATION: Xaa = Any Amino Acid
<220> FEATURE:
<221> NAME/KEY: VARIANT
<222> LOCATION: 666
<223> OTHER INFORMATION: Xaa = Any Amino Acid

<400> SEQUENCE: 13
```

Met Ala Ala Ala Asp Arg Gln Leu Val Val Ala Val Glu Gly Thr Ala
1               5                   10                  15

Ala Leu Gly Pro Tyr Trp Ser Thr Ile Val Ala Glu Tyr Val Glu Lys
            20                  25                  30

Ile Val Arg Ser Phe Cys Ala Ser Glu Leu Pro Gly Gln Lys Leu Ala
        35                  40                  45

Gly Ala Pro Pro Glu Leu Ala Leu Val Val Phe His Thr His Gly Pro
    50                  55                  60

Tyr Ser Ala Phe Asp Val Gln Arg Ser Gly Trp Thr Lys Asp Thr Asp
65                  70                  75                  80

Ala Phe Leu Ser Trp Leu Ser Gly Ile Ser Phe Ser Gly Gly Gly Phe
                85                  90                  95

Ser Glu Ala Ser Thr Cys Glu Gly Leu Ala Glu Ala Leu Lys Ile Leu
            100                 105                 110

Gln Gly Ser Pro Asn Thr Thr Gln Ser His Gln Asn His Glu Ala Gln
        115                 120                 125

Lys His Cys Ile Leu Val Ala Ala Ser Asn Pro Tyr Pro Leu Pro Thr
    130                 135                 140

Pro Val Tyr Cys Leu Pro Thr Gln Ser Thr Asp His Lys Glu Asn Ile
145                 150                 155                 160

Glu Thr Ala Lys Glu Pro Ser Ile Ala Asp Ala Glu Thr Val Ala Lys
                165                 170                 175

Ser Phe Ala Gln Cys Ser Val Ser Leu Ser Val Ile Ser Pro Lys Gln
            180                 185                 190

Leu Pro Thr Leu Lys Ala Ile Tyr Asn Ala Gly Lys Arg Asn Pro Arg
        195                 200                 205

Ala Ala Asp Pro Ser Val Asp His Ala Lys Asn Pro His Phe Leu Val
    210                 215                 220

Leu Leu Ser Glu Asn Phe Met Glu Ala Arg Thr Ala Leu Ser Arg Pro
225                 230                 235                 240

Leu His Gly Asn Leu Ala Pro Asn Gln Thr Ile Thr Lys Met Asp Thr
                245                 250                 255

Ala Pro Ala Val Thr Met Pro Gly Pro Thr Ser Asn Ala Asn Pro Ser
            260                 265                 270

Gly Arg Gln Pro Val Val Gly Gly Ile Ser Thr Ala Thr Val Lys Val
        275                 280                 285

Glu Pro Ala Thr Met Pro Pro Ile Val Ser Ala Pro Ala Phe Ser His
    290                 295                 300

Val Thr Pro Ile Ser Asn Val Ala Ser Gln Gly Ile Ser Ala Leu Gln
305                 310                 315                 320

Thr Ser Ser Pro Ser Leu Ile Ser Gln Glu Ala Asn Met Ala Asn Asp
                325                 330                 335

```
Asn Val Gln Glu His Lys Pro Ile Ile Asn Pro Val Gln Pro Val
            340                 345                 350

Arg Pro Gly Gly His Gly Ser Leu Leu Asn Asn Leu Ser Gln Val Arg
            355                 360                 365

Leu Met Asn Ser Thr Ser Leu Gly Gly Ala Thr Ser Met Gly Leu
            370                 375                 380

Pro Asn Ile Gly Ala Thr Pro Ile Gln Val His Met Ser Asn Met Ile
385                 390                 395                 400

Ser Ser Gly Met Thr Ser Thr Pro Ser Val Ile Ser Ser Met Ser Gly
            405                 410                 415

Pro Gly His Pro Ile Gly Thr Gln Gln Met Ile Gln Ser Thr Ala Leu
            420                 425                 430

Gly Ser Phe Gly Ser Asn Thr Ser Thr Val Ser Gly Asn Ser Asn Val
            435                 440                 445

Ala Val Ser Ser Ser Leu Thr Asn Asn Gln Ser Ser Met Gly Met Gly
            450                 455                 460

Gln Ser Val Gln Pro Val Ala Gln Gly Gly Leu Val Ala Gly Ser Gln
465                 470                 475                 480

Leu Gly Gln Gly Gly Ile Gly Ala Asn Gln Asn Val Met Ser Ser Leu
            485                 490                 495

Gly Ser Thr Ala Ile Ser Ser Ala Pro Ala Met Met Pro Thr Pro Gly
            500                 505                 510

Met Val Pro Gln Thr Gly Val Asn Ser Leu Gly Val Asn Asn Asn Pro
            515                 520                 525

Ala Met Asn Met Pro Ile Pro Gln His Ala Asn Ala Gln Gln Pro Ala
            530                 535                 540

Pro Lys Tyr Val Lys Ile Trp Glu Gly Thr Leu Ser Gly Gln Arg Gln
545                 550                 555                 560

Gly Gln Pro Val Phe Ile Cys Lys Leu Glu Gly Tyr Arg Ser Gly Thr
                565                 570                 575

Ala Ser Glu Thr Leu Ala Ala Asp Trp Pro Glu Thr Met Gln Ile Val
            580                 585                 590

Arg Leu Ile Ala Gln Glu His Met Asn Asn Lys Gln Tyr Val Gly Lys
            595                 600                 605

Ala Asp Phe Leu Val Phe Arg Thr Leu Asn Gln His Gly Phe Leu Gly
            610                 615                 620

Gln Leu Gln Glu Lys Lys Leu Cys Ala Val Ile Gln Leu Pro Ser Gln
625                 630                 635                 640

Thr Leu Leu Leu Ser Met Ser Asp Lys Ala Arg Arg Leu Ile Gly Met
                645                 650                 655

Leu Phe Pro Ala Asp Met Val Val Ser Xaa Pro Gln Val Pro Thr Gln
            660                 665                 670

Gln Thr Gln Leu Gln Gln Gln Leu Gln Gln Gln Leu Pro Lys Gln
            675                 680                 685

Gln Gln Leu Gln Gln Glu Leu Gln Gln Gln His Met His Met Gln
            690                 695                 700

His Gln Ala Ser Asn Ser Glu Ala Glu Met His Phe Ser Lys Ala Glu
705                 710                 715                 720

Ala Gln Met Pro

<210> SEQ ID NO 14
<211> LENGTH: 582
<212> TYPE: PRT
<213> ORGANISM: Sorghum bicolor
```

<400> SEQUENCE: 14

```
Thr Arg Tyr Trp Ser Thr Ile Val Ala Glu Tyr Val Glu Lys Ile Val
  1               5                  10                  15

Arg Ser Phe Cys Ala Ser Glu Leu Pro Gly Gln Lys Leu Ala Gly Pro
             20                  25                  30

Pro Pro Glu Leu Ala Leu Val Val Phe His Thr His Gly Pro Tyr Ser
             35                  40                  45

Ala Phe Asp Val Gln Arg Ser Gly Trp Thr Lys Asp Thr Asp Ala Phe
         50                  55                  60

Leu Ser Trp Leu Ser Gly Ile Ser Phe Ser Gly Gly Phe Ser Glu
 65                  70                  75                  80

Ala Ser Thr Cys Glu Gly Leu Ala Glu Ala Leu Lys Ile Leu Gln Gly
                 85                  90                  95

Ser Pro Asn Ala Thr Gln Ser His Gln Asn His Glu Ala Gln Lys His
                100                 105                 110

Cys Ile Leu Val Ala Ala Ser Asn Pro Tyr Pro Leu Pro Thr Pro Val
                115                 120                 125

Tyr Cys Leu Pro Thr Gln Ser Thr Asp His Lys Glu Asn Ile Glu Thr
130                 135                 140

Ser Lys Glu Pro Ser Ile Ala Asp Ala Glu Thr Val Ala Lys Ser Phe
145                 150                 155                 160

Ala Gln Cys Ser Val Ser Leu Ser Val Ile Ser Pro Lys Gln Leu Pro
                165                 170                 175

Thr Leu Lys Ala Ile Tyr His Glu Ala Val Val Ala Val Glu Ala Phe
                180                 185                 190

Arg Ala Tyr Lys Glu Lys Val Ala Asn Leu Thr Gly Val Thr Arg Lys
                195                 200                 205

Phe Met Gly Asn Leu Val Lys Ala Phe Lys Thr Asn Leu Pro Glu Val
            210                 215                 220

Val Val Thr Pro Ala Ala Phe Asp Phe Asp His Ile Val Asn Gly Pro
225                 230                 235                 240

Thr Met Gly Ser Gln Thr Ala Gly Val Gly Gly Ile Ile Ser Thr Ala
                245                 250                 255

Thr Val Thr Leu Glu Gln Pro Ala Met Glu Pro Met Val Ser Gly Ser
            260                 265                 270

Ala Gly Phe Trp His Ser Ala Leu Gln Gln Pro Ser Ser Ser Ser Leu
        275                 280                 285

Ile Ser Gln Glu Ala Asn Ile Ala Asn Asp Ser Val Gln Glu His Arg
        290                 295                 300

Pro Ile Arg Ser Pro Val Gln His Pro Val Arg Pro Gly Arg His Gly
305                 310                 315                 320

Gly Leu Leu Ser Asn Pro Ser Gln Phe Gln Pro Ile His Ser Thr Phe
                325                 330                 335

Phe Gly Glu Ala Thr Thr Ser Met Gly Pro Pro Asn Ile Gly Ala Ile
                340                 345                 350

Thr Pro Leu Gln Phe Asn Met Ser Asn Met Ile Ser Ser Gly Ala Thr
            355                 360                 365

Ser Thr Pro Leu Val Thr Phe Ser Met Ser Ala Pro Gly Gln Pro Ile
370                 375                 380

Gly Asn Gln Asp Met Val Gln Ser Thr Ala Leu Gly Ser Phe Gly Ser
385                 390                 395                 400

Asn Thr Ser Thr Ala Trp Asp Asn Ser Asp Ile Ala Glu Ser Ser Ser
                405                 410                 415
```

```
Gln Pro Asn Ser Met Ala Met Asn Arg Gln Ala Gly Ile Asn Pro Leu
            420                 425                 430

Ser Ser Ala Met Asn Ala Pro Ile Gly Met His His Asn Ala Gln Gln
            435                 440                 445

Pro Pro Pro Lys Tyr Val Lys Ile Trp Glu Gly Thr Leu Ser Gly Gln
            450                 455                 460

Arg Gln Gly Arg Pro Val Phe Ile Ser Arg Leu Glu Gly Trp Ser Gly
465                 470                 475                 480

Ile Val Ser Lys Thr Val Ala Ala Asp Trp Pro Glu Thr Met Gln Ile
                485                 490                 495

Val Arg Leu Ile Ala Gln Glu His Met Asn Asn Lys Gln Tyr Val Trp
                500                 505                 510

Lys Gly Arg Leu Ser Asn Ile Ser Asp Phe Lys Ser Ala Trp Phe Leu
            515                 520                 525

Gly Gln Leu Gln Glu Arg Lys Leu Cys Ala Val Ile Gln Leu Pro Ser
            530                 535                 540

Gln Thr Leu Pro Leu Ser Met Ser Asp Lys Ala Gly Arg Met Ile Gly
545                 550                 555                 560

Met Leu Phe Pro Glu Asn Met Val Ile Phe Lys Pro Glu Val Val Thr
                565                 570                 575

Gln Pro Ser Leu Val Arg
            580

<210> SEQ ID NO 15
<211> LENGTH: 741
<212> TYPE: PRT
<213> ORGANISM: Medicago truncatula
<220> FEATURE:
<221> NAME/KEY: VARIANT
<222> LOCATION: 1381
<223> OTHER INFORMATION: Xaa = Any Amino Acid
<220> FEATURE:
<221> NAME/KEY: VARIANT
<222> LOCATION: 177, 188, 451, 454, 458
<223> OTHER INFORMATION: Xaa = Any Amino Acid

<400> SEQUENCE: 15

Met Ala Glu Lys Gln Leu Ile Val Ala Val Glu Thr Ala Ala Met
 1               5                  10                  15

Gly Pro Tyr Trp Asp Thr Leu Leu Met Asp Tyr Leu Glu Lys Ile Val
            20                  25                  30

Arg Cys Leu Gly Gly Asn Glu Ser Thr Gly Gln Lys Pro Ser Gly Ser
            35                  40                  45

Asn Val Glu Phe Ser Leu Val Thr Tyr Asn Thr His Gly Cys Tyr Ser
        50                  55                  60

Gly Ile Leu Val Gln Arg Thr Gly Trp Thr Arg Asp Pro Asp Val Phe
 65                 70                  75                  80

Leu Gln Trp Leu Glu Ser Ile Pro Phe Ser Gly Gly Gly Phe Asn Asp
                85                  90                  95

Ala Ala Ile Ala Glu Gly Leu Ala Glu Ala Leu Met Met Phe Pro Pro
            100                 105                 110

Ser Gln Ser Gly Gly Leu Asn Gln Gln Asn Val Asp Thr Asn Met His
            115                 120                 125

Cys Ile Leu Val Ala Ala Ser Asn Pro Tyr Pro Leu Gln Thr Pro Val
        130                 135                 140

Tyr Val Pro Gln Leu Gln Ser Leu Glu Lys Thr Glu Ser Ile Asp Ser
145                 150                 155                 160
```

-continued

```
Asn Gln Val Asn Gln Leu Tyr Asp Ala Glu Ala Val Ala Lys Ala Phe
            165                 170                 175

Xaa Gln Phe Asn Ile Ser Leu Ser Val Val Cys Xaa Lys Gln Asn Phe
            180                 185                 190

Ser His Leu Gln Cys Gly Arg Ala Lys Gly Arg Ser Ala Asp Pro Pro
            195                 200                 205

Val Asp Pro Lys Thr Thr His Phe Leu Ile Leu Ile Ser Glu Gly Phe
210                 215                 220

Arg Glu Ala Arg Ser Ala Leu Ser Arg Pro Gly Thr Asn Met Pro Ser
225                 230                 235                 240

Asn Gln Ser Pro Val Lys Val Asp Ala Val Ser Ala Thr Pro Val Thr
            245                 250                 255

Gly Ala Pro Pro Ser Ser Leu Pro Ser Val Asn Gly Ser Ile Pro Asn
            260                 265                 270

Arg Gln Pro Ile Pro Ala Gly Asn Val Thr Pro Ala Thr Val Lys Val
            275                 280                 285

Glu Gln Val Pro Val Thr Ser Gly Pro Ala Phe Ser His Asn Pro Ser
            290                 295                 300

Val Pro Arg Ala Thr Gly Thr Gly Leu Gly Val Pro Ser Leu Gln Thr
305                 310                 315                 320

Ser Ser Pro Ser Ser Val Ser Gln Asp Ile Met Thr Ser Asn Glu Asn
            325                 330                 335

Ala Met Asp Thr Lys Pro Ile Val Ser Met Leu Gln Pro Ile Arg Pro
            340                 345                 350

Val Asn Pro Ala Gln Ala Asn Val Asn Ile Leu Asn Asn Leu Ser Gln
            355                 360                 365

Ala Arg Gln Val Met Ala Leu Ser Gly Gly Thr Ser Met Gly Leu Gln
            370                 375                 380

Ser Met Gly Gln Thr Pro Val Ala Met His Met Ser Asn Met Ile Ser
385                 390                 395                 400

Ser Gly Thr Thr Ser Ser Gly Pro Thr Gly Gln Asn Val Phe Ser Ser
            405                 410                 415

Gly Pro Ser Val Ile Thr Ser Ser Gly Ser Leu Thr Ala Ser Ala Gln
            420                 425                 430

Val Gly Gln Asn Ser Gly Leu Ser Ser Leu Thr Ser Ala Thr Ser Asn
            435                 440                 445

Ser Ser Xaa Cys Leu Xaa Glu Phe Leu Xaa Phe Val Arg Gly Gly Lys
            450                 455                 460

Val Arg Ser Lys Phe Val Val Leu Arg Gly Pro Ala Lys Met Met Gln
465                 470                 475                 480

Asn Gly Val Asn Met Asp Glu Ile Gly Gly Gln Ser His Glu Thr Gln
            485                 490                 495

Asn Gly Trp His Arg Ser Ser Pro Ile Trp Glu Gly Ser Leu Tyr Gly
            500                 505                 510

Arg Lys Gln Gly Glu Pro Ile Phe Ile Thr Lys Leu Glu Gly Tyr Arg
            515                 520                 525

Arg Ser Ser Ala Ser Glu Thr Leu Ala Ala Asn Trp Pro Pro Glu Met
            530                 535                 540

His Ile Val Arg Ile Ile Ser Gln Asp His Met Asn Asn Lys Lys Tyr
545                 550                 555                 560

Val Gly Glu Ala Asp Phe Leu Val Phe Arg Ala Arg Asn Thr His Gly
            565                 570                 575
```

```
Phe Leu Gly Leu Leu Gln Glu Lys Lys Leu Cys Ala Val Ile Gln Leu
                580                 585                 590
Gln Ser Gln Thr Leu Leu Leu Ser Val Ser Asp Lys Ala Cys Arg Leu
            595                 600                 605
Met Gly Val Leu Phe Pro Gly Asp Lys Leu Val Ser Lys Ser Gln Leu
        610                 615                 620
Ser Gly Gln Gln Gln Gln Gln Met Gln Gln Gln Met Gln Gln
625                 630                 635                 640
His Gln Gln Met Gln Ser Gln Gln His Leu Pro Gln Leu Gln Gln
                645                 650                 655
Gln Met Gln Gln Gln Gln Gln Gln Leu Pro Gln Leu Gln Gln
            660                 665                 670
Asn Gln Gln Leu Ser Gln Ile Gln Gln Ile Pro Gln Leu Gln Gln
        675                 680                 685
Gln Gln Gln Gln Leu Pro Gln Leu Gln Gln Gln Leu Ser Gln Leu
    690                 695                 700
Gln Gln Gln Gln Gln Leu Pro Gln Leu Gln Gln Leu Gln His Gln
705                 710                 715                 720
Gln Leu Pro Gln Gln Gln Met Gly Trp Cys Trp Asn Gly Ser Asn
                725                 730                 735
Leu Cys Ser Arg Ser
            740

<210> SEQ ID NO 16
<211> LENGTH: 15075
<212> TYPE: DNA
<213> ORGANISM: O. Sartiva

<400> SEQUENCE: 16
ggcacccgat tcttagttac tccctccatt ccataatata agggattttg agttttttatt    60 tgcattgttt gaccactcat cttatttaaa aaaattgtgc aaatataaaa aacgaaaagt    120
tgtgcttaaa atactttgaa taataaagta agtcacacaa aaaataaata ataattccaa    180 attttttaa taagacgagt ggtcaaacag tgcaaataaa aactcaaaat cccttatatt    240
atgggacgga gggagtacct cctaaaaata cccttagttt agccgaaagg ctacactcaa    300
aactaacctg atgtatacta agaaagtaat aaatgctcac aattcttccc aactatagag    360
taccattatt attacattta ctaaacacca taaaagaaca atacaactct ttttacacc    420 aaaatttccc catattcccc tatggccca cctgtcatcc acacaaaagc ccacctttct    480
tcttatgggc cttgggccc atataaatta gaccccagta ccccaccct tcgccgtcat    540 ctctctctaa cctcacgaaa cctaacaaga agaagaagaa gagaaattcc ggcaaggaag    600
ggagggaggg agaagtcgtt ggtgcggggg agattgattt cgcgggaggg aggggagctc    660
gagaggcggt gattcgggga gtcggcaggg tggcgccggg tgcggcggcg gcggggcgg    720 ccgtcggggg gatggcggcg gcggcggccg agaggcagct ggtggtggcc gtggaggga    780 cggcggcgct ggggccgtac tggcccgtca ccgtggcgga ctacgtcgag aagatcgtgc    840
ggtaatgctg cgcccgtgct ttcctccccc cgccgcgcca ccctgctttc ttgttactag    900
ttgactgtac ggccgtcgcg gattagtgca tcttggattt cttgatgtgg aagaattgga    960 cccttttgttg attgtttagc tgttttatttt gagacgaagg gagtacatgg aacgcgaagc    1020
ggtagctagt tagttcttga tagtggaagt tagcagctat ccgtgtatgt gtttgatata    1080
cacagttttt tagttatatt agtcggatat atcgttcact ccaagcatta gtaggagatt    1140
```

```
tggagatttg ttgtttgctc tcaccttctt aattgcaaac attaaatggt actagttagc    1200
ttcaattctg tttcacaatg cttattcaaa gagtaagaat gcaagcgcat catcgatgtg    1260
tggaaattcg tggtttcttg atgaactggt tggttgttgg ctatatggtg ttgtggcacg    1320
agatacatct ttttttgctc ctgattcgag gagactttgt atcactgcat atgtgcagat    1380 ctatgcacaga atgtagcata attcatcttc tactttgggt tttatgcctt ttctagttcc    1440
tccttgctca ttcagaagta ttttttcttca gtctagcata ttttagtgtt ttttttttca    1500
tgaatgatga atgattccca tgaaaaccaa tttcagtttt tggctggtga ttttactact    1560
cttctgtaca accagtaatg taatgatggg atgtctgttt ggttatggtt atggcttttc    1620
tgaagtcctt gttttcactc ttgttaatta gttgatgttc tggtttcgca tgggtgtaat    1680
tggaatattc atcacatgag tcaaatttct tgtgttcaag cctttcaaat aaaaaaaata    1740
atgaaagtgg gagctgtttg tattgttggt caataatcag tttgctctga attattaggg    1800
tttgtttgca gttgctatcc tcctgtgctt attatttagc ttctgtggaa acagttaaga    1860
aaaacttcgt agtctgtttg agaaatcaaa ttaatgttag acgaattctg ttagtcaatt    1920
taaactgtta tttctctgac aagtgttctg tttttagaac tgaaataata tctctatttg    1980
caacttgatt aaaagagcag cagttagcca aacatcaaaa tttctataag ctactgtacg    2040
gaacaggatt atcatagtcc acctcaacgc aaaatccaaa tggagccttt gatgttatgt    2100
ggtgatccac cacagcttca ctctcatata cttactatca tgaaactttt aagctcatct    2160
cttgctagaa atttttgtca atttctgtag cacttagtaa cctttgcatt tttagtacta    2220
ctattcatga agcatttcaa tttatgcagg agttttttgtg cacatgaaat ggcaggacag    2280
gtaatttgct ctcagtattt atcgtcggac ttactacttg atccatgttt ccttgacttg    2340
tgtcaaaact caaaagtgta aattattatc gtgttatgca gaagctcgca gggacacccc    2400
ctgaacttgc attagtcgtc ttccataccc atggtcctta tagcggtaaa gtttgatatc    2460
ctccatgccc taagcttttt attatgatcc attgcaatta tttgtattta gttctatatc    2520
aacaaaacat gtaagctatg ataattcgct tttgattcct tgcagctttt tgtgtgcaac    2580
ggagtggatg gacaaaagat atgaatgtgt ttctttcatg gttatctgga atatcattta    2640
gtggtggagg ctttagtgaa gctgctattt ctgaaggtct tgctgaagca ttgatggtat    2700
tgacatattg gcatcgttca gttcttttca cttttttgcac ataatgactt cctctggtgt    2760
ttcctgtact ttttttttttt ggttcaaaat gcataaatta gaaactgtgg cttactactt    2820
ccaaaatttc agtactgcat atggttgcct acttttgagt tcccgtgcaa ggttttagca    2880
ttttgtttgg cttgtgcaat catgcttcat ttggcatatg aaatgatgtt tcttttttgc    2940
caaatggcac atctttcatg ttaacatcaa cagtagcaac ctttagttcc aggcaagttg    3000
gurbgggtag gctagagatg aaactgatgt gcagccacaa aaaaactaag ggaagtatag    3060
tactagtaat aacaatatag ttaaagaaga cgtgaattag gtcatgattc tgggcatgtg    3120
gaccgccaat ttccatgcaa ctctatccaa aaccataatt catctccaca ggaacgactg    3180 ggattttat gatggcttac caatgttatc gcaacattct tcctttactc agcgttagga    3240
ccagctatgc tgaagcaaag gcagagtttg gtatcttatt aacagagata ttttgatttc    3300
ctagatgaag ggaaataccct cttttcatct ctcactgcac ctgaatttgg gtccagtttt    3360
gtctaaatta gttgatctac aattttgttt ctcatagtaa gccctgtaaa ctattagttg    3420
agcctggaca ttatgtagaa ccatgatact taacaataca tgttctaccc aacctttggg    3480
attactttat tttccaagaa ttatagcttg ttgtcttggt attgttattt ccagtattct    3540
```

```
ctagaatctg tcctttaatg cccttctgca caacatatga ttcatgtgag aaaattctaa    3600
ggtggtttgc acatccactt atcagctatt gtctcataaa aaatgtcttg atctggatat    3660
cagctacaga tagccttacc ttagtaaata gagtgtataa ctgtaatcac catttcatta    3720
ggttaatttt tgtaaggaag attttcatta gatcaaccct attaggaaac tggatgtctg    3780
ggccagtacc cagaataagc agagtgaaac tagtatgatc agaagtttaa attctatgaa    3840
tgtacctata ttagtatgtt aattttccta tggtactgag tcttcaaaaa tcaaaatttc    3900
agtcttcatc cctactatta taaagaggga atcgtcctcc tccacctcca cataaaagcc    3960
tctttcctcc ataaaaactg tccaccctaa aaaaaactgt ttactaataa agccaaccat    4020
tgtataaaca ccgaacagct cactgggccc aaatcctccc actaaactta ataaaaaaaa    4080
ccattgcaat gcatgacagc atgagcctat aactagttga aaaatacttg ggtctttgaa    4140
tttgatatca ttttatttct tgagttctct atgaattaaa gtatttattg cctttatgat    4200
tttatttcct gtgtgcaact agatactcca aggcagttct agtaacagtc agaatcatca    4260
aagccatgaa gtacaaaaac attgcatact tgttgcagca agtaatcctt atccactgcc    4320
tacgcctgtc taccgccccc ttgttcaaag tagcgatcac aaggagaaca atgatggagc    4380
aaaagaatct tgtcttgctg atgctgagac tgttgcaaaa tcatttgctc aggtcctaca    4440
caaatactga tatctagcat attgctgatt acctgtgttt caatgaagtg gtcagcagtc    4500
attgttggtt ctaattaatt ttacttatat tgatgtagtg ctccgtttca ttgtcggtgg    4560
tatctcctaa acagcttcca actctgaaag caatatacaa tgcggtaatt tcgttatttt    4620
gttttgctaa attctgtaag ccacaagcca tctttaataa tcttctcctg gtattttact    4680
tgttcattga tggtatgata gttgcatctt gatttacaga gggttgaaaa actcacttaa    4740
gaatatatct tttaaaataa attataagca tgaacttgca gaactggccg ctccactatt    4800
acatatgttc ttgtacttgt acacagtact aaacttcata ttttcattac cattgaaata    4860
aaaagagtaa attttatcaa acaccaccta ttatggtcca agttgcacaa aaccacaggg    4920
attttggcac atgacacata accccatgta ttatggccct aaggtttaac aagaccacac    4980
cgttaaccaa ttttacatac tcctatatca aagttttaaa agttttagtt acattcatgt    5040
aacatttata tgatggataa aaaactcata aatttgtgat gtgattttat aaatgatcaa    5100
tagtgtggtt gtgtgaaact ttatagctat aatacctggt ggttaagtgt cacgtgccaa    5160
aacccatgtg gttttgtgca acttagacca caacacctaa aggttaagtg aaatttactc    5220
aaataaaaat gaactcagtt tggattgtac tgtcattgta tcttatttgt ggataagaaa    5280
aatatccatt tatttcattt ttttaattag ttagtatcct gcctgaactt gctagctagt    5340
ctttgtatgg tttacagact ataaatctat gaattggcat cctttatctat cattagttta    5400 atacaagcat ttttttaactt acatgatata aattttatct tctgcaagac cttcgacagt    5460
ttgtactgat gaataatttg caccaggtgc tgatgttgtc catgttttgt tgcaggcaaa    5520
gaggaatcct cgagcggctg acccatcagt ggatcatgca aaaaatccac attttcttgt    5580
tttgttgtct gacaattttt tggaggctcg aactgctcta agtcgccctt tacctggcaa    5640
cttggtcaca aatcaccccca ttacaaaaat ggatacagct gcaacatctg tgccagtacc    5700
aacttcaaat ggcaacccct caggttgaac aaatgctaac atttggctta gtcttgccat    5760
ggtatttagc ctttagttct gttcctcttt tggacgaaag gttgtgacgt tgttacgatg    5820
tttgtgaata tgtaggtgct tacacatagt ctagcgtgag tctgctttaa caaatgcttg    5880
acacagcttt gttaaggaaa aaaatgttag gctaaagtga aataaaccat tgccataatt    5940
```

```
actccatggg ctgaagcaac ataggttaac aattatcgtt gcatatattg gtacgcctga    6000 ctatttttaat agcaggaagg attctggcaa tgcccttatg ccatccattt ttggcccgaa   6060
aaaagcatat cattgagttt tcaaagcctt agaggaataa aatgtattgt gagctctcct    6120
ctattatgaa cacgatgtgc ttgtgcatct gacattacat gggactacaa tataatttcc    6180
tatagtttat ctccaattg tcaagtacag atgccttgag ctggagatga agaaaaatgg    6240
atgtgurcac tgaatacaca aacgtgaaaa cctgcctcct aaaagcttgt accattgtgt    6300
tctatttgtc cccttcccat ctgggtggtt tttcaattgt agtgccaaga aaacatagat    6360
tattctataa tgattgtgtc ttcatggtta tcattggcat ggggtcacaa ctaattgttt    6420
ggactctgag tgataatgct ttcaatggca tggtgtcttc ggattgatga attctatatg    6480
gataacaagt tttgttttc agcatcttaa tcaaaattaa cactgaggat acaaatatat    6540
cgcaattcct gttttatac acagcaatgt ggttttaaag gtattcgtgg atatacataa     6600
tttgttgttt ttgtgagtgt tgatgaagcc ccttcattgt ttgtttcata aataaaattt    6660
tacagtttaa tgttatgaaa tgccaaattc ttattgttg tattgtacat tgctatgtac     6720
taatatatgc cagattgccc atctacctaa ttaaagtgga acatatttca agtctagcca    6780
attgctggtt ttatttgcat gatccagttg tgataaatct ggaattgcct tatatagaaa    6840 tttgttttg gcttctggtt atatccgtat cattactatc ttccatactg aacatgacta    6900
actgttataa gtattttttca gttaatggac ctatgcttac ccgccaacca aatggtgttg    6960
ttgcaaatat taaaacggta aagctttgaa caacatactc tgtgacttac cattttgctg    7020
tatgttttct cattgtgaaa acaatcatca ctttcaggag ccaacaactt taccgcccat    7080
ggtttctgca cctgctttct cgcatgtaac acctgttgca aatggtgttt cacaaggatt    7140
atcatcagta caaagtccct caccgtccct tatttcacag gaaactaatc ttgcaaatga    7200
tagtgtgcaa gaacataagc ctttaataaa ccctatccaa cagtcaattc gacctggtgg    7260
tccagcaaat gtcagcatcc tcaacaatct atcacagcat cggtcagtgg caaccattat    7320
atcaggtgga atgcctggca tccctatgtc tggaacagga cagtcaattg gtagtcaaca    7380
agtcgtacaa aacactgctt ttggatcaaa cacacccata acaggcaatt caaatattgc    7440
tgtgtcatct tctttgggtg gcatccaaag caatatcgtt atatcagggc tcctgtgac     7500 acagggaggt tcaatgggta gtacgcaatt gggacaaggt ggaatcaata caaaccaaaa    7560
tatgataagt agccttggga caacaactgt ctcttctgca cctgcaatga tgccaacacc    7620
agggatggct caacaggcag gtgtaaattc tcttggtgtg accaacagtt ctgccatgaa    7680
catgcctata gtgcagcatc ctaatgcgca gcagcagcaa cagcaacagc aacagcagca    7740
gcagcagcag ccaccgccga gtacgtcaa aatttgggag gtaaaagatt ctgtctttgt    7800
ctagcatcca tgtagcaatt ggctctaccc tccaaccctc tagtagctta gtagttgttt    7860
gctaaatata aaaggaaata ttccgtatga cacacatgta atttaatgtt tttctaattc    7920
tgaccatgag ctgcaataat atatgcaccc tcccaactat tgaaatcgtt tgcctcaaaa    7980
ataaaaaagg aactatttaa acccttctgc taatcaacca gatgagatag ggctgtgaat    8040
ggtcagagtt agtctctta ttttttggcc ttttaacagt tcccaacctg ctttttcctt     8100
gagaaagcct tcctgagata aaagacaac aatttgaagg ttgacctctg ggaattcagc     8160
ctggtgttgt cctttgtggc agtgttttg acttcaagtg ctgagtcatg tcctattaac    8220
caaagaagaa agtagtggac ccaccattga agatgctgat tattttttca tccgagtaaa    8280
gcctatttta ccatcctcaa ctgtgttagt ctagaaatca acctcagcag aggccccctt    8340
```

```
cgtaccatga accatgctgg tggtggaagg ggtgcgacta ttctgcaata ccctatagac    8400
acatgccacg tgtctctagg ggcaggtcat ttgcggcatc aaggtgacac ataaatcgcc    8460
ttgatctgtt ggcattagca aaggtgttga agggtctagt tagtaagaaa ctaacattag    8520
tctttaatct attctcccct gtccttgtgg agttgtggtg cagctgcttc gatggtattg    8580
tctctccgtg tgcaaggaca cctcaattaa gtgcataaga acctgtatgg ctgtatccat    8640
accacattca tttcatgtat gaagaatact tccctaaaag agctaacata cgagcacatg    8700
attatatcta aattagtttg aagtcaactg cttattttc cgtgtcattt ttggttgttt     8760
atatattagt aatgtaaatt ttatgttcta tttatcgtgt ctcaagttgc ctatgttgat    8820
gatactggta tcatcagtca atatatgatt tgtttgttgt ggatgcataa tatgtaatgt    8880
ttctattttt atttcaggga actttatctg ggcaaaggca aggacaacct gtatttatct    8940
gtaaacttga agtaagtttc tgtttgttgg atgaattgtc tgtgactccg actattatca    9000
cccccctaac tctgcccaca cagatgacct ttgctcatta ttatgcccat ttgaagctga    9060
ctgtctcaga aagaaaaaaa gatcacaaga atccctgaat tgtatatatt atttgtacga    9120
tcatgattgt tcaaatcttc tgttgtcact gaaatgaaat tatgtatttc atagtttcag    9180
tgtgcacctt tatagctgga atatagtggc tatccttttg ttgtaactac ttgtcctaca    9240
ttttttttg tttcaacaca tttatctgca caaagcatat actttagtta aatttctgac    9300
ttttagcatg tctcacaggg ttacaggagt ggaacagcat ctgaaacgta agttttcgaa    9360
ttgttgcaat gttcttgcat tctttttttt tttttgtag ttctgttttg tgtctattaa     9420
tggttgtatt cgaaccaaca aatcacccaa tgtcggtatg ccctatttta gtattgtttt    9480
gtagaagagu rdactggagc aatggctgat tggtagctgc ttggtattca caagtttctg    9540
ttccatgcaa caactagtta agccattgct tgttttaaa aaataaactg tactgtacaa     9600
aaggtctacg gtacaagacc aaaatggaag caactcaagt tataatgttg gaagttttta    9660
gatataatca atgaatgctg tggatttgct ttatactccc tccgtctcat attataaggg    9720
attttgggtg tatgtgacat atcctatgtc caggttcgta gtactaagga tatgtcacat    9780
ccacccaaaa tcccttataa tataggactg agggagtagt acagtgcctt aatcttgtta    9840
agtgaatgga acctccaaac cgatcttgca aaattcctaa taggatattt tgcctaatat    9900
agaaatgtct tgttcccttg cactgaacat gtaccttcta taatgtcgtt cccttgcact    9960
gaacatgtac cttctttgtc cagacttgca gcagactggc ctgaaacaat gcagattgtg   10020
cgccttatag ctcaggagca tatgaacaat aagtttgtct cagccactcc atttccatgt   10080
taaaaatgat ccattctaca ttctcataat ttgaatcatt ctctcttttg tttttgttta   10140
tttgtttatt ctgcagacaa tatgttggaa aagcagactt tctagtattt cggacattaa   10200
atcagcacgg cttccttggg caactgcagg aaaagaagct ggtcagtgca taatttaacc   10260
tgtttaatgt ttattattat ttcatgccac aattatttgg tcccacatct attgcatgcc   10320
actcatatgg gtccttcaac tagtcaaatt agtccccaag ctttgttaat tggctcattg   10380
taatccctgt gcctatgtgt caccgcatgt tgtctcatct cactcaagtc agcgactagg   10440
tacctagggt ctccagccaa cctagagtat gggacaaccg aattccgttt gctaaattat   10500
gtaatataat tgaagacaga agtaggctgc tgttatgctt gagggcatat cagtcatttt   10560
atatagtctt gggtggcctc aggttcccag cagatcaagg caatgtttga tggttgaggg   10620
atacatgaac tattaatcct tccgtttaat caatcatcac ttcttaaatt tctgttaatg   10680
tttcgagtgg acttctgttt cagtgcgcag tgattcaact gccttcgcaa actttgttgt   10740
```

```
tgtcagtgtc agacaaagct gggcgcctca ttggcatgct gttccctggg gtacgttgat    10800
tgcagttgcg gctatctcta tctgccttgc tgtttaccat ttttccgctg tagctgaagt    10860
aattcctttc cccccaggat atggtggtgt ttaaaccgca ggtaccaacc cagcagccac    10920
caatgcagca acaacagtta caacagcagc agaaccaact acaacagcag aatcagctcc    10980
accagcagca ccagctgcaa ccacagaacc agctgcaaca gcaacaccag ctgcaacaac    11040
agttacaaca gcagcaacta caacaacaca tgcaactgca gacacaaggc cttccgcttc    11100
agcagcagca atcccaaggc catccgcttc agcagcagca gatgcagcaa atgcagcaac    11160
aacagcagca gcagcagatt cagcaaatgc agcagcagca gcagatgcag cagatgcaac    11220
agcagcagca gcagccccaa cagcttcagc agcagcagca accgcagatg gtcggcacag    11280
ggatggggca gcagcaacca cagatggtcg gcacggggat ggggcagcag caaccgcaga    11340
tggtcggcgc agggatgggg cagcaataca tgcaggggca cggtaggacg gtgcagcaga    11400
tgatgcaagg gaagatggcg ccgcagggtc caggaagcat gccgggtgca gggagcatgc    11460
ctggggtggg ctacctatct tgaagcacct gatagcctga atgccagaag aataagtggg    11520
caatttaacc cagcccttttt ggctgcacaa gctatatagc tcatggatta cttgcccagc    11580
atcctaggta attttcccac cttagtgtgg gatacatagt aggtgttctc agtagtttgg    11640
ttttggctgt gatgttttac ctgtagatag cgtcttggag cctacacggc ctcatgttgt    11700
gttttgtgta gcttcttttg atgtcactgc cttatgctta gcttgtagct gctggaagca    11760
gatcaaattt aaaggattaa ttaattaata gtaactctgt ttaaggattg attgaccaat    11820
ttcacttggg agcctcccaa ataaatatga ctgccttagg attttttcagc tttgtaattg    11880 atgcatcaag agtatggcag agtggcagta actgattaaa attattgtca tcaaattcga    11940
accaatttac cctaaattaa aatgctggcc tatgaaggaa tccaaacata ttgggattac    12000
acaggcaaga tcattcacag aaaaagatac gttcaagatg accatgacga tgaaaaaggg    12060
cctgcatagg aattaaattg tctgcccacg gtgctaaaca acaaacaaaa taaacttttta    12120 tgtaaatatt gctaaccata tcattacagt ttggtcttga tactgctcta cagttatgag    12180
taacatcaat tacaataaat agaatcgaga agagttctaa atgaaacaat gaccgcccca    12240
gccttcaatt ttcttccctc caaaacacat gttagctttc aattcttcag acatctttt    12300 ttccaaaaac aaacaaact attggaatgg ccagaaccag tacaagtgca ttttactcta    12360
caggttggcc aatgatttgt atgcgtcaat ttttctttgg atccgagctt ccgttcaggt    12420
agccttcaag aattgtgttg caggcattca tggctcgcgc atccagtaga ctgtggttcc    12480
agagtttgac cataaaaaac ctccaacacc tgttcatcca gcgataaaaa gttgcaaatg    12540
aaacaaacag ctaaagagag gtgtctgcat ctgtaggcaa caagctacac acgcaaggca    12600
aggcattgat caatactata ttcttataat cagccactta ccatagtaga gctggatttt    12660
gtacaagttc ttgtccatga aactgcgaga atgcttcgca tgcccaggga atatggccat    12720
ccgctagtac ccgurtgcaa ttttccactt ttcagtaaga cggttgaaat atgcagtaga    12780
taatgaataa aatgactgca catatgtaaa aggaatcaag tgcccttgca gttctgatgt    12840
cactgcttaa ctcttggtat ggaaaaaaga agaaaaaaaa agtaaaaaca atcctttggg    12900
catatagttg gtagagatag aggtgggatt caatgtagat gagggtgct agcccatgac    12960 aatgtatggt tgattacgta cgccacaggc aacaacagca tggtgatata tgtgcgctta    13020
ggatgcccaa atgcgactgg gagtagtgtt ggtggcatcg gcaaaggtgc gagaaacaga    13080
ggtgctgaca atcatggcat cttagtaaag gttagcagca aggaggaaga aggcattact    13140
```

```
agtattagtt tttccgtcct aagaaaataa caatcagagc cataacacct ggcacattac    13200
aagttgtaat tcatggctct taacccatgc aattcttaaa aaaaaaaaac atgcaacatc    13260
ttcatggaag aaatccttca tgatagtttc agacatggta tgcaaatgaa tataaatgtc    13320
tgttcaccaa gctgtatacc acaataatag ataatggata tagcggggaa ggcctgacct    13380
ttgtttccga acaaatgaat tccacatatg cataataagt ttctcgtctt ttgtaacatc    13440
aacaaaatca tcaagcatct gcatttactc agggaagtta aggtatcaag aatttggaca    13500
catttatgta tgagaacaga gcaagcatag taaacttact cttctatctt caaaatcagc    13560
aatgtcatca tcaacttcat cttcactatc acgatctgag aaaacttgct ccaatgccat    13620
tggctacaac agtgtaacta tgtagtcaag ctagatttca attttatttg agccagactt    13680
caaacggatg caaaaagat catgtcttca taattaaaaa aaaaatgaca aaaggggaag    13740
aggggctcaa gtttggccat ccaaccatag attctccaca taagattagc tagatatgca    13800
tgcgtttcca aagtggctgg ttttgaaatc tgttactgca aagtttgata atatatatat    13860
gccagtgaat gtgaaatatg ccattgtgaa taattttgga ccaaagcacc cctgtttctt    13920
attcctccat tatccttaat tcattgtttt cctgtcgcca tgggggcccc cacaactaaa    13980
atttgcctca tgcactagat ccacatggtg gctataacca aggctgagct acccgcatgg    14040
actcatgatg agcatccatg ttactgccat atccacagga ttgagctttt ctacagcata    14100
acgttgctgg ggttacttgg gctaagatgc tgccatgctc acccctttggg atagcagtgg    14160 ttcaaaccag tgattgctgt gtcaacggca acgtgtgata tctgtgttga cttgatcctc    14220
aaacatggga agtctcgggt gaaacctcac caaaatggag tgaaatgtga atcaggtgtt    14280
cagccagact tggggaagat ggtcatgcca gccctatgcc aagtgacatg actgggaggg    14340
agggaaagat cccactgagt acaacagtgg cagttagcca tgggagggtg atacaagttg    14400
gcaatgctat atttcaaagg gaaaacattt cccagaccat ggattctttt tctggcagcc    14460
aggtccctga tgccttagtc atcggcaagc ttgatttggc acttagtcag ttctgatcct    14520
ttcctacagt tcatccttt tctctatttc tattttgttg acccagtaac tagtccaaaa    14580
accctggtta ttcttggtta cgtaacttac tactccctcc aatttcccaa ctgatcatca    14640
tataactttt ttaaggttat tcccaaatga tcatcatatt agtattcatt cactaagtct    14700
gttcgttatt ctgtgcatgg gagtagatgg acattggtgc atgcgtccat gcatacaatc    14760
ctttacaacc aacatgcaat gttttgattt gttagtggct aggaagtatt ggggatagtg    14820
catgcaagtt tgttaccgaa ttaaatgtag tatgagagaa ttattagctt tccttggtct    14880
tggtcttata atatgatgat caattgggaa tggaggtagt agtaagaaat cgattagttt    14940
tttagatgag aaatgcagac gagtagggag gacatttttct gatgtttctc tcgtgaccat    15000
ccagagtgat agcaggaaac ttttgattga cgtatagaaa atttccaccat ctatataacc    15060 ctttattaac tccaa                                                    15075
```

<210> SEQ ID NO 17
<211> LENGTH: 832
<212> TYPE: PRT
<213> ORGANISM: O. Sartiva

<400> SEQUENCE: 17

Trp Arg Arg Arg Arg Pro Arg Gly Ser Trp Trp Pro Trp Arg Gly
 1               5                  10                  15

Arg Arg Arg Trp Gly Arg Thr Gly Pro Ser Pro Trp Arg Thr Thr Ser
            20                  25                  30

-continued

Arg Arg Ser Cys Glu Lys Leu Ala Gly Thr Pro Pro Glu Leu Ala Leu
        35                  40                  45

Val Val Phe His Thr His Gly Pro Tyr Ser Ala Phe Cys Val Gln Arg
    50                  55                  60

Ser Gly Trp Thr Lys Asp Met Asn Val Phe Leu Ser Trp Leu Ser Gly
65                  70                  75                  80

Ile Ser Phe Ser Gly Gly Phe Ser Glu Ala Ala Ile Ser Glu Gly
                85                  90                  95

Leu Ala Glu Ala Leu Met Ile Leu Gln Gly Ser Ser Asn Ser Gln
                100                 105                 110

Asn His Gln Ser His Glu Val Gln Lys His Cys Ile Leu Val Ala Ala
        115                 120                 125

Ser Asn Pro Tyr Pro Leu Pro Thr Pro Val Tyr Arg Pro Leu Val Gln
    130                 135                 140

Ser Ser Asp His Lys Glu Asn Asn Asp Gly Ala Lys Glu Ser Cys Leu
145                 150                 155                 160

Ala Asp Ala Glu Thr Val Ala Lys Ser Leu Leu Arg Cys Ser Val Ser
                165                 170                 175

Leu Ser Val Val Ser Pro Lys Gln Leu Pro Thr Leu Lys Ala Ile Tyr
            180                 185                 190

Asn Ala Ala Lys Arg Asn Pro Arg Ala Ala Asp Pro Ser Val Asp His
        195                 200                 205

Ala Lys Asn Pro His Phe Leu Val Leu Leu Ser Asp Asn Phe Leu Glu
    210                 215                 220

Ala Arg Thr Ala Leu Ser Arg Pro Leu Pro Gly Asn Leu Val Thr Asn
225                 230                 235                 240

His Pro Ile Thr Lys Met Asp Thr Ala Ala Thr Ser Val Pro Val Pro
                245                 250                 255

Thr Ser Asn Gly Asn Pro Ser Val Asn Gly Pro Met Leu Thr Arg Gln
            260                 265                 270

Pro Asn Gly Val Val Ala Asn Ile Lys Thr Glu Pro Thr Thr Leu Pro
        275                 280                 285

Pro Met Val Ser Ala Pro Ala Phe Ser His Val Thr Pro Val Ala Asn
    290                 295                 300

Gly Val Ser Gln Gly Leu Ser Ser Val Gln Ser Pro Ser Pro Ser Leu
305                 310                 315                 320

Ile Ser Gln Glu Thr Asn Leu Ala Asn Asp Ser Val Gln Glu His Lys
                325                 330                 335

Pro Leu Ile Asn Pro Ile Gln Gln Ser Ile Arg Pro Gly Gly Pro Ala
            340                 345                 350

Asn Val Ser Ile Leu Asn Asn Leu Ser Gln His Arg Ser Val Ala Thr
        355                 360                 365

Ile Ile Ser Gly Gly Met Pro Gly Ile Pro Met Ser Gly Thr Gly Gln
    370                 375                 380

Ser Ile Gly Ser Gln Gln Val Val Gln Asn Thr Ala Phe Gly Ser Asn
385                 390                 395                 400

Thr Pro Ile Thr Gly Asn Ser Asn Ile Ala Val Ser Ser Ser Leu Gly
                405                 410                 415

Gly Ile Gln Ser Asn Ile Gly Ile Ser Gly Pro Pro Val Thr Gln Gly
            420                 425                 430

Gly Ser Met Gly Ser Thr Gln Leu Gly Gln Gly Gly Ile Asn Thr Asn
        435                 440                 445

-continued

```
Gln Asn Met Ile Ser Ser Leu Gly Thr Thr Val Ser Ser Ala Pro
        450             455             460
Ala Met Met Pro Thr Pro Gly Met Ala Gln Gln Ala Gly Val Asn Ser
465             470             475             480
Leu Gly Val Thr Asn Ser Ser Ala Met Asn Met Pro Ile Val Gln His
                485             490             495
Pro Asn Ala Gln Gln Gln Gln Gln Gln Gln Gln Gln Gln Gln Gln Gln
            500             505             510
Gln Pro Pro Pro Lys Tyr Val Lys Ile Trp Glu Gly Thr Leu Ser Gly
        515             520             525
Gln Arg Gln Gly Gln Pro Val Phe Ile Cys Lys Leu Glu Gly Tyr Arg
        530             535             540
Ser Gly Thr Ala Ser Glu Thr Leu Ala Ala Asp Trp Pro Glu Thr Met
545             550             555             560
Gln Ile Val Arg Leu Ile Ala Gln Glu His Met Asn Asn Lys Gln Tyr
                565             570             575
Val Gly Lys Ala Asp Phe Leu Val Phe Arg Thr Leu Asn Gln His Gly
                580             585             590
Phe Leu Gly Gln Leu Gln Glu Lys Lys Leu Cys Ala Val Ile Gln Leu
        595             600             605
Pro Ser Gln Thr Leu Leu Leu Ser Val Ser Asp Lys Ala Gly Arg Leu
        610             615             620
Ile Gly Met Leu Phe Pro Gly Asp Met Val Val Phe Lys Pro Gln Val
625             630             635             640
Pro Thr Gln Gln Pro Pro Met Gln Gln Gln Gln Leu Gln Gln Gln Gln
                645             650             655
Asn Gln Leu Gln Gln Gln Asn Gln Leu His Gln Gln His Gln Leu Gln
        660             665             670
Pro Gln Asn Gln Leu Gln Gln Gln His Gln Leu Gln Gln Gln Leu Gln
        675             680             685
Gln Gln Gln Leu Gln Gln His Met Gln Leu Gln Thr Gln Gly Leu Pro
        690             695             700
Leu Gln Gln Gln Gln Ser Gln Gly His Pro Leu Gln Gln Gln Gln Met
705             710             715             720
Gln Gln Met Gln Gln Gln Gln Gln Gln Gln Ile Gln Gln Met Gln
                725             730             735
Gln Gln Gln Gln Met Gln Gln Met Gln Gln Gln Gln Gln Gln Pro Gln
            740             745             750
Gln Leu Gln Gln Gln Gln Pro Gln Met Val Gly Thr Gly Met Gly
        755             760             765
Gln Gln Gln Pro Gln Met Val Gly Thr Gly Met Gly Gln Gln Gln Pro
        770             775             780
Gln Met Val Gly Ala Gly Met Gly Gln Gln Tyr Met Gln Gly His Gly
785             790             795             800
Arg Thr Val Gln Gln Met Met Gln Gly Lys Met Ala Pro Gln Gly Pro
            805             810             815
Gly Ser Met Pro Gly Ala Gly Ser Met Pro Gly Gly Gly Tyr Leu Ser
            820             825             830
```